(12) United States Patent
Bertin

(10) Patent No.: US 7,321,028 B2
(45) Date of Patent: Jan. 22, 2008

(54) MOLECULES OF THE PYRIN DOMAIN PROTEIN FAMILY AND USES THEREOF

(75) Inventor: John Bertin, Watertown, MA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 459 days.

(21) Appl. No.: 10/132,967

(22) Filed: Apr. 26, 2002

(65) Prior Publication Data

US 2003/0170841 A1 Sep. 11, 2003

Related U.S. Application Data

(60) Division of application No. 09/653,901, filed on Sep. 1, 2000, now abandoned, which is a continuation-in-part of application No. 09/506,067, filed on Feb. 17, 2000, now abandoned.

(51) Int. Cl.
C07H 21/02 (2006.01)
C07H 21/04 (2006.01)
C12P 21/06 (2006.01)

(52) U.S. Cl. ............... 536/23.1; 435/69.1; 536/23.4

(58) Field of Classification Search ............... 536/23.1; 530/350
See application file for complete search history.

(56) References Cited

FOREIGN PATENT DOCUMENTS

| WO | WO 99/46290 | 9/1999 |
|---|---|---|
| WO | WO 01/30971 A2 | 5/2001 |
| WO | WO 01/30971 A3 | 5/2001 |

OTHER PUBLICATIONS

Mao et al., Identification of genes expressed in human CD34l hematopoietic stemyprogenitor cells by expressed sequence tags and efficient full-length cDNA cloning, Proc. Natl. Acad. Sci. USA, vol. 95, pp. 8175-8180, Jul. 1998.*
Mathews and Van Holde, Biochemistry, 1996, pp. 165-171.*
Lazar et al., Transforming Growth Factor ox: Mutation of Aspartic Acid 47 and Leucine 48 Results in Different Biological Activities Molecular and Cellular Biology, vol. 8, p. 1247-1252, 1988.*
Schwartz et al., A Superactive Insulin: [B 10-aspartic Acid]Insulin(Human) Proc Natl Acad Sci USA, vol. 84, p. 6408-6411, 1987.*
Lin et al.,., Structure-function relationships in glucagon: properties of highly purified des-His-1-, monoiodo-, and (des-Asn-28, Thr-29)(homoserine lactone-27)-glucagon. Biochemistry USA, vol. 14, p. 1559-1563, 1975.*
Burgess et al, Possible Dissociation of the Heparin-binding and Mitogenic Activities of Heparin-binding (Acidic Fibroblast) Growth Factor-1 from Its Receptor-binding Activities by Site-directed Mutagenesis Journal of Cell biology, vol. 111, p. 2129-2138, 1990.*
Burgess et al, Journal of Cell biology, vol. 111, p. 2129-2138, 1990.*
Lin et al Biochemistry USA, vol. 14, p. 1559-1563, 1975.*

Baker et al., "Signaling in Plant-Microbe Interactions," Science 276:726-733 (May 2, 1997).
Bertin et al., "Human CARD4 Protein Is a Novel CED-4/Apaf-1 Cell Death Family Member That Activates NF-κB", J. Biol. Chem. 274(19):12955-12958. (May 7, 1999).
Booth et al., "Pyrin/marenostrin mutations in familial Mediterranean fever," QJM 91(9):603-6, (Sep. 1998).
GenBank Accession No. AA205674, (Jan. 27, 1997).
GenBank Accession No. AA205775, (Jan. 27, 1997).
GenBank Accession No. AA381361, (Apr. 21, 1997).
GenBank Accession No. AA773929, (Jan. 29, 1998).
GenBank Accession No. AAC39910 (May 22, 2001).
GenBank Accession No. AAD51762, (May 10, 2000).
GenBank Accession No. AF054176 (May 22, 2001).
GenBank Accession No. AK000517, (Feb. 22, 2000).
GenBank Accession No. AL049734, (Jan. 11, 2000).
GenBank Accession No. AW468866 (Feb. 24, 2000).
GenBank Accession No. W22630, (May 6, 1996).
Hofmann et al., "The Card Domain: a New Apoptotic Signalling Motif", TIBS, 22:155-156, (1997).
Imai et al., "The CED-4-Homologous Protein FLASH Is Involved In Fas-Mediated Activation of Caspase-8 During Apoptosis", Nature, 398:777-85, (1999).
Nicholson, "Caspase Structure, Proteolytic Substrates, and Function During Apoptotic Cell Death", Cell Death and Differentiation, 6:1028-1042, (Apr. 29, 1999).
Schwander et al., "Peptidoglycan- and Lipoteichoic Acid-induced Cell Activation Is Mediated by Toll-like Receptor 2," J. of Biol. Chem. 274(25):17406-17409 (Jun. 18, 1999).
van der Biezen et al., "The NB-ARC domain: a novel signaling motif shared by plant resistance gene products and regulators of cell death in animals," Current Biology, 8(7):R226-R227, R7.
Yang et al., "Signaling events induced by lipopolysaccharide-activated toll-like receptor 2," J Immunol. 163(2):639-43, (Jul. 15, 1999).
Yang et al., "Toll-like receptor-2 mediates lipopolysaccharide-induced cellular signaling," Nature 395(6699):284-8, (Sep. 17, 1998).
Yoshimura et al., "Cutting Edge: Recognition of Gram-Positive Bacterial Cell Wall Components by the Innate Immune System Occurs Via Toll-Like Receptor 2[1]" Journal of Immunology, 163:1-5, (1999).
Bertin et al., "The PYRIN domain: a novel motif found in apoptosis and inflammation proteins," Cell Death and Differentiation 7:1273-1274 (2000).

(Continued)

Primary Examiner—Shanon Foley
Assistant Examiner—Lei Yao

(57) ABSTRACT

Novel NBS-1 or PYRIN-1 polypeptides, proteins, and nucleic acid molecules are disclosed. In addition to isolated NBS-1 or PYRIN-1 proteins, the invention further provides NBS-1 or PYRIN-1 fusion proteins, antigenic peptides and anti-NBS-1 or anti-PYRIN-1 antibodies. The invention also provides NBS-1 or PYRIN-1 nucleic acid molecules, recombinant expression vectors containing a nucleic acid molecule of the invention, host cells into which the expression vectors have been introduced and non-human transgenic animals in which a NBS-1 or PYRIN-1 gene has been introduced or disrupted. Diagnostic, screening and therapeutic methods utilizing compositions of the invention are also provided.

32 Claims, 20 Drawing Sheets

OTHER PUBLICATIONS

Masumoto et al., "ASC, a Novel 22-kDa Protein, Aggregates during Apoptosis of Human Promyelocytic Leukemia HL-60 Cells," J. Biological Chemistry 274(48):33835-33838 (1999).

Accession No. AAZ20641 (Nov. 26, 1999).
Accession No. AC011476 (Oct. 8, 1999).
Accession No. AC023386 (Feb. 15, 2000).

* cited by examiner

```
CAGCCCTCAT CTCCGCCGGC GAGTAGGGCC AGGTGTTGGG AGCTCCCACG TGGGACAAGG      60
TGGTGTCTTC GGCGCAG                                                     77
```

| | | | | | | | | | | | | | | | |
|---|---|---|---|---|---|---|---|---|---|---|---|---|---|---|---|
| atg | ggt | ttc | aac | ctg | cag | gct | ctc | ctg | gag | cag | ctc | agc | cag | gat | gag | 125
| Met | Gly | Phe | Asn | Leu | Gln | Ala | Leu | Leu | Glu | Gln | Leu | Ser | Gln | Asp | Glu |
| 1 | | | | 5 | | | | | 10 | | | | | 15 | |

| ttg | agc | aag | ttc | aag | tat | ctg | atc | acg | acc | ttc | tcc | ccg | gca | cac | gag | 173
| Leu | Ser | Lys | Phe | Lys | Tyr | Leu | Ile | Thr | Thr | Phe | Ser | Pro | Ala | His | Glu |
| | | | 20 | | | | | 25 | | | | | 30 | | |

| ctc | cag | aag | atc | ccc | cac | aag | gag | gta | gac | aag | gct | gat | ggg | aag | caa | 221
| Leu | Gln | Lys | Ile | Pro | His | Lys | Glu | Val | Asp | Lys | Ala | Asp | Gly | Lys | Gln |
| | | | 35 | | | | | 40 | | | | | 45 | | |

| ctg | gta | gaa | atc | ctc | acc | acc | cat | tgt | gac | agc | tac | tgg | gtg | gag | atg | 269
| Leu | Val | Glu | Ile | Leu | Thr | Thr | His | Cys | Asp | Ser | Tyr | Trp | Val | Glu | Met |
| | 50 | | | | | 55 | | | | | 60 | | | | |

| gcg | agc | ctc | cag | gtc | ttt | gaa | aag | atg | cac | cga | atg | gat | ctg | tct | gag | 317
| Ala | Ser | Leu | Gln | Val | Phe | Glu | Lys | Met | His | Arg | Met | Asp | Leu | Ser | Glu |
| 65 | | | | | 70 | | | | | 75 | | | | | 80 |

| aga | gca | aag | gat | gaa | gtc | aga | gaa | gca | gct | ttg | aaa | tcc | ttt | aat | aaa | 365
| Arg | Ala | Lys | Asp | Glu | Val | Arg | Glu | Ala | Ala | Leu | Lys | Ser | Phe | Asn | Lys |
| | | | | 85 | | | | | 90 | | | | | 95 | |

| agg | aag | cct | cta | tca | tta | ggg | ata | aca | cgg | aaa | gaa | cga | cca | cct | cta | 413
| Arg | Lys | Pro | Leu | Ser | Leu | Gly | Ile | Thr | Arg | Lys | Glu | Arg | Pro | Pro | Leu |
| | | | 100 | | | | | 105 | | | | | 110 | | |

| gac | gtg | gac | gaa | atg | ctg | gag | cgc | ttc | aaa | aca | gaa | gca | caa | gac | aaa | 461
| Asp | Val | Asp | Glu | Met | Leu | Glu | Arg | Phe | Lys | Thr | Glu | Ala | Gln | Asp | Lys |
| | | | 115 | | | | | 120 | | | | | 125 | | |

| gac | aat | agg | tgc | agg | tat | ata | ttg | aag | acg | aag | ttc | cgg | gag | atg | tgg | 509
| Asp | Asn | Arg | Cys | Arg | Tyr | Ile | Leu | Lys | Thr | Lys | Phe | Arg | Glu | Met | Trp |
| | 130 | | | | | 135 | | | | | 140 | | | | |

| aag | agc | tgg | cct | gga | gat | agc | aaa | gag | gtc | cag | gtt | atg | gct | gag | aga | 557
| Lys | Ser | Trp | Pro | Gly | Asp | Ser | Lys | Glu | Val | Gln | Val | Met | Ala | Glu | Arg |
| 145 | | | | 150 | | | | | 155 | | | | | | 160 |

| tac | aag | atg | ctg | atc | cca | ttt | agc | aac | ccc | agg | gtg | ctt | ccc | ggg | ccc | 605
| Tyr | Lys | Met | Leu | Ile | Pro | Phe | Ser | Asn | Pro | Arg | Val | Leu | Pro | Gly | Pro |
| | | | | 165 | | | | | 170 | | | | | 175 | |

| ttc | tca | tac | acg | gtg | gtg | ctg | tat | ggt | cct | gca | ggc | ctt | ggg | aaa | acc | 653
| Phe | Ser | Tyr | Thr | Val | Val | Leu | Tyr | Gly | Pro | Ala | Gly | Leu | Gly | Lys | Thr |
| | | | 180 | | | | | 185 | | | | | 190 | | |

| acg | ctg | gcc | cag | aaa | cta | atg | cta | gac | tgg | gca | gag | gac | aac | ctc | atc | 701
| Thr | Leu | Ala | Gln | Lys | Leu | Met | Leu | Asp | Trp | Ala | Glu | Asp | Asn | Leu | Ile |
| | | 195 | | | | | 200 | | | | | 205 | | | |

FIG. 1A

```
cac aaa ttc aaa tat gcg ttc tac ctc agc tgc agg gag ctc agc cgc      749
His Lys Phe Lys Tyr Ala Phe Tyr Leu Ser Cys Arg Glu Leu Ser Arg
    210                 215                 220 ctg ggc ccg tgc agt ttt gca gag ctg gtc ttc agg gac tgg cct gaa      797
Leu Gly Pro Cys Ser Phe Ala Glu Leu Val Phe Arg Asp Trp Pro Glu
225                 230                 235                 240 ttg cag gat gac att cca cac atc cta gcc caa gca cgg aaa atc ttg      845
Leu Gln Asp Asp Ile Pro His Ile Leu Ala Gln Ala Arg Lys Ile Leu
                245                 250                 255 ttc gtg att gac ggc ttt gat gag ctg gga gcc gca cct ggg gcg ctg      893
Phe Val Ile Asp Gly Phe Asp Glu Leu Gly Ala Ala Pro Gly Ala Leu
            260                 265                 270 atc gag gac atc tgc ggg gac tgg gag aag aag aag ccg gtg ccc gtc      941
Ile Glu Asp Ile Cys Gly Asp Trp Glu Lys Lys Lys Pro Val Pro Val
        275                 280                 285 ctc ctg ggg agt ttg ctg aac agg gtg atg tta ccc aag gcc gcc ctg      989
Leu Leu Gly Ser Leu Leu Asn Arg Val Met Leu Pro Lys Ala Ala Leu
290                 295                 300 ctg gtc acc acg cgg ccc agg gcc ctg agg gac ctc cgg atc ctg gcg     1037
Leu Val Thr Thr Arg Pro Arg Ala Leu Arg Asp Leu Arg Ile Leu Ala
305                 310                 315                 320 gag gag ccg atc tac ata agg gtg gag ggc ttc ctg gag gag gac aag     1085
Glu Glu Pro Ile Tyr Ile Arg Val Glu Gly Phe Leu Glu Glu Asp Lys
                325                 330                 335 agg gcc tat ttc ctg aga cac ttt gga gac gag gac caa gcc atg cgt     1133
Arg Ala Tyr Phe Leu Arg His Phe Gly Asp Glu Asp Gln Ala Met Arg
            340                 345                 350 gcc ttt gag cta atg agg agc aac gcg gcc ctg ttc cag ctg ggc tcg     1181
Ala Phe Glu Leu Met Arg Ser Asn Ala Ala Leu Phe Gln Leu Gly Ser
        355                 360                 365 gcc ccc gcg gtg tgc tgg atc gtg tgc acg act ctg aag ctg cag atg     1229
Ala Pro Ala Val Cys Trp Ile Val Cys Thr Thr Leu Lys Leu Gln Met
370                 375                 380 gag aag ggg gag gac ccg gtc ccc acc tgc ctc acc cgc acg ggg ctg     1277
Glu Lys Gly Glu Asp Pro Val Pro Thr Cys Leu Thr Arg Thr Gly Leu
385                 390                 395                 400 ttc ctg cgt ttc ctc tgc agc cgg ttc ccg cag ggc gca cag ctg cgg     1325
Phe Leu Arg Phe Leu Cys Ser Arg Phe Pro Gln Gly Ala Gln Leu Arg
                405                 410                 415 ggc gcg ctg cgg acg ctg agc ctc ctg gcc gcg cag ggc ctg tgg gcg     1373
Gly Ala Leu Arg Thr Leu Ser Leu Leu Ala Ala Gln Gly Leu Trp Ala
            420                 425                 430
```

FIG. 1B

```
cag acg tcc gtg ctt cac cga gag gat ctg gaa agg ctc ggg gtg cag    1421
Gln Thr Ser Val Leu His Arg Glu Asp Leu Glu Arg Leu Gly Val Gln
            435                 440                 445 gag tcc gac ctc cgt ctg ttc ctg gac gga gac atc ctc cgc cag gac    1469
Glu Ser Asp Leu Arg Leu Phe Leu Asp Gly Asp Ile Leu Arg Gln Asp
        450                 455                 460 aga gtc tcc aaa ggc tgc tac tcc ttc atc cac ctc agc ttc cag cag    1517
Arg Val Ser Lys Gly Cys Tyr Ser Phe Ile His Leu Ser Phe Gln Gln
465                 470                 475                 480 ttt ctc act gcc ctg ttc tac acc ctg gag aag gag gag gaa gag gat    1565
Phe Leu Thr Ala Leu Phe Tyr Thr Leu Glu Lys Glu Glu Glu Glu Asp
                485                 490                 495 agg gac ggc cac acc tgg gac att ggg gac gta cag aag ctg ctt tcc    1613
Arg Asp Gly His Thr Trp Asp Ile Gly Asp Val Gln Lys Leu Leu Ser
            500                 505                 510 gga gta gaa aga ctc agg aac ccc gac ctg atc caa gca ggc tac tac    1661
Gly Val Glu Arg Leu Arg Asn Pro Asp Leu Ile Gln Ala Gly Tyr Tyr
        515                 520                 525 tcc ttt ggc ctc gct aac gag aag aga gcc aag gag ttg gag gcc act    1709
Ser Phe Gly Leu Ala Asn Glu Lys Arg Ala Lys Glu Leu Glu Ala Thr
530                 535                 540 ttt ggc tgc cgg atg tca ccg gac atc aaa cag gaa ttg ctg cga tgc    1757
Phe Gly Cys Arg Met Ser Pro Asp Ile Lys Gln Glu Leu Leu Arg Cys
545                 550                 555                 560 gac ata agt tgt aag ggt gga cat tca acg gtg aca gac ctg cag gag    1805
Asp Ile Ser Cys Lys Gly Gly His Ser Thr Val Thr Asp Leu Gln Glu
                565                 570                 575 ctc ctc ggc tgt ctg tac gag tct cag gag gag gag ctg gtg aag gag    1853
Leu Leu Gly Cys Leu Tyr Glu Ser Gln Glu Glu Glu Leu Val Lys Glu
            580                 585                 590 gtg atg gct cag ttc aaa gaa ata tcc ctg cac tta aat gca gta gac    1901
Val Met Ala Gln Phe Lys Glu Ile Ser Leu His Leu Asn Ala Val Asp
        595                 600                 605 gtt gtg cca tct tca ttc tgc gtc aag cac tgt cga aac ctg cag aaa    1949
Val Val Pro Ser Ser Phe Cys Val Lys His Cys Arg Asn Leu Gln Lys
610                 615                 620 atg tca ctg cag gta ata aag gag aat ctc ccg gag aat gtc act gcg    1997
Met Ser Leu Gln Val Ile Lys Glu Asn Leu Pro Glu Asn Val Thr Ala
                625                 630                 635                 640 tct gaa tca gac gcc gag gtt gag aga tcc cag gat gat cag cac atg    2045
Ser Glu Ser Asp Ala Glu Val Glu Arg Ser Gln Asp Asp Gln His Met
            645                 650                 655
```

FIG. 1C

| | | | | | | | | | | | | | | | | |
|---|---|---|---|---|---|---|---|---|---|---|---|---|---|---|---|---|
| ctt | cct | ttc | tgg | acg | gac | ctt | tgt | tcc | ata | ttt | gga | tca | aat | aag | gat | 2093 |
| Leu | Pro | Phe | Trp | Thr | Asp | Leu | Cys | Ser | Ile | Phe | Gly | Ser | Asn | Lys | Asp | |
| | | | 660 | | | | 665 | | | | | | 670 | | | |
| ctg | atg | ggt | cta | gca | atc | aat | gat | agc | ttt | ctc | agt | gcc | tcc | cta | gta | 2141 |
| Leu | Met | Gly | Leu | Ala | Ile | Asn | Asp | Ser | Phe | Leu | Ser | Ala | Ser | Leu | Val | |
| | | 675 | | | | | 680 | | | | | 685 | | | | |
| agg | atc | ctg | tgt | gaa | caa | ata | gcc | tct | gac | acc | tgt | cat | ctc | cag | aga | 2189 |
| Arg | Ile | Leu | Cys | Glu | Gln | Ile | Ala | Ser | Asp | Thr | Cys | His | Leu | Gln | Arg | |
| | 690 | | | | | 695 | | | | | 700 | | | | | |
| gtg | gtg | ttc | aaa | aac | att | tcc | cca | gct | gat | gct | cat | cgg | aac | ctc | tgc | 2237 |
| Val | Val | Phe | Lys | Asn | Ile | Ser | Pro | Ala | Asp | Ala | His | Arg | Asn | Leu | Cys | |
| 705 | | | | | 710 | | | | | 715 | | | | | 720 | |
| cta | gct | ctt | cga | ggt | cac | aag | act | gta | acg | tat | ctg | acc | ctt | caa | ggc | 2285 |
| Leu | Ala | Leu | Arg | Gly | His | Lys | Thr | Val | Thr | Tyr | Leu | Thr | Leu | Gln | Gly | |
| | | | | 725 | | | | | 730 | | | | | 735 | | |
| aat | gac | cag | gat | gat | atg | ttt | ccc | gca | ttg | tgt | gag | gtc | ttg | aga | cat | 2333 |
| Asn | Asp | Gln | Asp | Asp | Met | Phe | Pro | Ala | Leu | Cys | Glu | Val | Leu | Arg | His | |
| | | | 740 | | | | | 745 | | | | | 750 | | | |
| cca | gaa | tgt | aac | ctg | cga | tat | ctc | ggg | ttg | gtg | tct | tgt | tcc | gct | acc | 2381 |
| Pro | Glu | Cys | Asn | Leu | Arg | Tyr | Leu | Gly | Leu | Val | Ser | Cys | Ser | Ala | Thr | |
| | | 755 | | | | | 760 | | | | | 765 | | | | |
| act | cag | cag | tgg | gct | gat | ctc | tcc | ttg | gcc | ctt | gaa | gtc | aac | cag | tcc | 2429 |
| Thr | Gln | Gln | Trp | Ala | Asp | Leu | Ser | Leu | Ala | Leu | Glu | Val | Asn | Gln | Ser | |
| | | | 770 | | | | 775 | | | | | 780 | | | | |
| ctg | acg | tgc | gta | aac | ctc | tcc | gac | aat | gag | ctt | ctg | gat | gag | ggt | gct | 2477 |
| Leu | Thr | Cys | Val | Asn | Leu | Ser | Asp | Asn | Glu | Leu | Leu | Asp | Glu | Gly | Ala | |
| 785 | | | | | 790 | | | | | 795 | | | | | 800 | |
| aag | ttg | ctg | tac | aca | act | ttg | aga | cac | ccc | aag | tgc | ttt | ctg | cag | agg | 2525 |
| Lys | Leu | Leu | Tyr | Thr | Thr | Leu | Arg | His | Pro | Lys | Cys | Phe | Leu | Gln | Arg | |
| | | | | 805 | | | | | 810 | | | | | 815 | | |
| ttg | tcg | ttg | gaa | aac | tgt | cac | ctt | aca | gaa | gcc | aat | tgc | aag | gac | ctt | 2573 |
| Leu | Ser | Leu | Glu | Asn | Cys | His | Leu | Thr | Glu | Ala | Asn | Cys | Lys | Asp | Leu | |
| | | | | 820 | | | | | 825 | | | | | 830 | | |
| gct | gct | gtg | ttg | gtt | gtc | agc | cgg | gag | ctg | aca | cac | ctg | tgc | ttg | gcc | 2621 |
| Ala | Ala | Val | Leu | Val | Val | Ser | Arg | Glu | Leu | Thr | His | Leu | Cys | Leu | Ala | |
| | | | 835 | | | | | 840 | | | | | 845 | | | |
| aag | aac | ccc | att | ggg | aat | aca | ggg | gtg | aag | ttt | ctg | tgt | gag | ggc | ttg | 2669 |
| Lys | Asn | Pro | Ile | Gly | Asn | Thr | Gly | Val | Lys | Phe | Leu | Cys | Glu | Gly | Leu | |
| | | | 850 | | | | 855 | | | | | 860 | | | | |
| agg | tac | ccc | gag | tgt | aaa | ctg | cag | acc | ttg | gtg | ctt | tgg | aac | tgc | gac | 2717 |
| Arg | Tyr | Pro | Glu | Cys | Lys | Leu | Gln | Thr | Leu | Val | Leu | Trp | Asn | Cys | Asp | |
| 865 | | | | 870 | | | | | 875 | | | | | 880 | | |

FIG. 1D

```
ata act agc gat ggc tgc tgc gat ctc aca aag ctt ctc caa gaa aaa    2765
Ile Thr Ser Asp Gly Cys Cys Asp Leu Thr Lys Leu Leu Gln Glu Lys
            885                 890                 895 tca agc ctg ttg tgt ttg gat ctg ggg ctg aat cac ata gga gtt aag    2813
Ser Ser Leu Leu Cys Leu Asp Leu Gly Leu Asn His Ile Gly Val Lys
        900                 905                 910 gga atg aag ttc ctg tgt gag gct ttg agg aaa cca ctg tgc aac ttg    2861
Gly Met Lys Phe Leu Cys Glu Ala Leu Arg Lys Pro Leu Cys Asn Leu
        915                 920                 925 aga tgt ctg tgg ttg tgg gga tgt tcc atc cct ccg ttc agt tgt gaa    2909
Arg Cys Leu Trp Leu Trp Gly Cys Ser Ile Pro Pro Phe Ser Cys Glu
    930                 935                 940 gac ctc tgc tct gcc ctc agc aac cag agc ctc gtc act ctg gac ctg    2957
Asp Leu Cys Ser Ala Leu Ser Asn Gln Ser Leu Val Thr Leu Asp Leu
945                 950                 955                 960 ggt cag aat ccc ttg ggg tct agt gga gtg aag atg ctg ttt gaa acc    3005
Gly Gln Asn Pro Leu Gly Ser Ser Gly Val Lys Met Leu Phe Glu Thr
                965                 970                 975 ttg aca tgt tcc agt ggc acc ctc cgg aca ctc agg ttg aaa atc gat    3053
Leu Thr Cys Ser Ser Gly Thr Leu Arg Thr Leu Arg Leu Lys Ile Asp
            980                 985                 990 gac ttt aat gat gaa ctc aat aag ctg ctg gaa gaa ata gaa gaa aaa    3101
Asp Phe Asn Asp Glu Leu Asn Lys Leu Leu Glu Glu Ile Glu Glu Lys
        995                 1000                1005 aac cca caa ctg att att gat act gag aaa cat cat ccc tgg gca gaa    3149
Asn Pro Gln Leu Ile Ile Asp Thr Glu Lys His His Pro Trp Ala Glu
        1010                1015                1020 agg cct tct tct cat gac ttc atg atc                                3176
Arg Pro Ser Ser His Asp Phe Met Ile
1025                1030

TGAATCCCCC CGAGTCATTC ATTCTCCATG AAGTCATCGA TTTTCCAGGT GTTGGTGAAC    3236
TGCCTGTGAC TCCTCTCCTC CCCGGCCCCT ACCCCTCAGG GATAATGAGT TCATTGCTGG    3296
GCTAGATGTT TTAGCCATGA TTCTGCCTCT GTTTTATACC TGCACACATC CTTATCTTTG    3356
TTACATATGA AATATCTGTA TCACGGGTAT ATTGAGAGAA ATAAAGGTCA GAGCATTCAC    3416
AAAAAAAAAA AAAAA                                                     3431
```

FIG. 1E

```
ccacgcgtcc gcccacgcgt ccgggcatct ggggaaacct ttcttccatg gctcaggaca    60
cactcctgga tcgagccaac aggagaactt tctgtgtgga ccgaagccta aggaccctga   120
aaacagctgc agatgaag atg gca agc acc cgc tgc aag ctg gcc agg tac    171
                    Met Ala Ser Thr Arg Cys Lys Leu Ala Arg Tyr
                     1           5                   10
```

```
ctg gag gac ctg gag gat gtg gac ttg aag aaa ttt aag atg cac tta    219
Leu Glu Asp Leu Glu Asp Val Asp Leu Lys Lys Phe Lys Met His Leu
            15                  20                  25
```

```
gag gac tat cct ccc cag aag ggc tgc atc ccc ctc ccg agg ggt cag    267
Glu Asp Tyr Pro Pro Gln Lys Gly Cys Ile Pro Leu Pro Arg Gly Gln
            30                  35                  40
```

```
aca gag aag gca gac cat gtg gat cta gcc acg cta atg atc gac ttc    315
Thr Glu Lys Ala Asp His Val Asp Leu Ala Thr Leu Met Ile Asp Phe
 45                  50                  55
```

```
aat ggg gag gag aag gcg tgg gcc atg gcc gtg tgg atc ttc gct gcg    363
Asn Gly Glu Glu Lys Ala Trp Ala Met Ala Val Trp Ile Phe Ala Ala
 60                  65                  70                  75
```

```
atc aac agg aga gac ctt tat gag aaa gca aaa aga gat gag ccg aag    411
Ile Asn Arg Arg Asp Leu Tyr Glu Lys Ala Lys Arg Asp Glu Pro Lys
            80                  85                  90
```

```
tgg ggt tca gat aat gca cgt gtt tcg aat ccc act gtg ata tgc cag    459
Trp Gly Ser Asp Asn Ala Arg Val Ser Asn Pro Thr Val Ile Cys Gln
            95                 100                 105
```

```
gaa gac agc att gaa gag gag tgg atg ggt tta ctg gag tac ctt tcg    507
Glu Asp Ser Ile Glu Glu Glu Trp Met Gly Leu Leu Glu Tyr Leu Ser
           110                 115                 120
```

```
aga atc tct att tgt aaa atg aag aaa gat tac cgt aag aag tac aga    555
Arg Ile Ser Ile Cys Lys Met Lys Lys Asp Tyr Arg Lys Lys Tyr Arg
    125                 130                 135
```

```
aag tac gtg aga agc aga ttc cag tgc att gaa gac agg aat gcc cgt    603
Lys Tyr Val Arg Ser Arg Phe Gln Cys Ile Glu Asp Arg Asn Ala Arg
140                 145                 150                 155
```

```
ctg ggt gag agt gtg agc ctc aac aaa cgc tac aca cga ctg cgt ctc    651
Leu Gly Glu Ser Val Ser Leu Asn Lys Arg Tyr Thr Arg Leu Arg Leu
            160                 165                 170
```

```
atc aag gag cac cgg agc cag cag gag agg gag cag gag ctt ctg gcc    699
Ile Lys Glu His Arg Ser Gln Gln Glu Arg Glu Gln Glu Leu Leu Ala
            175                 180                 185
```

```
atc ggc aag acc aag acg tgt gag agc ccc gtg agt ccc att aag atg    747
Ile Gly Lys Thr Lys Thr Cys Glu Ser Pro Val Ser Pro Ile Lys Met
            190                 195                 200
```

```
gag ttg ctg ttt gac ccc gat gat gag cat tct gag cct gtg cac acc    795
Glu Leu Leu Phe Asp Pro Asp Asp Glu His Ser Glu Pro Val His Thr
    205                 210                 215
```

FIG. 4A

```
gtg gtg ttc cag ggg gcg gca ggg att ggg aaa aca atc ctg gcc agg      843
Val Val Phe Gln Gly Ala Ala Gly Ile Gly Lys Thr Ile Leu Ala Arg
220             225                 230                 235 aag atg atg ttg gac tgg gca tcg ggg aca ctc tac caa gac agg ttt      891
Lys Met Met Leu Asp Trp Ala Ser Gly Thr Leu Tyr Gln Asp Arg Phe
                240                 245                 250 gac tat ctg ttc tat atc cac tgt cgg gag gtg agc ctt gtg aca cag      939
Asp Tyr Leu Phe Tyr Ile His Cys Arg Glu Val Ser Leu Val Thr Gln
                255                 260                 265 agg agc ctg ggg gac ctg atc atg agc tgc tgc ccc gac cca aac cca      987
Arg Ser Leu Gly Asp Leu Ile Met Ser Cys Cys Pro Asp Pro Asn Pro
        270                 275                 280 ccc atc cac aag atc gtg aga aaa ccc tcc aga atc ctc ttc ctc atg     1035
Pro Ile His Lys Ile Val Arg Lys Pro Ser Arg Ile Leu Phe Leu Met
        285                 290                 295 gac ggc ttc gat gag ctg caa ggt gcc ttt gac gag cac ata gga ccg     1083
Asp Gly Phe Asp Glu Leu Gln Gly Ala Phe Asp Glu His Ile Gly Pro
300                 305                 310                 315 ctc tgc act gac tgg cag aag gcc gag cgg gga gac att ctc ctg agc     1131
Leu Cys Thr Asp Trp Gln Lys Ala Glu Arg Gly Asp Ile Leu Leu Ser
                320                 325                 330 agc ctc atc aga aag aag ctg ctt ccc gag gcc tct ctc atc acc         1179
Ser Leu Ile Arg Lys Lys Leu Leu Pro Glu Ala Ser Leu Leu Ile Thr
        335                 340                 345 acg aga cct gtg gcc ctg gag aaa ctg cag cac ttg ctg gac cat cct     1227
Thr Arg Pro Val Ala Leu Glu Lys Leu Gln His Leu Leu Asp His Pro
        350                 355                 360 cgg cat gtg gag atc ctg ggt ttc tcc gag gcc aaa agg aaa gag tac     1275
Arg His Val Glu Ile Leu Gly Phe Ser Glu Ala Lys Arg Lys Glu Tyr
        365                 370                 375 ttc ttc aag tac ttc tct gat gag gcc caa gcc agg gca gcc ttc agt     1323
Phe Phe Lys Tyr Phe Ser Asp Glu Ala Gln Ala Arg Ala Ala Phe Ser
380                 385                 390                 395 ctg att cag gag aac gag gtc ctc ttc acc atg tgc ttc atc ccc ctg     1371
Leu Ile Gln Glu Asn Glu Val Leu Phe Thr Met Cys Phe Ile Pro Leu
                400                 405                 410 gtc tgc tgg atc gtg tgc act gga ctg aaa cag cag atg gag agt ggc     1419
Val Cys Trp Ile Val Cys Thr Gly Leu Lys Gln Gln Met Glu Ser Gly
            415                 420                 425 aag agc ctt gcc cag aca tct aag acc acc acc gcg gtg tac gtc ttc     1467
Lys Ser Leu Ala Gln Thr Ser Lys Thr Thr Thr Ala Val Tyr Val Phe
        430                 435                 440
```

FIG. 4B

```
ttc ctt tcc agt ttg ctg cag ccc cgg gga ggg agc cag gag cac ggc    1515
Phe Leu Ser Ser Leu Leu Gln Pro Arg Gly Gly Ser Gln Glu His Gly
    445             450                 455 ctc tgc gcc cac ctc tgg ggg ctc tgc tct ttg gct gca gat gga atc    1563
Leu Cys Ala His Leu Trp Gly Leu Cys Ser Leu Ala Ala Asp Gly Ile
460             465                 470                 475 tgg aac cag aaa atc ctg ttt gag gag tcc gac ctc agg aat cat gga    1611
Trp Asn Gln Lys Ile Leu Phe Glu Glu Ser Asp Leu Arg Asn His Gly
                480                 485                 490 ctg cag aag gcg gat gtg tct gct ttc ctg agg atg aac ctg ttc caa    1659
Leu Gln Lys Ala Asp Val Ser Ala Phe Leu Arg Met Asn Leu Phe Gln
            495                 500                 505 aag gaa gtg gac tgc gag aag ttc tac agc ttc atc cac atg act ttc    1707
Lys Glu Val Asp Cys Glu Lys Phe Tyr Ser Phe Ile His Met Thr Phe
        510                 515                 520 cag gag ttc ttt gcc gcc atg tac tac ctg ctg gaa gag gaa aag gaa    1755
Gln Glu Phe Phe Ala Ala Met Tyr Tyr Leu Leu Glu Glu Glu Lys Glu
    525                 530                 535 gga agg acg aac gtt cca ggg agt cgt ttg aag ctt ccc agc cga gac    1803
Gly Arg Thr Asn Val Pro Gly Ser Arg Leu Lys Leu Pro Ser Arg Asp
540                 545                 550                 555 gtg aca gtc ctt ctg gaa aac tat ggc aaa ttc gaa aag ggg tat ttg    1851
Val Thr Val Leu Leu Glu Asn Tyr Gly Lys Phe Glu Lys Gly Tyr Leu
            560                 565                 570 att ttt gtt gta cgt ttc ctc ttt ggc ctg gta aac cag gag agg acc    1899
Ile Phe Val Val Arg Phe Leu Phe Gly Leu Val Asn Gln Glu Arg Thr
        575                 580                 585 tcc tac ttg gag aag aaa tta agt tgc aag atc tct cag caa atc agg    1947
Ser Tyr Leu Glu Lys Lys Leu Ser Cys Lys Ile Ser Gln Gln Ile Arg
    590                 595                 600 ctg gag ctg ctg aaa tgg att gaa gtg aaa gcc aaa gct aaa aag ctg    1995
Leu Glu Leu Leu Lys Trp Ile Glu Val Lys Ala Lys Ala Lys Lys Leu
    605                 610                 615 cag atc cag ccc agc cag ctg gaa ttg ttc tac tgt ttg tac gag atg    2043
Gln Ile Gln Pro Ser Gln Leu Glu Leu Phe Tyr Cys Leu Tyr Glu Met
620                 625                 630                 635 cag gag gag gac ttc gtg caa agg gcc atg gac tat ttc ccc aag att    2091
Gln Glu Glu Asp Phe Val Gln Arg Ala Met Asp Tyr Phe Pro Lys Ile
            640                 645                 650 gag atc aat ctc tcc acc aga atg gac cac atg gtt tct tcc ttt tgc    2139
Glu Ile Asn Leu Ser Thr Arg Met Asp His Met Val Ser Ser Phe Cys
        655                 660                 665
```

FIG. 4C

```
att gag aac tgt cat cgg gtg gag tca ctg tcc ctg ggg ttt ctc cat    2187
Ile Glu Asn Cys His Arg Val Glu Ser Leu Ser Leu Gly Phe Leu His
        670             675             680 aac atg ccc aag gag gaa gag gag gag gaa aag gaa ggc cga cac ctt    2235
Asn Met Pro Lys Glu Glu Glu Glu Glu Lys Glu Gly Arg His Leu
        685             690             695 gat atg gtg cag tgt gtc ctc cca agc tcc tct cat gct gcc tgt tct    2283
Asp Met Val Gln Cys Val Leu Pro Ser Ser Ser His Ala Ala Cys Ser
700             705             710             715 cat gga ttg gtg aac agc cac ctc act tcc agt ttt tgc cgg ggc ctc    2331
His Gly Leu Val Asn Ser His Leu Thr Ser Ser Phe Cys Arg Gly Leu
        720             725             730 ttt tca gtt ctg agc acc agc cag agt cta act gaa ttg gac ctc agt    2379
Phe Ser Val Leu Ser Thr Ser Gln Ser Leu Thr Glu Leu Asp Leu Ser
        735             740             745 gac aat tct ctg ggg gac cca ggg atg aga gtg ttg tgt gaa acg ctc    2427
Asp Asn Ser Leu Gly Asp Pro Gly Met Arg Val Leu Cys Glu Thr Leu
        750             755             760 cag cat cct ggc tgt aac att cgg aga ttg tgg ttg ggg cgc tgt ggc    2475
Gln His Pro Gly Cys Asn Ile Arg Arg Leu Trp Leu Gly Arg Cys Gly
        765             770             775 ctc tcg cat gag tgc tgc ttc gac atc tcc ttg gtc ctc agc agc aac    2523
Leu Ser His Glu Cys Cys Phe Asp Ile Ser Leu Val Leu Ser Ser Asn
780             785             790             795 cag aag ctg gtg gag ctg gac ctg agt gac aac gcc ctc ggt gac ttc    2571
Gln Lys Leu Val Glu Leu Asp Leu Ser Asp Asn Ala Leu Gly Asp Phe
        800             805             810 gga atc aga ctt ctg tgt gtg gga ctg aag cac ctg ttg tgc aat ctg    2619
Gly Ile Arg Leu Leu Cys Val Gly Leu Lys His Leu Leu Cys Asn Leu
        815             820             825 aag aag ctc tgg ttg gtc agc tgc tgc ctc aca tca gca tgt tgt cag    2667
Lys Lys Leu Trp Leu Val Ser Cys Cys Leu Thr Ser Ala Cys Cys Gln
        830             835             840 gat ctt gca tca gta ttg agc acc agc cat tcc ctg acc aga ctc tat    2715
Asp Leu Ala Ser Val Leu Ser Thr Ser His Ser Leu Thr Arg Leu Tyr
        845             850             855 gtg ggg gag aat gcc ttg gga gac tca gga gtc gca att tta tgt gaa    2763
Val Gly Glu Asn Ala Leu Gly Asp Ser Gly Val Ala Ile Leu Cys Glu
860             865             870             875 aaa gcc aag aat cca cag tgt aac ctg cag aaa ctg ggg ttg gtg aat    2811
Lys Ala Lys Asn Pro Gln Cys Asn Leu Gln Lys Leu Gly Leu Val Asn
        880             885             890
```

FIG. 4D

```
tct ggc ctt acg tca gtc tgt tgt tca gct ttg tcc tcg gta ctc agc    2859
Ser Gly Leu Thr Ser Val Cys Cys Ser Ala Leu Ser Ser Val Leu Ser
            895                 900                 905 act aat cag aat ctc acg cac ctt tac ctg cga ggc aac act ctc gga    2907
Thr Asn Gln Asn Leu Thr His Leu Tyr Leu Arg Gly Asn Thr Leu Gly
            910                 915                 920 gac aag ggg atc aaa cta ctc tgt gag gga ctc ttg cac ccc gac tgc    2955
Asp Lys Gly Ile Lys Leu Leu Cys Glu Gly Leu Leu His Pro Asp Cys
        925                 930                 935 aag ctt cag gtg ttg gaa tta gac aac tgc aac ctc acg tca cac tgc    3003
Lys Leu Gln Val Leu Glu Leu Asp Asn Cys Asn Leu Thr Ser His Cys
940                 945                 950                 955 tgc tgg gat ctt tcc aca ctt ctg acc tcc agc cag agc ctg cga aag    3051
Cys Trp Asp Leu Ser Thr Leu Leu Thr Ser Ser Gln Ser Leu Arg Lys
            960                 965                 970 ctg agc ctg ggc aac aat gac ctg ggc gac ctg ggg gtc atg atg ttc    3099
Leu Ser Leu Gly Asn Asn Asp Leu Gly Asp Leu Gly Val Met Met Phe
            975                 980                 985 tgt gaa gtg ctg aaa cag cag agc tgc ctc ctg cag aac ctg ggg ttg    3147
Cys Glu Val Leu Lys Gln Gln Ser Cys Leu Leu Gln Asn Leu Gly Leu
            990                 995                 1000 tct gaa atg tat ttc aat tat gag aca aaa agt gcg tta gaa aca ctt    3195
Ser Glu Met Tyr Phe Asn Tyr Glu Thr Lys Ser Ala Leu Glu Thr Leu
        1005                1010                1015 caa gaa gaa aag cct gag ctg acc gtc gtc ttt gag cct tct tgg tag    3243
Gln Glu Glu Lys Pro Glu Leu Thr Val Val Phe Glu Pro Ser Trp  *
1020                1025                1030 gagtggaaac ggggctgcca gacgccagtg ttctccggtc cctccagctg ggggccctca    3303
ggtggagaga gctgcgatcc atccaggcca agaccacagc tctgtgatcc ttccggtgga    3363
gtgtcggaga agagagcttg ccgacgatgc cttcctgtgc agagcttggg catctccttt    3423
acgccagggt gaggaagaca ccaggacaat gacagcatcg ggtgttgttc tcatcacagc    3483
gcctcagtta gaggatgttc ctcttggtga cctcatgtaa ttagctcatt caataaagca    3543
ctttctttat ttttctcttc tctgtctaac tttctttttc ctatcttttt ttcttctttg    3603
ttctgtttac ttttgctcat atcatcattc ccgctaactt tctattaact gaccataaca    3663
cagaactagt tgactatata ttatgttgaa attttatggc agctatttat ttatttaaat    3723
tttttgtaat agttttgttt ctaataaga aaaatccatg cttttgtag ctggttgaaa      3783
attcaggaat atgtaaaact ttttggtatt taattaaatt gattccttt cttaattta      3843
aaaaaaaaaa aaaa                                                       3857
```

FIG. 4E

LRR_RI_2: domain 1 of 8, from 726 to 752: score 0.1, E :

```
          *->npsLreLdLsnNkIgdeGaraLaeaLks<-*
             ++ L L++N+  d+  aL+e+L++
NBS1  726  HKTVTYLTLQGND-QDDMFPALCEVLRH  752
```

FIG. 8A

LRR_RI_2: domain 2 of 8, from 782 to 809: score 20.8, E = 0.031

```
          *->npsLreLdLsnNkIgdeGaraLaeaLks<-*
             n+sL    +Ls+N l deGa+ L  +L++
NBS1  782  NQSLICVNLSDNELLDEGAKLLYTTLRH  309
```

FIG. 8B

LRR_RI_2: domain 3 of 8, from 811 to 838: score 21.9, E = 0.016

```
          *->npsLreLdLsnNkIgdeGaraLaeaLks<-*
             L++L+L+n++l+++ ++ La++L
NBS1  811  KCFLQRLSLENCHLTEANCKDLAAVLVV  838
```

FIG. 8C

LRR_RI_2: domain 4 of 8, from 839 to 866: score 13.4, E = 0.56
*->npsLreLdLsnNklgdeGaraLaeaLks<-*
   ++ L  L L+ N++g   G++ L+e+L+
NBS1  839  SRELTHLCLAKNPIGNTGVKFLCEGLRY  866

FIG. 8D

LRR_RI_2: domain 5 of 8, from 868 to 895: score 17.0, E = 0.17
*->npsLreLdLsnNklgdeGaraLaeaLks<-*
   ++L++ L  L+n++++ +G+  L  ++L++
NBS1  868  ECKLQTLVLWNCDITSDGCCDLTKLLQE  895

FIG. 8E

LRR_RI_2: domain 6 of 8, from 896 to 923: score 22.6, E = 0.0091
*->npsLreLdLsnNklgdeGaraLaeaLks<-*
   ++sL+ LdL+ N++g  +G++ L+eaL+
NBS1  896  KSSLLCLDLGLNHIGVKGMKFLCEALRK  923

FIG. 8F

LRR_RI_2: domain 7 of 8, from 925 to 952: score 15.8, E = 0.26

```
          *->npsLreLdLsnNklgdeGaraLaeaLks<-*
             +++Lr L+L+++  +   +    L++aL+
NBS1   925   LCNLRCLWLWGCSIPPFSCEDLCSALSN   952
```

FIG. 8G

LRR_RI_2: domain 8 of 8, from 953 to 979: score 14.0, E = 0.47

```
          *->npsLreLdLsnNklgdeGaraLaeaLks<-*
             +sL  +LdL++ N+lg  +G++   L e+L+
NBS1   953   -QSLVTLDLGQNPLGSSGVKMLFETLTC   979
```

FIG. 8H

```
LRR: domain 1 of 9, from 740 to 767: score 10.9, E = 25
              *->nLeeLdLsnN.Lt....slppglfsnLp<-*         FIG. 10A
                 +L+eLdLs+N+L +++   +   +++++
      pyrin-1  740    SLTELDLSDNsLGdpgmRVLCETLQHPG    767

LRR: domain 2 of 9, from 769 to 796: score 2.3, E = 4.6e+02
              *->nLeeLdLsnN.Lt.....slppglfsnLp<-*
                 n+++L+L +++L+++     +++   ++s+ +      FIG. 10B
      pyrin-1  769    NIRRLWLGRCgLSheccfDISL-VLSSNQ   796

LRR: domain 3 of 9, from 797 to 821: score 9.7, E = 39
              *->nLeeLdLsnN.Lt..slppglfsnLp<-*         FIG. 10C
                 +L eLdLs+N L + ++    l+ +L+
      pyrin-1  797    KLVELDLSDNaLGdfGIRL-LCVGLK      821

LRR: domain 4 of 9, from 826 to 849: score 4.1, E = 2.5e+02
              *->nLeeLdLsnN.LtslppglfsnLp<-*
                 nL++L+L ++ Lts        +++            FIG. 10D
      pyrin-1  826    NLKKLWLVSCcLTSACCQDLASVL        849

LRR: domain 5 of 9, from 854 to 878: score 0.6, E = 8.2e+02
              *->nLeeLdLsnN.Lt..slppglfsnLp<-*
                 +L++L++   N L ++++    l+++ +         FIG. 10E
      pyrin-1  854    SLTRLYVGENaLGdsGVAI-LCEKAK      878

LRR: domain 6 of 9, from 883 to 906: score 5.1, E = 1.8e+02
              *->nLeeLdLsnN.LtslppglfsnLp<-*
                 nL++L  L n +Lts+   +++s+             FIG. 10F
      pyrin-1  883    NLQKLGLVNSgLTSVCCSALSSVL        906

LRR: domain 7 of 9, from 911 to 935: score 10.2, E = 32
              *->nLeeLdLsnN.Lt..slppglfsnLp<-*        FIG. 10G
                 nL++L+L++N+L ++++    l+++L
      pyrin-1  911    NLTHLYLRGNtLGdkGIKL-LCEGLL      935

LRR: domain 8 of 9, from 940 to 967: score 5.8, E = 1.4e+02
              *->nLeeLdLsnN.Lt.....slppglfsnLp<-*     FIG. 10H
                 +L++L L+n++Lt++     +l+  l+ + +
      pyrin-1  940    KLQVLELDNCnLTshccwDLST-LLTSSQ   967

LRR: domain 9 of 9, from 968 to 991: score 8.4, E = 59
              *->nLeeLdLsnN.LtslppglfsnLp<-*          FIG. 10I
                 +L++L+L  nN+L  +l      f+
      pyrin-1  968    SLRKLSLGNNdLGDLGVMMFCEVL        991
```

SEQUENCE LISTING

<160> NUMBER OF SEQ ID NOS: 13

<210> SEQ ID NO 1
<211> LENGTH: 3431
<212> TYPE: DNA
<213> ORGANISM: Homo sapiens

<400> SEQUENCE: 1

```
cagccctcat ctccgccggc gagtagggcc aggtgttggg agctcccacg tgggacaagg      60
tggtgtcttc ggcgcagatg ggtttcaacc tgcaggctct cctggagcag ctcagccagg     120
atgagttgag caagttcaag tatctgatca cgaccttctc cccggcacac gagctccaga     180
agatccccca caaggaggta gacaaggctg atgggaagca actggtagaa atcctcacca     240
cccattgtga cagctactgg gtggagatgg cgagcctcca ggtctttgaa aagatgcacc     300
gaatggatct gtctgagaga gcaaaggatg aagtcagaga agcagctttg aaatccttta     360
ataaaaggaa gcctctatca ttagggataa cacgaaagaa acgaccacct ctagacgtgg     420
acgaaatgct ggagcgcttc aaaacagaag cacaagacaa agacaatagg tgcaggtata     480
tattgaagac gaagttccgg gagatgtgga agagctggcc tggagatagc aaagaggtcc     540
aggttatggc tgagagatac aagatgctga tcccatttag caaccccagg gtgcttcccg     600
```

```
ggcccttctc atacacggtg gtgctgtatg gtcctgcagg ccttgggaaa accacgctgg      660
cccagaaact aatgctagac tgggcagagg acaacctcat ccacaaattc aaatatgcgt      720
tctacctcag ctgcagggag ctcagccgcc tgggcccgtg cagttttgca gagctggtct      780
tcagggactg gcctgaattg caggatgaca ttccacacat cctagcccaa gcacggaaaa      840
tcttgttcgt gattgacggc tttgatgagc tgggagccgc acctggggcg ctgatcgagg      900
acatctgcgg ggactgggag aagaagaagc cggtgcccgt cctcctgggg agtttgctga      960
acagggtgat gttacccaag gccgccctgc tggtcaccac gcggcccagg gccctgaggg     1020
acctccggat cctggcggag gagccgatct acataagggt ggagggcttc ctggaggagg     1080
acaagagggc ctatttcctg agacactttg agacgaggga ccaagccatg cgtgcctttg     1140
agctaatgag gagcaacgcg gccctgttcc agctgggctc ggcccccgcg gtgtgctgga     1200
tcgtgtgcac gactctgaag ctgcagatgg agaaggggga ggacccggtc cccacctgcc     1260
tcacccgcac ggggctgttc ctgcgtttcc tctgcagccg gttcccgcag ggcgcacagc     1320
tgcggggcgc gctgcggacg ctgagcctcc tggccgcgca gggcctgtgg gcgcagacgt     1380
ccgtgcttca ccgagaggat ctggaaaggc tcggggtgca ggagtccgac ctccgtctgt     1440
tcctggacgg agacatcctc cgccaggaca gagtctccaa aggctgctac tccttcatcc     1500
acctcagctt ccagcagttt ctcactgccc tgttctacac cctggagaag gaggaggaag     1560 aggatagggca cggccacacc tgggacattg ggacgtaca gaagctgctt tccggagtag     1620
aaagactcag gaaccccgac ctgatccaag caggctacta ctcctttggc ctcgctaacg     1680
agaagagagc caaggagttg gaggccactt ttggctgccg gatgtcaccg gacatcaaac     1740
aggaattgct gcgatgcgac ataagttgta agggtggaca ttcaacggtg acagacctgc     1800
aggagctcct cggctgtctg tacgagtctc aggaggagga gctggtgaag gaggtgatgg     1860
ctcagttcaa agaaatatcc ctgcacttaa atgcagtaga cgttgtgcca tcttcattct     1920
gcgtcaagca ctgtcgaaac ctgcagaaaa tgtcactgca ggtaataaag gagaatctcc     1980
cggagaatgt cactgcgtct gaatcagacg ccgaggttga gagatcccag gatgatcagc     2040
acatgcttcc tttctggacg gacctttgtt ccatatttgg atcaaataag gatctgatgg     2100
gtctagcaat caatgatagc tttctcagtg cctccctagt aaggatcctg tgtgaacaaa     2160
tagcctctga cacctgtcat ctccagagag tggtgttcaa aaacatttcc ccagctgatg     2220
ctcatcggaa cctctgccta gctcttcgag gtcacaagac tgtaacgtat ctgacccttc     2280
aaggcaatga ccaggatgat atgtttcccg cattgtgtga ggtcttgaga catccagaat     2340
gtaacctgcg atatctcggg ttggtgtctt gttccgctac cactcagcag tgggctgatc     2400
tctccttggc ccttgaagtc aaccagtccc tgacgtgcgt aaacctctcc gacaatgagc     2460
ttctggatga gggtgctaag ttgctgtaca caactttgag acaccccaag tgctttctgc     2520
agaggttgtc gttggaaaac tgtcaccttca gaagccaa ttgcaggac cttgctgctg     2580 tgttggttgt cagccgggag ctgacacacc tgtgcttggc caagaacccc attgggaata     2640
caggggtgaa gtttctgtgt gagggcttga ggtaccccga gtgtaaactg cagaccttgg     2700
tgctttggaa ctgcgacata actagcgatg gctgctgcga tctcacaaag cttctccaag     2760
aaaaatcaag cctgttgtgt ttggatctgg ggctgaatca cataggagtt aagggaatga     2820
agttcctgtg tgaggctttg aggaaaccac tgtgcaactt gagatgtctg tggttgtggg     2880
gatgttccat ccctccgttc agttgtgaag acctctgctc tgccctcagc aaccagagcc     2940
tcgtcactct ggacctgggt cagaatccct tggggtctag tggagtgaag atgctgtttg     3000
```

```
aaaccttgac atgttccagt ggcaccctcc ggacactcag gttgaaaatc gatgacttta    3060
atgatgaact caataagctg ctggaagaaa tagaagaaaa aaacccacaa ctgattattg    3120
atactgagaa acatcatccc tgggcagaaa ggccttcttc tcatgacttc atgatctgaa    3180 tcccccgag tcattcattc tccatgaagt catcgatttt ccaggtgttg gtgaactgcc     3240
tgtgactcct ctcctccccg gcccctaccc ctcagggata atgagttcat tgctgggcta    3300
gatgttttag ccatgattct gcctctgttt tatacctgca cacatcctta tctttgttac    3360
atatgaaata tctgtatcac gggtatattg agagaaataa aggtgagagc attcacaaaa    3420
aaaaaaaaaa a                                                         3431
```

<210> SEQ ID NO 2
<211> LENGTH: 1033
<212> TYPE: PRT
<213> ORGANISM: Homo sapiens

<400> SEQUENCE: 2

```
Met Gly Phe Asn Leu Gln Ala Leu Leu Glu Gln Leu Ser Gln Asp Glu
 1               5                  10                  15

Leu Ser Lys Phe Lys Tyr Leu Ile Thr Thr Phe Ser Pro Ala His Glu
            20                  25                  30

Leu Gln Lys Ile Pro His Lys Glu Val Asp Lys Ala Asp Gly Lys Gln
        35                  40                  45

Leu Val Glu Ile Leu Thr Thr His Cys Asp Ser Tyr Trp Val Glu Met
    50                  55                  60

Ala Ser Leu Gln Val Phe Glu Lys Met His Arg Met Asp Leu Ser Glu
65                  70                  75                  80

Arg Ala Lys Asp Glu Val Arg Glu Ala Ala Leu Lys Ser Phe Asn Lys
                85                  90                  95

Arg Lys Pro Leu Ser Leu Gly Ile Thr Arg Lys Glu Arg Pro Pro Leu
            100                 105                 110

Asp Val Asp Glu Met Leu Glu Arg Phe Lys Thr Glu Ala Gln Asp Lys
        115                 120                 125

Asp Asn Arg Cys Arg Tyr Ile Leu Lys Thr Lys Phe Arg Glu Met Trp
    130                 135                 140

Lys Ser Trp Pro Gly Asp Ser Lys Glu Val Gln Val Met Ala Glu Arg
145                 150                 155                 160

Tyr Lys Met Leu Ile Pro Phe Ser Asn Pro Arg Val Leu Pro Gly Pro
                165                 170                 175

Phe Ser Tyr Thr Val Val Leu Tyr Gly Pro Ala Gly Leu Gly Lys Thr
            180                 185                 190

Thr Leu Ala Gln Lys Leu Met Leu Asp Trp Ala Glu Asp Asn Leu Ile
        195                 200                 205

His Lys Phe Lys Tyr Ala Phe Tyr Leu Ser Cys Arg Glu Leu Ser Arg
    210                 215                 220

Leu Gly Pro Cys Ser Phe Ala Glu Leu Val Phe Arg Asp Trp Pro Glu
225                 230                 235                 240

Leu Gln Asp Asp Ile Pro His Ile Leu Ala Gln Ala Arg Lys Ile Leu
                245                 250                 255

Phe Val Ile Asp Gly Phe Asp Glu Leu Gly Ala Ala Pro Gly Ala Leu
            260                 265                 270

Ile Glu Asp Ile Cys Gly Asp Trp Glu Lys Lys Lys Pro Val Pro Val
        275                 280                 285
```

-continued

```
Leu Leu Gly Ser Leu Leu Asn Arg Val Met Leu Pro Lys Ala Ala Leu
    290                 295                 300
Leu Val Thr Thr Arg Pro Arg Ala Leu Arg Asp Leu Arg Ile Leu Ala
305                 310                 315                 320
Glu Glu Pro Ile Tyr Ile Arg Val Glu Gly Phe Leu Glu Glu Asp Lys
                325                 330                 335
Arg Ala Tyr Phe Leu Arg His Phe Gly Asp Glu Asp Gln Ala Met Arg
            340                 345                 350
Ala Phe Glu Leu Met Arg Ser Asn Ala Ala Leu Phe Gln Leu Gly Ser
        355                 360                 365
Ala Pro Ala Val Cys Trp Ile Val Cys Thr Thr Leu Lys Leu Gln Met
370                 375                 380
Glu Lys Gly Glu Asp Pro Val Pro Thr Cys Leu Thr Arg Thr Gly Leu
385                 390                 395                 400
Phe Leu Arg Phe Leu Cys Ser Arg Phe Pro Gln Gly Ala Gln Leu Arg
                405                 410                 415
Gly Ala Leu Arg Thr Leu Ser Leu Leu Ala Ala Gln Gly Leu Trp Ala
            420                 425                 430
Gln Thr Ser Val Leu His Arg Glu Asp Leu Glu Arg Leu Gly Val Gln
        435                 440                 445
Glu Ser Asp Leu Arg Leu Phe Leu Asp Gly Asp Ile Leu Arg Gln Asp
450                 455                 460
Arg Val Ser Lys Gly Cys Tyr Ser Phe Ile His Leu Ser Phe Gln Gln
465                 470                 475                 480
Phe Leu Thr Ala Leu Phe Tyr Thr Leu Glu Lys Glu Glu Glu Glu Asp
                485                 490                 495
Arg Asp Gly His Thr Trp Asp Ile Gly Asp Val Gln Lys Leu Leu Ser
            500                 505                 510
Gly Val Glu Arg Leu Arg Asn Pro Asp Leu Ile Gln Ala Gly Tyr Tyr
        515                 520                 525
Ser Phe Gly Leu Ala Asn Glu Lys Arg Ala Lys Glu Leu Glu Ala Thr
530                 535                 540
Phe Gly Cys Arg Met Ser Pro Asp Ile Lys Gln Glu Leu Leu Arg Cys
545                 550                 555                 560
Asp Ile Ser Cys Lys Gly Gly His Ser Thr Val Thr Asp Leu Gln Glu
                565                 570                 575
Leu Leu Gly Cys Leu Tyr Glu Ser Gln Glu Glu Leu Val Lys Glu
            580                 585                 590
Val Met Ala Gln Phe Lys Glu Ile Ser Leu His Leu Asn Ala Val Asp
        595                 600                 605
Val Val Pro Ser Ser Phe Cys Val Lys His Cys Arg Asn Leu Gln Lys
610                 615                 620
Met Ser Leu Gln Val Ile Lys Glu Asn Leu Pro Glu Asn Val Thr Ala
625                 630                 635                 640
Ser Glu Ser Asp Ala Glu Val Glu Arg Ser Gln Asp Gln His Met
                645                 650                 655
Leu Pro Phe Trp Thr Asp Leu Cys Ser Ile Phe Gly Ser Asn Lys Asp
            660                 665                 670
Leu Met Gly Leu Ala Ile Asn Asp Ser Phe Leu Ser Ala Ser Leu Val
        675                 680                 685
Arg Ile Leu Cys Glu Gln Ile Ala Ser Asp Thr Cys His Leu Gln Arg
690                 695                 700
Val Val Phe Lys Asn Ile Ser Pro Ala Asp Ala His Arg Asn Leu Cys
```

```
                705                 710                 715                 720
Leu Ala Leu Arg Gly His Lys Thr Val Thr Tyr Leu Thr Leu Gln Gly
                    725                 730                 735
Asn Asp Gln Asp Asp Met Phe Pro Ala Leu Cys Glu Val Leu Arg His
                740                 745                 750
Pro Glu Cys Asn Leu Arg Tyr Leu Gly Leu Val Ser Cys Ser Ala Thr
            755                 760                 765
Thr Gln Gln Trp Ala Asp Leu Ser Leu Ala Leu Glu Val Asn Gln Ser
        770                 775                 780
Leu Thr Cys Val Asn Leu Ser Asp Asn Glu Leu Leu Asp Glu Gly Ala
785                 790                 795                 800
Lys Leu Leu Tyr Thr Thr Leu Arg His Pro Lys Cys Phe Leu Gln Arg
                805                 810                 815
Leu Ser Leu Glu Asn Cys His Leu Thr Glu Ala Asn Cys Lys Asp Leu
            820                 825                 830
Ala Ala Val Leu Val Ser Arg Glu Leu Thr His Leu Cys Leu Ala
        835                 840                 845
Lys Asn Pro Ile Gly Asn Thr Gly Val Lys Phe Leu Cys Glu Gly Leu
850                 855                 860
Arg Tyr Pro Glu Cys Lys Leu Gln Thr Leu Val Leu Trp Asn Cys Asp
865                 870                 875                 880
Ile Thr Ser Asp Gly Cys Cys Asp Leu Thr Lys Leu Leu Gln Glu Lys
                885                 890                 895
Ser Ser Leu Leu Cys Leu Asp Leu Gly Leu Asn His Ile Gly Val Lys
                900                 905                 910
Gly Met Lys Phe Leu Cys Glu Ala Leu Arg Lys Pro Leu Cys Asn Leu
            915                 920                 925
Arg Cys Leu Trp Leu Trp Gly Cys Ser Ile Pro Pro Phe Ser Cys Glu
        930                 935                 940
Asp Leu Cys Ser Ala Leu Ser Asn Gln Ser Leu Val Thr Leu Asp Leu
945                 950                 955                 960
Gly Gln Asn Pro Leu Gly Ser Ser Gly Val Lys Met Leu Phe Glu Thr
                965                 970                 975
Leu Thr Cys Ser Ser Gly Thr Leu Arg Thr Leu Arg Leu Lys Ile Asp
                980                 985                 990
Asp Phe Asn Asp Glu Leu Asn Lys Leu Leu Glu Glu Ile Glu Glu Lys
            995                 1000                1005
Asn Pro Gln Leu Ile Ile Asp Thr Glu Lys His His Pro Trp Ala Glu
        1010                1015                1020
Arg Pro Ser Ser His Asp Phe Met Ile
1025                1030

<210> SEQ ID NO 3
<211> LENGTH: 3099
<212> TYPE: DNA
<213> ORGANISM: Homo sapiens
<220> FEATURE:
<221> NAME/KEY: CDS
<222> LOCATION: (1)...(3099)

<400> SEQUENCE: 3 atg ggt ttc aac ctg cag gct ctc ctg gag cag ctc agc cag gat gag       48
Met Gly Phe Asn Leu Gln Ala Leu Leu Glu Gln Leu Ser Gln Asp Glu
 1               5                  10                  15 ttg agc aag ttc aag tat ctg atc acg acc ttc tcc ccg gca cac gag       96
Leu Ser Lys Phe Lys Tyr Leu Ile Thr Thr Phe Ser Pro Ala His Glu
```

-continued

```
            20                  25                  30
ctc cag aag atc ccc cac aag gag gta gac aag gct gat ggg aag caa      144
Leu Gln Lys Ile Pro His Lys Glu Val Asp Lys Ala Asp Gly Lys Gln
         35                  40                  45 ctg gta gaa atc ctc acc acc cat tgt gac agc tac tgg gtg gag atg      192
Leu Val Glu Ile Leu Thr Thr His Cys Asp Ser Tyr Trp Val Glu Met
 50                  55                  60 gcg agc ctc cag gtc ttt gaa aag atg cac cga atg gat ctg tct gag      240
Ala Ser Leu Gln Val Phe Glu Lys Met His Arg Met Asp Leu Ser Glu
 65                  70                  75                  80 aga gca aag gat gaa gtc aga gaa gca gct ttg aaa tcc ttt aat aaa      288
Arg Ala Lys Asp Glu Val Arg Glu Ala Ala Leu Lys Ser Phe Asn Lys
                 85                  90                  95 agg aag cct cta tca tta ggg ata aca cgg aaa gaa cga cca cct cta      336
Arg Lys Pro Leu Ser Leu Gly Ile Thr Arg Lys Glu Arg Pro Pro Leu
             100                 105                 110 gac gtg gac gaa atg ctg gag cgc ttc aaa aca gaa gca caa gac aaa      384
Asp Val Asp Glu Met Leu Glu Arg Phe Lys Thr Glu Ala Gln Asp Lys
         115                 120                 125 gac aat agg tgc agg tat ata ttg aag acg aag ttc cgg gag atg tgg      432
Asp Asn Arg Cys Arg Tyr Ile Leu Lys Thr Lys Phe Arg Glu Met Trp
130                 135                 140 aag agc tgg cct gga gat agc aaa gag gtc cag gtt atg gct gag aga      480
Lys Ser Trp Pro Gly Asp Ser Lys Glu Val Gln Val Met Ala Glu Arg
145                 150                 155                 160 tac aag atg ctg atc cca ttt agc aac ccc agg gtg ctt ccc ggg ccc      528
Tyr Lys Met Leu Ile Pro Phe Ser Asn Pro Arg Val Leu Pro Gly Pro
                 165                 170                 175 ttc tca tac acg gtg gtg ctg tat ggt cct gca ggc ttg ggg aaa acc      576
Phe Ser Tyr Thr Val Val Leu Tyr Gly Pro Ala Gly Leu Gly Lys Thr
             180                 185                 190 acg ctg gcc cag aaa cta atg cta gac tgg gca gag gac aac ctc atc      624
Thr Leu Ala Gln Lys Leu Met Leu Asp Trp Ala Glu Asp Asn Leu Ile
         195                 200                 205 cac aaa ttc aaa tat gcg ttc tac ctc agc tgc agg gag ctc agc cgc      672
His Lys Phe Lys Tyr Ala Phe Tyr Leu Ser Cys Arg Glu Leu Ser Arg
     210                 215                 220 ctg ggc ccg tgc agt ttt gca gag ctg gtc ttc agg gac tgg cct gaa      720
Leu Gly Pro Cys Ser Phe Ala Glu Leu Val Phe Arg Asp Trp Pro Glu
225                 230                 235                 240 ttg cag gat gac att cca cac atc cta gcc caa gca cgg aaa atc ttg      768
Leu Gln Asp Asp Ile Pro His Ile Leu Ala Gln Ala Arg Lys Ile Leu
                 245                 250                 255 ttc gtg att gac ggc ttt gat gag ctg gga gcc gca cct ggg gcg ctg      816
Phe Val Ile Asp Gly Phe Asp Glu Leu Gly Ala Ala Pro Gly Ala Leu
             260                 265                 270 atc gag gac atc tgc ggg gac tgg gag aag aag aag ccg gtg ccc gtc      864
Ile Glu Asp Ile Cys Gly Asp Trp Glu Lys Lys Lys Pro Val Pro Val
         275                 280                 285 ctc ctg ggg agt ttg ctg aac agg gtg atg tta ccc aag gcc gcc ctg      912
Leu Leu Gly Ser Leu Leu Asn Arg Val Met Leu Pro Lys Ala Ala Leu
     290                 295                 300 ctg gtc acc acg cgg ccc agg gcc ctg agg gac ctc cgg atc ctg gcg      960
Leu Val Thr Thr Arg Pro Arg Ala Leu Arg Asp Leu Arg Ile Leu Ala
305                 310                 315                 320 gag gag ccg atc tac ata agg gtg gag ggc ttc ctg gag gag gac aag     1008
Glu Glu Pro Ile Tyr Ile Arg Val Glu Gly Phe Leu Glu Glu Asp Lys
                 325                 330                 335 agg gcc tat ttc ctg aga cac ttt gga gac gag gac caa gcc atg cgt     1056
```

```
                Arg Ala Tyr Phe Leu Arg His Phe Gly Asp Glu Asp Gln Ala Met Arg
                                340                 345                 350 gcc ttt gag cta atg agg agc aac gcg gcc ctg ttc cag ctg ggc tcg         1104
Ala Phe Glu Leu Met Arg Ser Asn Ala Ala Leu Phe Gln Leu Gly Ser
            355                 360                 365 gcc ccc gcg gtg tgc tgg atc gtg tgc acg act ctg aag ctg cag atg         1152
Ala Pro Ala Val Cys Trp Ile Val Cys Thr Thr Leu Lys Leu Gln Met
370                 375                 380 gag aag ggg gag gac ccg gtc ccc acc tgc ctc acc cgc acg ggg ctg         1200
Glu Lys Gly Glu Asp Pro Val Pro Thr Cys Leu Thr Arg Thr Gly Leu
385                 390                 395                 400 ttc ctg cgt ttc ctc tgc agc cgg ttc ccg cag ggc gca cag ctg cgg         1248
Phe Leu Arg Phe Leu Cys Ser Arg Phe Pro Gln Gly Ala Gln Leu Arg
                405                 410                 415 ggc gcg ctg cgg acg ctg agc ctc ctg gcc gcg cag ggc ctg tgg gcg         1296
Gly Ala Leu Arg Thr Leu Ser Leu Leu Ala Ala Gln Gly Leu Trp Ala
            420                 425                 430 cag acg tcc gtg ctt cac cga gag gat ctg gaa agg ctc ggg gtg cag         1344
Gln Thr Ser Val Leu His Arg Glu Asp Leu Glu Arg Leu Gly Val Gln
        435                 440                 445 gag tcc gac ctc cgt ctg ttc ctg gac gga gac atc ctc cgc cag gac         1392
Glu Ser Asp Leu Arg Leu Phe Leu Asp Gly Asp Ile Leu Arg Gln Asp
    450                 455                 460 aga gtc tcc aaa ggc tgc tac tcc ttc atc cac ctc agc ttc cag cag         1440
Arg Val Ser Lys Gly Cys Tyr Ser Phe Ile His Leu Ser Phe Gln Gln
465                 470                 475                 480 ttt ctc act gcc ctg ttc tac acc ctg gag aag gag gag gaa gag gat         1488
Phe Leu Thr Ala Leu Phe Tyr Thr Leu Glu Lys Glu Glu Glu Glu Asp
                485                 490                 495 agg gac ggc cac acc tgg gac att ggg gac gta cag aag ctg ctt tcc         1536
Arg Asp Gly His Thr Trp Asp Ile Gly Asp Val Gln Lys Leu Leu Ser
            500                 505                 510 gga gta gaa aga ctc agg aac ccc gac ctg atc caa gca ggc tac tac         1584
Gly Val Glu Arg Leu Arg Asn Pro Asp Leu Ile Gln Ala Gly Tyr Tyr
        515                 520                 525 tcc ttt ggc ctc gct aac gag aag aga gcc aag gag ttg gag gcc act         1632
Ser Phe Gly Leu Ala Asn Glu Lys Arg Ala Lys Glu Leu Glu Ala Thr
    530                 535                 540 ttt ggc tgc cgg atg tca ccg gac atc aaa cag gaa ttg ctg cga tgc         1680
Phe Gly Cys Arg Met Ser Pro Asp Ile Lys Gln Glu Leu Leu Arg Cys
545                 550                 555                 560 gac ata agt tgt aag ggt gga cat tca acg gtg aca gac ctg cag gag         1728
Asp Ile Ser Cys Lys Gly Gly His Ser Thr Val Thr Asp Leu Gln Glu
                565                 570                 575 ctc ctc ggc tgt ctg tac gag tct cag gag gag gag ctg gtg aag gag         1776
Leu Leu Gly Cys Leu Tyr Glu Ser Gln Glu Glu Glu Leu Val Lys Glu
            580                 585                 590 gtg atg gct cag ttc aaa gaa ata tcc ctg cac tta aat gca gta gac         1824
Val Met Ala Gln Phe Lys Glu Ile Ser Leu His Leu Asn Ala Val Asp
        595                 600                 605 gtt gtg cca tct tca ttc tgc gtc aag cac tgt cga aac ctg cag aaa         1872
Val Val Pro Ser Ser Phe Cys Val Lys His Cys Arg Asn Leu Gln Lys
    610                 615                 620 atg tca ctg cag gta ata aag gag aat ctc ccg gag aat gtc act gcg         1920
Met Ser Leu Gln Val Ile Lys Glu Asn Leu Pro Glu Asn Val Thr Ala
625                 630                 635                 640 tct gaa tca gac gcc gag gtt gag aga tcc cag gat gat cag cac atg         1968
Ser Glu Ser Asp Ala Glu Val Glu Arg Ser Gln Asp Asp Gln His Met
                645                 650                 655
```

```
ctt cct ttc tgg acg gac ctt tgt tcc ata ttt gga tca aat aag gat         2016
Leu Pro Phe Trp Thr Asp Leu Cys Ser Ile Phe Gly Ser Asn Lys Asp
            660                 665                 670 ctg atg ggt cta gca atc aat gat agc ttt ctc agt gcc tcc cta gta         2064
Leu Met Gly Leu Ala Ile Asn Asp Ser Phe Leu Ser Ala Ser Leu Val
        675                 680                 685 agg atc ctg tgt gaa caa ata gcc tct gac acc tgt cat ctc cag aga         2112
Arg Ile Leu Cys Glu Gln Ile Ala Ser Asp Thr Cys His Leu Gln Arg
    690                 695                 700 gtg gtg ttc aaa aac att tcc cca gct gat gct cat cgg aac ctc tgc         2160
Val Val Phe Lys Asn Ile Ser Pro Ala Asp Ala His Arg Asn Leu Cys
705                 710                 715                 720 cta gct ctt cga ggt cac aag act gta acg tat ctg acc ctt caa ggc         2208
Leu Ala Leu Arg Gly His Lys Thr Val Thr Tyr Leu Thr Leu Gln Gly
                725                 730                 735 aat gac cag gat gat atg ttt ccc gca ttg tgt gag gtc ttg aga cat         2256
Asn Asp Gln Asp Asp Met Phe Pro Ala Leu Cys Glu Val Leu Arg His
            740                 745                 750 cca gaa tgt aac ctg cga tat ctc ggg ttg gtg tct tgt tcc gct acc         2304
Pro Glu Cys Asn Leu Arg Tyr Leu Gly Leu Val Ser Cys Ser Ala Thr
        755                 760                 765 act cag cag tgg gct gat ctc tcc ttg gcc ctt gaa gtc aac cag tcc         2352
Thr Gln Gln Trp Ala Asp Leu Ser Leu Ala Leu Glu Val Asn Gln Ser
    770                 775                 780 ctg acg tgc gta aac ctc tcc gac aat gag ctt ctg gat gag ggt gct         2400
Leu Thr Cys Val Asn Leu Ser Asp Asn Glu Leu Leu Asp Glu Gly Ala
785                 790                 795                 800 aag ttg ctg tac aca act ttg aga cac ccc aag tgc ttt ctg cag agg         2448
Lys Leu Leu Tyr Thr Thr Leu Arg His Pro Lys Cys Phe Leu Gln Arg
                805                 810                 815 ttg tcg ttg gaa aac tgt cac ctt aca gaa gcc aat tgc aag gac ctt         2496
Leu Ser Leu Glu Asn Cys His Leu Thr Glu Ala Asn Cys Lys Asp Leu
            820                 825                 830 gct gct gtg ttg gtt gtc agc cgg gag ctg aca cac ctg tgc ttg gcc         2544
Ala Ala Val Leu Val Val Ser Arg Glu Leu Thr His Leu Cys Leu Ala
        835                 840                 845 aag aac ccc att ggg aat aca ggg gtg aag ttt ctg tgt gag ggc ttg         2592
Lys Asn Pro Ile Gly Asn Thr Gly Val Lys Phe Leu Cys Glu Gly Leu
    850                 855                 860 agg tac ccc gag tgt aaa ctg cag acc ttg gtg ctt tgg aac tgc gac         2640
Arg Tyr Pro Glu Cys Lys Leu Gln Thr Leu Val Leu Trp Asn Cys Asp
865                 870                 875                 880 ata act agc gat ggc tgc tgc gat ctc aca aag ctt ctc caa gaa aaa         2688
Ile Thr Ser Asp Gly Cys Cys Asp Leu Thr Lys Leu Leu Gln Glu Lys
                885                 890                 895 tca agc ctg ttg tgt ttg gat ctg ggg ctg aat cac ata gga gtt aag         2736
Ser Ser Leu Leu Cys Leu Asp Leu Gly Leu Asn His Ile Gly Val Lys
            900                 905                 910 gga atg aag ttc ctg tgt gag gct ttg agg aaa cca ctg tgc aac ttg         2784
Gly Met Lys Phe Leu Cys Glu Ala Leu Arg Lys Pro Leu Cys Asn Leu
        915                 920                 925 aga tgt ctg tgg ttg tgg gga tgt tcc atc cct ccg ttc agt tgt gaa         2832
Arg Cys Leu Trp Leu Trp Gly Cys Ser Ile Pro Pro Phe Ser Cys Glu
    930                 935                 940 gac ctc tgc tct gcc ctc agc aac cag agc ctc gtc act ctg gac ctg         2880
Asp Leu Cys Ser Ala Leu Ser Asn Gln Ser Leu Val Thr Leu Asp Leu
945                 950                 955                 960 ggt cag aat ccc ttg ggg tct agt gga gtg aag atg ctg ttt gaa acc         2928
Gly Gln Asn Pro Leu Gly Ser Ser Gly Val Lys Met Leu Phe Glu Thr
                965                 970                 975
```

| ttg aca tgt tcc agt ggc acc ctc cgg aca ctc agg ttg aaa atc gat | 2976 |
|---|---|
| Leu Thr Cys Ser Ser Gly Thr Leu Arg Thr Leu Arg Leu Lys Ile Asp | |
|         980                 985                990 | |
| gac ttt aat gat gaa ctc aat aag ctg ctg gaa gaa ata gaa gaa aaa | 3024 |
| Asp Phe Asn Asp Glu Leu Asn Lys Leu Leu Glu Glu Ile Glu Glu Lys | |
|         995              1000              1005 | |
| aac cca caa ctg att att gat act gag aaa cat cat ccc tgg gca gaa | 3072 |
| Asn Pro Gln Leu Ile Ile Asp Thr Glu Lys His His Pro Trp Ala Glu | |
|    1010                1015              1020 | |
| agg cct tct tct cat gac ttc atg atc | 3099 |
| Arg Pro Ser Ser His Asp Phe Met Ile | |
| 1025              1030 | |

<210> SEQ ID NO 4
<211> LENGTH: 3857
<212> TYPE: DNA
<213> ORGANISM: Homo sapiens

<400> SEQUENCE: 4

| ccacgcgtcc gcccacgcgt ccgggcatct ggggaaacct ttcttccatg gctcaggaca | 60 |
|---|---|
| cactcctgga tcgagccaac aggagaactt tctgtgtgga ccgaagccta aggaccctga | 120 |
| aaacagctgc agatgaagat ggcaagcacc cgctgcaagc tggccaggta cctggaggac | 180 |
| ctggaggatg tggacttgaa gaaatttaag atgcacttag aggactatcc tccccagaag | 240 |
| ggctgcatcc ccctcccgag gggtcagaca gagaaggcag accatgtgga tctagccacg | 300 |
| ctaatgatcg acttcaatgg ggaggagaag gcgtgggcca tggccgtgtg gatcttcgct | 360 |
| gcgatcaaca ggagagacct ttatgagaaa gcaaaaagag atgagccgaa gtggggttca | 420 |
| gataatgcac gtgtttcgaa tcccactgtg atatgccagg aagacagcat tgaagaggag | 480 |
| tggatgggtt tactggagta cctttcgaga atctctattt gtaaaatgaa gaaagattac | 540 |
| cgtaagaagt acagaaagta cgtgagaagc agattccagt gcattgaaga caggaatgcc | 600 |
| cgtctgggtg agagtgtgag cctcaacaaa cgctacacac gactgcgtct catcaaggag | 660 |
| caccggagcc agcaggagag ggagcaggag cttctggcca tcggcaagac caagacgtgt | 720 |
| gagagccccg tgagtcccat taagatggag ttgctgtttg accccgatga tgagcattct | 780 |
| gagcctgtgc acaccgtggt gttccagggg gcggcaggga ttgggaaaac aatcctggcc | 840 |
| aggaagatga tgttggactg gcatcgggg acactctacc aagacaggtt tgactatctg | 900 |
| ttctatatcc actgtcggga ggtgagcctt gtgacacaga ggagcctggg ggacctgatc | 960 |
| atgagctgct gccccgaccc aaacccaccc atccacaaga tcgtgagaaa accctccaga | 1020 |
| atcctcttcc tcatggacgg cttcgatgag ctgcaaggtg cctttgacga gcacatagga | 1080 |
| ccgctctgca ctgactggca aaggccgag cggggagaca ttctcctgag cagcctcatc | 1140 |
| agaaagaagc tgcttcccga ggcctctctg ctcatcacca cgagacctgt ggccctggag | 1200 |
| aaactgcagc acttgctgga ccatcctcgg catgtggaga tcctgggttt ctccgaggcc | 1260 |
| aaaaggaaag agtacttctt caagtacttc tctgatgagg cccaagccag ggcagccttc | 1320 |
| agtctgattc aggagaacga ggtcctcttc accatgtgct tcatccccct ggtctgctgg | 1380 |
| atcgtgtgca ctggactgaa acagcagatg gagagtggca gagccttgc ccagacatct | 1440 |
| aagaccacca ccgcggtgta cgtcttcttc ctttccagtt tgctgcagcc ccggggaggg | 1500 |
| agccaggagc acggcctctg cgcccacctc tgggggctct gctctttggc tgcagatgga | 1560 |
| atctggaacc agaaaatcct gtttgaggag tccgacctca ggaatcatgg actgcagaag | 1620 |

-continued

```
gcggatgtgt ctgctttcct gaggatgaac ctgttccaaa aggaagtgga ctgcgagaag    1680
ttctacagct tcatccacat gactttccag gagttctttg ccgccatgta ctacctgctg    1740
gaagaggaaa aggaaggaag gacgaacgtt ccagggagtc gtttgaagct tcccagccga    1800
gacgtgacag tccttctgga aaactatggc aaattcgaaa aggggtattt gattttttgtt   1860
gtacgtttcc tctttggcct ggtaaaccag gagaggacct cctacttgga agaaaatta    1920
agttgcaaga tctctcagca aatcaggctg gagctgctga aatggattga agtgaaagcc    1980
aaagctaaaa agctgcagat ccagcccagc cagctggaat tgttctactg tttgtacgag    2040
atgcaggagg aggacttcgt gcaaagggcc atggactatt cccccaagat tgagatcaat    2100
ctctccacca gaatggacca catggttttct tccttttgca ttgagaactg tcatcgggtg   2160
gagtcactgt ccctggggtt tctccataac atgcccaagg aggaagagga ggaggaaaag    2220
gaaggccgac accttgatat ggtgcagtgt gtcctcccaa gctcctctca tgctgcctgt    2280
tctcatggat tggtgaacag ccacctcact tccagttttt gccggggcct cttttcagtt    2340
ctgagcacca gccagagtct aactgaattg gacctcagtg acaattctct gggggaccca    2400
gggatgagag tgttgtgtga aacgctccag catcctggct gtaacattcg gagattgtgg    2460
ttggggcgct gtggcctctc gcatgagtgc tgcttcgaca tctccttggt cctcagcagc    2520
aaccagaagc tggtggagct ggacctgagt gacaacgccc tcggtgactt cggaatcaga    2580
cttctgtgtg tgggactgaa gcacctgttg tgcaatctga agaagctctg gttggtcagc    2640
tgctgcctca catcagcatg ttgtcaggat cttgcatcag tattgagcac cagccattcc    2700
ctgaccagac tctatgtggg ggagaatgcc ttgggagact caggagtcgc aattttatgt    2760
gaaaaagcca agaatccaca gtgtaacctg cagaaactgg ggttggtgaa ttctggcctt    2820
acgtcagtct gttgttcagc tttgtcctcg gtactcagca ctaatcagaa tctcacgcac    2880
cttttacctgc gaggcaacac tctcggagac aagggggatca aactactctg tgagggactc    2940
ttgcaccccg actgcaagct tcaggtgttg gaattagaca actgcaacct cacgtcacac    3000
tgctgctggg atctttccac acttctgacc tccagccaga gcctgcgaaa gctgagcctg    3060
ggcaacaatg acctgggcga cctgggggtc atgatgttct gtgaagtgct gaaacagcag    3120
agctgcctcc tgcagaacct ggggttgtct gaaatgtatt tcaattatga gacaaaaagt    3180
gcgttagaaa cacttcaaga agaaaagcct gagctgaccg tcgtctttga gccttcttgg    3240
taggagtgga aacggggctg ccagacgcca gtgttctccg gtccctccag ctgggggccc    3300
tcaggtggag agagctgcga tccatccagg ccaagaccac agctctgtga tccttccggt    3360
ggagtgtcgg agaagagagc ttgccgacga tgccttcctg tgcagagctt gggcatctcc    3420
tttacgccag ggtgaggaag acaccaggac aatgacagca tcgggtgttg ttctcatcac    3480
agcgcctcag ttagaggatg ttcctcttgg tgacctcatg taattagctc attcaataaa    3540
gcactttctt tatttttctc ttctctgtct aactttcttt ttcctatctt tttttcttct    3600
ttgttctgtt tactttttgct catatcatca ttcccgctaa ctttctatta actgaccata    3660
acacagaact agttgactat atattatgtt gaaattttat ggcagctatt tatttattta    3720
aattttttgt aatagtttttg ttttctaata agaaaaatcc atgcttttttg tagctggttg   3780
aaaattcagg aatatgtaaa acttttttggt atttaattaa attgattcct tttcttaatt    3840
ttaaaaaaaa aaaaaaa                                                    3857
```

<210> SEQ ID NO 5
<211> LENGTH: 1034

```
<212> TYPE: PRT
<213> ORGANISM: Homo sapiens

<400> SEQUENCE: 5

Met Ala Ser Thr Arg Cys Lys Leu Ala Arg Tyr Leu Glu Asp Leu Glu
 1               5                  10                  15

Asp Val Asp Leu Lys Lys Phe Lys Met His Leu Glu Asp Tyr Pro Pro
                20                  25                  30

Gln Lys Gly Cys Ile Pro Leu Pro Arg Gly Gln Thr Glu Lys Ala Asp
            35                  40                  45

His Val Asp Leu Ala Thr Leu Met Ile Asp Phe Asn Gly Glu Glu Lys
    50                  55                  60

Ala Trp Ala Met Ala Val Trp Ile Phe Ala Ala Ile Asn Arg Arg Asp
65                  70                  75                  80

Leu Tyr Glu Lys Ala Lys Arg Asp Glu Pro Lys Trp Gly Ser Asp Asn
                85                  90                  95

Ala Arg Val Ser Asn Pro Thr Val Ile Cys Gln Glu Asp Ser Ile Glu
            100                 105                 110

Glu Glu Trp Met Gly Leu Leu Glu Tyr Leu Ser Arg Ile Ser Ile Cys
        115                 120                 125

Lys Met Lys Lys Asp Tyr Arg Lys Lys Tyr Arg Lys Tyr Val Arg Ser
    130                 135                 140

Arg Phe Gln Cys Ile Glu Asp Arg Asn Ala Arg Leu Gly Glu Ser Val
145                 150                 155                 160

Ser Leu Asn Lys Arg Tyr Thr Arg Leu Arg Leu Ile Lys Glu His Arg
                165                 170                 175

Ser Gln Gln Glu Arg Glu Gln Glu Leu Leu Ala Ile Gly Lys Thr Lys
            180                 185                 190

Thr Cys Glu Ser Pro Val Ser Pro Ile Lys Met Glu Leu Leu Phe Asp
        195                 200                 205

Pro Asp Asp Glu His Ser Glu Pro Val His Thr Val Val Phe Gln Gly
    210                 215                 220

Ala Ala Gly Ile Gly Lys Thr Ile Leu Ala Arg Lys Met Met Leu Asp
225                 230                 235                 240

Trp Ala Ser Gly Thr Leu Tyr Gln Asp Arg Phe Asp Tyr Leu Phe Tyr
                245                 250                 255

Ile His Cys Arg Glu Val Ser Leu Val Thr Gln Arg Ser Leu Gly Asp
            260                 265                 270

Leu Ile Met Ser Cys Cys Pro Asp Pro Asn Pro Ile His Lys Ile
        275                 280                 285

Val Arg Lys Pro Ser Arg Ile Leu Phe Leu Met Asp Gly Phe Asp Glu
    290                 295                 300

Leu Gln Gly Ala Phe Asp Glu His Ile Gly Pro Leu Cys Thr Asp Trp
305                 310                 315                 320

Gln Lys Ala Glu Arg Gly Asp Ile Leu Leu Ser Ser Leu Ile Arg Lys
                325                 330                 335

Lys Leu Leu Pro Glu Ala Ser Leu Leu Ile Thr Thr Arg Pro Val Ala
            340                 345                 350

Leu Glu Lys Leu Gln His Leu Leu Asp His Pro Arg His Val Glu Ile
        355                 360                 365

Leu Gly Phe Ser Glu Ala Lys Arg Lys Glu Tyr Phe Phe Lys Tyr Phe
    370                 375                 380

Ser Asp Glu Ala Gln Ala Arg Ala Ala Phe Ser Leu Ile Gln Glu Asn
385                 390                 395                 400
```

-continued

```
Glu Val Leu Phe Thr Met Cys Phe Ile Pro Leu Val Cys Trp Ile Val
                405                 410                 415
Cys Thr Gly Leu Lys Gln Gln Met Glu Ser Gly Lys Ser Leu Ala Gln
            420                 425                 430
Thr Ser Lys Thr Thr Thr Ala Val Tyr Val Phe Phe Leu Ser Ser Leu
        435                 440                 445
Leu Gln Pro Arg Gly Gly Ser Gln Glu His Gly Leu Cys Ala His Leu
    450                 455                 460
Trp Gly Leu Cys Ser Leu Ala Ala Asp Gly Ile Trp Asn Gln Lys Ile
465                 470                 475                 480
Leu Phe Glu Glu Ser Asp Leu Arg Asn His Gly Leu Gln Lys Ala Asp
                485                 490                 495
Val Ser Ala Phe Leu Arg Met Asn Leu Phe Gln Lys Glu Val Asp Cys
            500                 505                 510
Glu Lys Phe Tyr Ser Phe Ile His Met Thr Phe Gln Glu Phe Phe Ala
        515                 520                 525
Ala Met Tyr Tyr Leu Leu Glu Glu Lys Glu Gly Arg Thr Asn Val
    530                 535                 540
Pro Gly Ser Arg Leu Lys Leu Pro Ser Arg Asp Val Thr Val Leu Leu
545                 550                 555                 560
Glu Asn Tyr Gly Lys Phe Glu Lys Gly Tyr Leu Ile Phe Val Val Arg
                565                 570                 575
Phe Leu Phe Gly Leu Val Asn Gln Glu Arg Thr Ser Tyr Leu Glu Lys
            580                 585                 590
Lys Leu Ser Cys Lys Ile Ser Gln Gln Ile Arg Leu Glu Leu Leu Lys
        595                 600                 605
Trp Ile Glu Val Lys Ala Lys Ala Lys Lys Leu Gln Ile Gln Pro Ser
    610                 615                 620
Gln Leu Glu Leu Phe Tyr Cys Leu Tyr Glu Met Gln Glu Glu Asp Phe
625                 630                 635                 640
Val Gln Arg Ala Met Asp Tyr Phe Pro Lys Ile Glu Ile Asn Leu Ser
                645                 650                 655
Thr Arg Met Asp His Met Val Ser Ser Phe Cys Ile Glu Asn Cys His
            660                 665                 670
Arg Val Glu Ser Leu Ser Leu Gly Phe Leu His Asn Met Pro Lys Glu
        675                 680                 685
Glu Glu Glu Glu Glu Lys Glu Gly Arg His Leu Asp Met Val Gln Cys
    690                 695                 700
Val Leu Pro Ser Ser Ser His Ala Ala Cys Ser His Gly Leu Val Asn
705                 710                 715                 720
Ser His Leu Thr Ser Ser Phe Cys Arg Gly Leu Phe Ser Val Leu Ser
                725                 730                 735
Thr Ser Gln Ser Leu Thr Glu Leu Asp Leu Ser Asp Asn Ser Leu Gly
            740                 745                 750
Asp Pro Gly Met Arg Val Leu Cys Glu Thr Leu Gln His Pro Gly Cys
        755                 760                 765
Asn Ile Arg Arg Leu Trp Leu Gly Arg Cys Gly Leu Ser His Glu Cys
    770                 775                 780
Cys Phe Asp Ile Ser Leu Val Leu Ser Ser Asn Gln Lys Leu Val Glu
785                 790                 795                 800
Leu Asp Leu Ser Asp Asn Ala Leu Gly Asp Phe Gly Ile Arg Leu Leu
                805                 810                 815
```

```
Cys Val Gly Leu Lys His Leu Leu Cys Asn Leu Lys Lys Leu Trp Leu
            820                 825                 830

Val Ser Cys Cys Leu Thr Ser Ala Cys Cys Gln Asp Leu Ala Ser Val
            835                 840                 845

Leu Ser Thr Ser His Ser Leu Thr Arg Leu Tyr Val Gly Glu Asn Ala
        850                 855                 860

Leu Gly Asp Ser Gly Val Ala Ile Leu Cys Glu Lys Ala Lys Asn Pro
865                 870                 875                 880

Gln Cys Asn Leu Gln Lys Leu Gly Leu Val Asn Ser Gly Leu Thr Ser
            885                 890                 895

Val Cys Cys Ser Ala Leu Ser Ser Val Leu Ser Thr Asn Gln Asn Leu
            900                 905                 910

Thr His Leu Tyr Leu Arg Gly Asn Thr Leu Gly Asp Lys Gly Ile Lys
        915                 920                 925

Leu Leu Cys Glu Gly Leu Leu His Pro Asp Cys Lys Leu Gln Val Leu
    930                 935                 940

Glu Leu Asp Asn Cys Asn Leu Thr Ser His Cys Cys Trp Asp Leu Ser
945                 950                 955                 960

Thr Leu Leu Thr Ser Ser Gln Ser Leu Arg Lys Leu Ser Leu Gly Asn
            965                 970                 975

Asn Asp Leu Gly Asp Leu Gly Val Met Met Phe Cys Glu Val Leu Lys
        980                 985                 990

Gln Gln Ser Cys Leu Leu Gln Asn Leu Gly Leu Ser Glu Met Tyr Phe
            995                 1000                1005

Asn Tyr Glu Thr Lys Ser Ala Leu Glu Thr Leu Gln Glu Glu Lys Pro
        1010                1015                1020

Glu Leu Thr Val Val Phe Glu Pro Ser Trp
1025                1030

<210> SEQ ID NO 6
<211> LENGTH: 3102
<212> TYPE: DNA
<213> ORGANISM: Homo sapiens

<400> SEQUENCE: 6
atggcaagca cccgctgcaa gctggccagg tacctggagg acctggagga tgtggacttg    60
aagaaattta agatgcactt agaggactat cctccccaga agggctgcat ccccctcccg   120 agggtcaga cagagaaggc agaccatgtg gatctagcca cgctaatgat cgacttcaat   180
ggggaggaga aggcgtgggc catggccgtg tggatcttcg ctgcgatcaa caggagagac   240
ctttatgaga aagcaaaaag agatgagccg aagtggggtt cagataatgc acgtgtttcg   300
aatcccactg tgatatgcca ggaagacagc attgaagagg agtggatggg tttactggag   360 taccttttcga gaatctctat ttgtaaaatg aagaaagatt accgtaagaa gtacagaaag   420
tacgtgagaa gcagattcca gtgcattgaa gacaggaatg cccgtctggg tgagagtgtg   480
agcctcaaca acgctacac acgactgcgt ctcatcaagg agcaccggag ccagcaggag   540
agggagcagg agcttctggc catcggcaag accaagacgt gtgagagccc cgtgagtccc   600
attaagatgg agttgctgtt tgaccccgat gatgagcatt ctgagcctgt gcacaccgtg   660
gtgttccagg ggcggcagg gattgggaaa caatcctgg ccaggaagat gatgttggac   720
tgggcatcgg ggacactcta ccaagacagg tttgactatc tgttctatat ccactgtcgg   780
gaggtgagcc ttgtgacaca gaggagcctg gggacctga tcatgagctg ctgccccgac   840
ccaaacccac ccatccacaa gatcgtgaga aaaccctcca gaatcctctt cctcatggac   900
```

```
ggcttcgatg agctgcaagg tgcctttgac gagcacatag gaccgctctg cactgactgg      960
cagaaggccg agcggggaga cattctcctg agcagcctca tcagaaagaa gctgcttccc     1020
gaggcctctc tgctcatcac cacgagacct gtggccctgg agaaactgca gcacttgctg     1080
gaccatcctc ggcatgtgga gatcctgggt ttctccgagg ccaaaaggaa agagtacttc     1140
ttcaagtact ctctgatga ggcccaagcc agggcagcct tcagtctgat tcaggagaac      1200
gaggtcctct tcaccatgtg cttcatcccc ctggtctgct ggatcgtgtg cactggactg     1260
aaacagcaga tggagagtgg caagagcctt gcccagacat ctaagaccac caccgcggtg     1320
tacgtcttct tcctttccag tttgctgcag ccccggggag ggagccagga gcacggcctc     1380
tgcgcccacc tctgggggct ctgctctttg gctgcagatg gaatctggaa ccagaaaatc     1440
ctgtttgagg agtccgacct caggaatcat ggactgcaga aggcggatgt gtctgctttc     1500
ctgaggatga acctgttcca aaaggaagtg gactgcgaga agttctacag cttcatccac     1560
atgactttcc aggagttctt tgccgccatg tactacctgc tggaagagga aaaggaagga     1620
aggacgaacg ttccagggag tcgtttgaag cttcccagcc gagacgtgac agtccttctg     1680
gaaaactatg gcaaattcga aaggggtat ttgattttttg ttgtacgttt cctcttttggc    1740
ctggtaaacc aggagaggac ctcctacttg gagaagaaat taagttgcaa gatctctcag    1800
caaatcaggc tggagctgct gaaatggatt gaagtgaaag ccaaagctaa aaagctgcag    1860
atccagccca gccagctgga attgttctac tgtttgtacg agatgcagga ggaggacttc    1920
gtgcaaaggg ccatggacta tttcccaag attgagatca atctctccac cagaatggac    1980
cacatggttt cttcctttttg cattgagaac tgtcatcggg tggagtcact gtccctgggg  2040
tttctccata acatgcccaa ggaggaagag gaggaggaaa aggaaggccg acaccttgat    2100
atggtgcagt gtgtcctccc aagctcctct catgctgcct gttctcatgg attggtgaac    2160
agccacctca cttccagttt ttgccggggc ctcttttcag ttctgagcac agccagagt     2220
ctaactgaat tggacctcag tgacaattct ctgggggacc cagggatgag agtgttgtgt    2280
gaaacgctcc agcatcctgg ctgtaacatt cggagattgt ggttggggcg ctgtggcctc   2340
tcgcatgagt gctgcttcga catctccttg gtcctcagca gcaaccagaa gctggtggag   2400
ctggacctga gtgacaacgc cctggtgac ttcggaatca gacttctgtg tgtgggactg    2460
aagcacctgt tgtgcaatct gaagaagctc tggttggtca gctgctgcct cacatcagca   2520
tgttgtcagg atcttgcatc agtattgagc accagccatt ccctgaccag actctatgtg    2580
ggggagaatg ccttgggaga ctcaggagtc gcaattttat gtgaaaaagc caagaatcca    2640
cagtgtaacc tgcagaaaact ggggttggtg aattctggcc ttacgtcagt ctgttgttca    2700
gctttgtcct cggtactcag cactaatcag aatctcacgc acctttacct gcgaggcaac   2760
actctcggag acaaggggat caaactactc tgtgagggac tcttgcaccc cgactgcaag   2820
cttcaggtgt tggaattaga caactgcaac ctcacgtcac actgctgctg ggatctttcc    2880
acacttctga cctccagcca gagcctgcga aagctgagcc tgggcaacaa tgacctgggc    2940
gacctggggg tcatgatgtt ctgtgaagtg ctgaaacagc agagctgcct cctgcagaac    3000
ctggggttgt ctgaaatgta tttcaattat gagacaaaaa gtgcgttaga aacacttcaa     3060
gaagaaaagc ctgagctgac cgtcgtcttt gagccttctt gg                       3102
```

<210> SEQ I NO 7
<211> LENGTH: 77
<212> TYPE: PRT

```
<213> ORGANISM: Homo sapiens

<400> SEQUENCE: 7

Asp His Leu Leu Ser Thr Leu Glu Glu Leu Val Pro Tyr Asp Phe Glu
1               5                   10                  15

Lys Phe Lys Phe Lys Leu Gln Asn Thr Ser Val Gln Lys Glu His Ser
            20                  25                  30

Arg Ile Pro Arg Ser Gln Ile Gln Arg Ala Arg Pro Val Lys Met Ala
        35                  40                  45

Thr Leu Leu Val Thr Tyr Tyr Gly Glu Glu Tyr Ala Val Gln Leu Thr
    50                  55                  60

Leu Gln Val Leu Arg Ala Ile Asn Gln Arg Leu Leu Ala
65                  70                  75

<210> SEQ ID NO 8
<211> LENGTH: 77
<212> TYPE: PRT
<213> ORGANISM: Homo sapiens

<400> SEQUENCE: 8

Asp Ala Ile Leu Asp Ala Leu Glu Asn Leu Thr Ala Glu Glu Leu Lys
1               5                   10                  15

Lys Phe Lys Leu Leu Leu Ser Val Pro Leu Arg Glu Gly Tyr Gly
            20                  25                  30

Arg Ile Pro Arg Gly Ala Leu Leu Ser Met Asp Ala Leu Asp Leu Thr
        35                  40                  45

Asp Lys Leu Val Ser Phe Tyr Leu Glu Thr Tyr Gly Ala Glu Leu Thr
    50                  55                  60

Ala Asn Val Leu Arg Asp Met Gly Leu Gln Glu Met Ala
65                  70                  75

<210> SEQ ID NO 9
<211> LENGTH: 77
<212> TYPE: PRT
<213> ORGANISM: Homo sapiens

<400> SEQUENCE: 9

Gly Arg Leu Ala Cys Tyr Leu Glu Phe Leu Lys Lys Glu Glu Leu Lys
1               5                   10                  15

Glu Phe Gln Leu Leu Leu Ala Asn Lys Ala His Ser Arg Ser Ser Ser
            20                  25                  30

Gly Glu Thr Pro Ala Gln Pro Glu Lys Thr Ser Gly Met Glu Val Ala
        35                  40                  45

Ser Tyr Leu Val Ala Gln Tyr Gly Glu Gln Arg Ala Trp Asp Leu Ala
    50                  55                  60

Leu His Thr Trp Glu Gln Met Gly Leu Arg Ser Leu Cys
65                  70                  75

<210> SEQ ID NO 10
<211> LENGTH: 77
<212> TYPE: PRT
<213> ORGANISM: Artificial sequence
<220> FEATURE:
<223> OTHER INFORMATION: Consensus sequence
<220> FEATURE:
<221> NAME/KEY: VARIANT
<222> LOCATION: (1)...(77)
<223> OTHER INFORMATION: Xaa = Any Amino Acid

<400> SEQUENCE: 10
```

```
Asp Xaa Leu Leu Xaa Xaa Leu Glu Xaa Leu Xaa Xaa Glu Glu Leu Lys
 1               5                  10                  15

Lys Phe Lys Leu Leu Xaa Asn Xaa Ser Xaa Xaa Xaa Glu Xaa Ser
             20                  25                  30

Arg Ile Pro Arg Xaa Gln Xaa Xaa Lys Ala Asp Gly Xaa Xaa Leu Ala
         35                  40                  45

Xaa Xaa Leu Val Thr Xaa Tyr Gly Xaa Tyr Ala Val Glu Leu Ala
     50                  55                  60

Leu Gln Val Leu Glu Xaa Met Gly Leu Arg Xaa Leu Ala
 65              70                  75
```

<210> SEQ ID NO 11
<211> LENGTH: 77
<212> TYPE: PRT
<213> ORGANISM: Artificial sequence
<220> FEATURE:
<223> OTHER INFORMATION: Consensus sequence
<220> FEATURE:
<221> NAME/KEY: VARIANT
<222> LOCATION: (1)...(77)
<223> OTHER INFORMATION: Xaa = Any Amino Acid

<400> SEQUENCE: 11

```
Asp Xaa Leu Ala Xaa Tyr Leu Glu Xaa Leu Xaa Xaa Glu Glu Leu Lys
 1               5                  10                  15

Lys Phe Lys Leu Leu Xaa Asn Xaa Ser Pro Gln Lys Gly Xaa Ser
             20                  25                  30

Arg Ile Pro Arg Gly Gln Xaa Glu Lys Ala Asp Gly Val Asp Leu Ala
         35                  40                  45

Thr Leu Leu Val Thr Phe Tyr Gly Glu Tyr Ala Trp Ala Leu Ala
     50                  55                  60

Leu Gln Val Leu Glu Ala Met Gly Leu Arg Asp Leu Ala
 65              70                  75
```

<210> SEQ ID NO 12
<211> LENGTH: 28
<212> TYPE: PRT
<213> ORGANISM: Artificial sequence
<220> FEATURE:
<223> OTHER INFORMATION: Consensus sequence

<400> SEQUENCE: 12

```
Asn Pro Ser Leu Arg Glu Leu Asp Leu Ser Asn Asn Lys Leu Gly Asp
 1               5                  10                  15

Glu Gly Ala Arg Ala Leu Ala Glu Ala Leu Lys Ser
             20                  25
```

<210> SEQ ID NO 13
<211> LENGTH: 23
<212> TYPE: PRT
<213> ORGANISM: Artificial sequence
<220> FEATURE:
<223> OTHER INFORMATION: Consensus sequence

<400> SEQUENCE: 13

```
Asn Leu Glu Glu Leu Asp Leu Ser Asn Asn Leu Thr Ser Leu Pro Pro
 1               5                  10                  15

Gly Leu Phe Ser Asn Leu Pro
             20
```

US 7,321,028 B2

MOLECULES OF THE PYRIN DOMAIN PROTEIN FAMILY AND USES THEREOF

RELATED APPLICATION INFORMATION

This application is a divisional of U.S. application Ser. No. 09/653,901, filed Sep. 1, 2000 now abandoned, which is a continuation-in-part of U.S. application Ser. No. 09/506,067, filed Feb. 17, 2000 now abandoned. The entire content of each of these applications is incorporated herein by reference.

BACKGROUND OF THE INVENTION

Many cytoplasmic plant proteins involved in plant resistance to pathogens, generally referred to as "R" proteins, possess both a nucleotide binding site (NBS) and a leucine rich repeat (LRR). R proteins are involved in both a rapid defense response (hypersensitive response) and more long-term nonspecific resistance (systemic acquired resistance). The hypersensitive response involves a form of programmed death localized to the site of infection and changes in gene expression that are thought to prevent further infection. The LRR of the R proteins is believed to recognize and bind to pathogen-derived proteins, triggering the defensive responses and resulting in a rapid and localized host cell death. Many R proteins have an amino terminal effector domain (e.g., a TIR domain or a leucine zipper domain) that is thought to play a role in downstream signaling of events triggered by infection and, possibly, other stresses.

The R proteins are structurally similar to APAF-1, a protein which mediates between Bcl-2, a negative regulator of apoptosis, and caspases, the proteases directly responsible for the degradation of cellular proteins that leads to the morphological changes seen in cells undergoing apoptosis. A domain, designated the NB-ARC domain ("nucleotide-binding adaptor shared by APAF-1, certain R gene products and CED-4"), contains a series of motifs and residues that are conserved among plant resistance proteins (e.g., R proteins) and regulators of cell death (e.g., APAF-1 and CED-4) (van der Bizen and Jones (1999) Current Biology 8:226-228). In addition to the NBS, APAF-1 has a CARD domain, functionally analogous to the effector domain of R proteins, and a WD-40 domain, functionally analogous to the LRR domain of R proteins.

The mechanisms that mediate apoptosis have been intensively studied. These mechanisms involve the activation of endogenous proteases, loss of mitochondrial function, and structural changes such as disruption of the cytoskeleton, cell shrinkage, membrane blebbing, and nuclear condensation due to degradation of DNA.

The various signals that trigger apoptosis are thought to bring about these events by converging on a common cell death pathway, the core components of which are highly conserved from worms, such as $C.$ $elegans$, to humans. In fact, invertebrate model systems have been invaluable tools in identifying and characterizing the genes that control apoptosis. Despite this conservation of certain core components, apoptotic signaling in mammals is much more complex than in invertebrates. For example, in mammals there are multiple homologues of the core components in the cell death signaling pathway.

Caspases, a class of proteins central to the apoptotic program, are responsible for the degradation of cellular proteins that leads to the morphological changes seen in cells undergoing apoptosis. Caspases (cysteinyl aspartate-specific proteinases) are cysteine proteases having specificity for aspartate at the substrate cleavage site. Generally, caspases are classified as either initiator caspases or effector caspases, both of which are zymogens that are activated by proteolysis that generates an active species. An effector caspase is activated by an initiator caspase which cleaves the effector caspase. Initiator caspases are activated by an auto-proteolytic mechanism that is often dependent upon oligomerization directed by association of the caspase with an adapter molecule.

Apoptotic signaling is dependent on protein-protein interactions. At least three different protein-protein interaction domains, the death domain, the death effector domain and the caspase recruitment domain (CARD), have been identified within proteins involved in apoptosis. A fourth protein-protein interaction domain, the death recruiting domain (DRD) was recently identified in murine FLASH (Imai et al. (1999) $Nature$ 398:777-85).

Caspases comprise a multi-gene family having at least 12 distinct family members (Nicholson (1999) $Cell$ $Death$ $and$ $Differentiation$ 6:1028). A relatively small fraction of cellular polypeptides (less than 200) are thought to serve as targets for cleavage by caspases. Because many of these caspase targets perform key cellular functions, their proteolysis is thought to account for the cellular and morphological events that occur during apoptosis. Members of the caspase gene family can be divided by phylogenetic analysis into two major subfamilies, based upon their relatedness to ICE (interleukin-1β converting enzyme; caspase-1) and CED-3. Alternate groupings of caspases can be made based upon their substrate specificities.

Many caspases and proteins that interact with caspases possess a CARD domain. Hofmann et al. ((1997) TIBS 22:155) and others have postulated that certain apoptotic proteins bind to each other via their CARD domains and that different subtypes of CARD domains may confer binding specificity, regulating the activity of various caspases, for example.

CARD-4 is a member of the CED-4/Apaf-1 family that interacts with RICK, a serine threonine kinase, and induces NF-κB via the signaling protein TRAF-6 and NIK (Bertin et al. (1999) J. Biol. Chem. 274:12955). CARD-4 includes domains that are similar to the nucleotide binding site domain (NBS) and leucine rich repeat (LRR) domains found in plant R proteins that mediate resistance to pathogens.

SUMMARY OF THE INVENTION

The invention features nucleic acid molecules encoding human NBS-1 and human PYRIN-1. Both NBS-1 and PYRIN-1 have a pyrin domain, so-named for its homology to a portion of pyrin (marenostrin). Mutations in the pyrin gene are associated with familial Mediterranean fever (FMF), an inherited inflammatory disease. NBS-1 and PYRIN-1 also have a nucleotide binding site (NBS) domain and a leucine rich repeat domain (LRR) domain, both of which are present in a number of proteins that transmit signals which activate apoptotic and inflammatory pathways in response to stress and other stimuli.

NBS-1 and PYRIN-1 nucleic acids and polypeptides, as well as modulators of NBS-1 or PYRIN-1 activity or expression, are expected to be useful in the modulation of stress-related, apoptotic and inflammatory responses, e.g., for the treatment of apoptotic and inflammatory disorders. In addition, NBS-1 and PYRIN-1 nucleic acids and polypeptides are expected to be useful in the diagnosis of apoptotic and inflammatory disorders as well as in screening assays which can be used to identify compounds which can be used to modulate stress-related, apoptotic and inflammatory responses.

Many cytoplasmic plant proteins involved in response to plant pathogens, generally referred to as "R" proteins have both an NBS domain and an LRR domain. R proteins are involved in both a rapid defense response (hypersensitive response) and more long-term nonspecific resistance (systemic acquired resistance). The hypersensitive response involves cell and tissue death that is localized to the site of infection. The LRR domains of R proteins are believed to recognize and bind to pathogen proteins, triggering defensive responses. Many R proteins have an amino terminal effector domain (e.g., a TIR domain or a leucine zipper domain) that is thought to play a role in downstream signaling of events triggered by infection and, possibly, other stresses.

The R proteins have some structural similarity to APAF-1, a protein which mediates between Bcl-2, a negative regulator of apoptosis, and caspases, which are the proteases directly responsible for the degradation of cellular proteins that leads to the morphological changes seen in cells undergoing apoptosis. APAF-1 has a CARD domain, functionally analogous to the effector domain of R proteins, an NBS domain, and a WD-40 domain, functionally analogous to the LRR domain of R proteins.

CARD-4, CARD-7, and CARD-12 each have an NBS domain and an LRR domain as well as a CARD domain (detailed information concerning CARD-4, CARD-7, and CARD-12 can be found in U.S. application Ser. No. 09/245,281, filed Feb. 5, 1999, U.S. application Ser. No. 09/207,359, filed Dec. 8, 1998, U.S. application Ser. No. 09/099,041, filed Jun. 17, 1998, U.S. application Ser. No. 09/019,942, filed Feb. 6, 1998, U.S. application Ser. No. 09/428,252, filed Oct. 27, 1999, and U.S. application Ser. No. 60/161,822, filed Oct. 27, 1999, all of which are incorporated herein by reference). The CARD domain, which is present in a number of apoptotic signaling molecules, is an effector domain that thought to be involved in homophilic protein-protein interactions, e.g., with downstream CARD-containing signaling molecules. For example, the CARD domain of CARD-4 interacts with the CARD domain of RICK (RIP2, CARDIAK), a serine-threonine kinase that activates NF-κB signaling pathways.

Other proteins structurally related to NBS-1 and PYRIN-1 include PCD-1, PCD-2, and PCD-3, each of which contains both an NBS domain and a leucine zipper domain. A leucine zipper domain, like the CARD domain and the pyrin domain, is an effector domain thought to be involved in homophilic protein-protein interactions. PCD-2 and PCD-3 also each contains LRR domains. PCD-1, which is truncated at is carboxy terminus, is also expected to contain an LRR domain. Detailed information concerning PCD-1, PCD-2, and PCD-3 can be found in U.S. application Ser. No. 09/563,876, filed May 3, 2000, which is incorporated herein by reference.

Other proteins structurally related to NBS-1 and PYRIN-1 include NBS-2, NBS-3, NBS-4, and NBS-5, each of which contains an NBS domain. NBS-2, NBS-3, and NBS-5 contain LRR domains and NBS-2 and NBS-3 contain pyrin domains. Detailed information concerning NBS-2, NBS-3, NBS-4, and NBS-5 can be found in U.S. application Ser. No. 60/201,464, filed May 3, 2000, which is incorporated herein by reference.

In general, an NBS domain includes a kinase 1a domain (P-loop), a kinase 2 domain (Walker B box) and a kinase 3a domain. An LRR domain usually is composed of several leucine rich repeats.

Without being bound by a particular theory, it is possible that the LRR domain of NBS-1 and PYRIN-1 interacts with an upstream signaling molecule that is associated with stress, infection, or inflammation. This interaction triggers a conformational change in NBS-1 or PYRIN-1 that exposes an effector domain, e.g., the pyrin domain of NBS-1. The exposed effector domain then mediates interaction with a downstream signaling molecule or molecules to transmit a stress-related, apoptotic or inflammatory signal. In this model, the conformational change is dependent upon hydrolysis of a nucleotide triphosphate (ATP or GTP) bound to the NBS domain.

NBS-1 and PYRIN-1 molecules are useful as modulating agents in regulating a variety of cellular processes including cell growth and cell death. In one aspect, this invention provides isolated nucleic acid molecules encoding NBS-1 or PYRIN-1 proteins or biologically active portions thereof, as well as nucleic acid fragments suitable as primers or hybridization probes for the detection of NBS-1 or PYRIN-1 encoding nucleic acids.

The invention encompasses methods of diagnosing and treating patients who are suffering from a disorder associated with an abnormal level or rate (undesirably high or undesirably low) of apoptotic cell death, abnormal activity of stress-related pathways of the endoplasmic reticulum (ER), abnormal activity of the Fas/APO-1 receptor complex, abnormal activity of the TNF receptor complex, or abnormal activity of a caspase by administering a compound that modulates the expression of NBS-1 or PYRIN-1 (at the DNA, mRNA or protein level, e.g., by altering mRNA splicing) or by altering the activity of NBS-1 or PYRIN-1. Examples of such compounds include small molecules, antisense nucleic acid molecules, ribozymes, and polypeptides.

Certain disorders are associated with an increased number of surviving cells, which are produced and continue to survive or proliferate when apoptosis is inhibited or occurs at an undesirably low rate. NBS-1 or PYRIN-1 and compounds that modulate the expression or activity of NBS-1 or PYRIN-1 can be used to treat or diagnose such disorders. These disorders include cancer (particularly follicular lymphomas, chronic myelogenous leukemia, melanoma, colon cancer, lung carcinoma, carcinomas associated with mutations in p53, and hormone-dependent tumors such as breast cancer, prostate cancer, and ovarian cancer). Such compounds can also be used to treat viral infections (such as those caused by herpesviruses, poxviruses, and adenoviruses). Failure to remove autoimmune cells that arise during development or that develop as a result of somatic mutation during an immune response can result in autoimmune disease. Thus, an autoimmune disorder can be caused by an undesirably low level of apoptosis. Accordingly, NBS-1 or PYRIN-1 and modulators of NBS-1 or PYRIN-1 activity or expression can be used to treat autoimmune disorders (e.g., systemic lupus erythematosis, immune-mediated glomerulonephritis, and arthritis).

Many diseases are associated with an undesirably high rate of apoptosis. NBS-1 or PYRIN-1 and modulators of NBS-1 or PYRIN-1 expression or activity can be used to treat or diagnose such disorders. A wide variety of neurological diseases are characterized by the gradual loss of specific sets of neurons. Such disorders include Alzheimer's disease, Parkinson's disease, amyotrophic lateral sclerosis (ALS), retinitis pigmentosa, spinal muscular atrophy, Huntington's disease, and various forms of cerebellar degeneration. The cell loss in these diseases does not induce an inflammatory response, and apoptosis appears to be the mechanism of cell death. In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis. Additional diseases associated with an undesirably high rate of apoptosis include: ischemic and hypoxic brain injury, traumatic and excitotoxic brain damage, neuronal transplantation, acute bacterial meningitis, kidney ischemia/reperfusion injury, and liver disease. NBS-1 or PYRIN-1 and modulators of NBS-1 or PYRIN-1 may therefore be useful in treating and diagnosing these conditions.

Populations of cells are often depleted in the event of viral infection, with perhaps the most dramatic example being the cell depletion caused by the human immunodeficiency virus (HIV). Surprisingly, most T cells that die during HIV infections do not appear to be infected with HIV. Although a number of explanations have been proposed, recent evidence suggests that stimulation of the CD4 receptor results in the enhanced susceptibility of uninfected T cells to undergo apoptosis.

NBS-1 or PYRIN-1 polypeptides, nucleic acids and modulators of NBS-1 or PYRIN-1 expression or activity can be used to treat inflammatory disorders and immune system disorders. The inflammatory and immune disorders include, but are not limited to, chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis), certain viral infections, including HIV, and bacterial infections, including tuberculosis and lepromatous leprosy.

Ischemia is often accompanied by inflammation that causes cell death. Because NBS-1 and PYRIN-1 are expected to play a role in stress-related response, inflammation and apoptosis, NBS-1 or PYRIN-1 polypeptides, nucleic acids, and modulators of NBS-1 or PYRIN-1 expression or activity can be used to treat cells death accompanying inflammatory responses triggered by ischemia.

Invasive infection with Gram-negative bacteria and Gram-positive bacteria often results in septic shock. NBS-1 and PYRIN-1 may recognize and bind components of Gram-negative bacteria and Gram-positive bacteria or other infectious agents (e.g., intracellular parasites), triggering an inflammatory response. Thus, NBS-1 and PYRIN-1 may play a role in innate immune system responses that is similar to that of Toll-like receptor 2 (TLR2), a receptor which has some structural similarity to plant R proteins and IL-1R. TLR2 is a signaling receptor that, in association with CD14, is activated by LPS in a response that requires LPS-binding protein. The interaction of TLR2 with LPS leads to TLR2 oligomerization and recruitment of IRAK (Yang et al. (1998) Nature 395:284-88; Yang et al (1999) J. Immunol. 163:639-43; and Yoshimura et al. (1999) J. Immunol. 163: 105). Thus, TLR2 is thought to be a direct mediator of signaling by LPS. TLR2 is also thought to mediate cell activation induced by peptidoglycan and lipoteichoic acid, the main stimulatory components of Gram-positive bacteria (Schwandner et al. (1999) J. Biol. Chem. 274:17406-09).

In addition to the aforementioned disorders, NBS-1 or PYRIN-1 polypeptides, nucleic acids, and modulators of NBS-1 or PYRIN-1 expression or activity can be used to treat septic shock and other disorders associated with an innate immune response. For example, NBS-1 or PYRIN-1 may bind to a component of an intracellular infectious agent or a component of an infectious agent that is brought into a cell expressing NBS-1 or PYRIN-1, e.g., a component that enters a cell through a receptor or is expressed by a viral gene.

In addition to the aforementioned disorders, NBS-1 or PYRIN-1 polypeptides, nucleic acids, and modulators of NBS-1 or PYRIN-1 expression or activity can be used to treat disorders of cell signaling and disorders of tissues in which NBS-1 or PYRIN-1 is expressed.

The invention features a nucleic acid molecule which is at least 45% (or 55%, 65%, 75%, 85%, 95%, or 98%) identical to the nucleotide sequence shown in SEQ ID NO:1, SEQ ID NO:3, SEQ ID NO:4, SEQ ID NO:6, or a complement thereof.

The invention features a nucleic acid molecule which includes a fragment of at least 150 (300, 325, 350, 375, 400, 425, 450, 500, 550, 600, 650, 700, 800, 900, 1000, 1100, 1200, 1300, 1400, 1500, 1600, 1800, 2000, 2250, 2500, 2750, 3000, 3250, 3500, 3750, or 3850) nucleotides of the nucleotide sequence shown in SEQ ID NO:1, SEQ ID NO:3, SEQ ID NO:4, SEQ ID NO:6, or a complement thereof.

In an embodiment, a NBS-1 nucleic acid molecule has the nucleotide sequence shown in SEQ ID NO:1 or SEQ ID NO:3.

Also within the invention is a nucleic acid molecule which encodes a fragment of a polypeptide having the amino acid sequence of SEQ ID NO:2.

The invention includes a nucleic acid molecule which encodes a naturally occurring allelic variant of a polypeptide comprising the amino acid sequence of SEQ ID NO:2, wherein the nucleic acid molecule hybridizes to a nucleic acid molecule consisting of SEQ ID NO:1 or SEQ ID NO:3 under stringent conditions.

In general, an allelic variant of a gene will be readily identifiable as mapping to the same chromosomal location as said gene.

The invention also includes a nucleic acid molecule encoding a naturally occurring polypeptide, wherein the nucleic acid hybridizes to a nucleic acid molecule consisting of SEQ ID NO:3 under stringent conditions (e.g., hybridization in 6× sodium chloride/sodium citrate (SSC) at about 60° C., followed by one or more washes in 0.2×SSC, 0.1% SDS at 65° C.), and wherein the nucleic acid encodes a polypeptide of 1030-1033 amino acids in length, preferably 1033 amino acids, having a molecular weight of 113.6 kD prior to post-translational modifications. Thus, the invention encompasses a nucleic acid molecule which includes the sequence of the protein coding region of a naturally occurring mRNA (or the corresponding cDNA sequence) that is expressed in a human cell.

Also within the invention are: an isolated NBS-1 protein having an amino acid sequence that is at least about 65%, preferably 75%, 85%, 95%, or 98% identical to the amino acid sequence of SEQ ID NO:2; and an isolated NBS-1 protein having an amino acid sequence that is at least about 65%, preferably 75%, 85%, 95%, or 98% identical to the pyrin domain of SEQ ID NO:2 (e.g., about amino acid residues 3-79 of SEQ ID NO:2); an isolated NBS-1 protein having an amino acid sequence that is at least about 65%, preferably 75%, 85%, 95%, or 98% identical to the NBS domain of SEQ ID NO:2 (e.g., about amino acids 174-605 of SEQ ID NO:2); an isolated NBS-1 protein having an amino acid sequence that is at least about 65%, preferably 75%, 85%, 95%, or 98% identical to the kinase 1a domain of SEQ ID NO:2 (e.g., about amino acids 180-195 of SEQ ID NO:2); an isolated NBS-1 protein having an amino acid sequence that is at least about 65%, preferably 75%, 85%, 95%, or 98% identical to the kinase 1a domain of SEQ ID NO:2 (e.g., about amino acids 180-195 of SEQ ID NO:2); an isolated NBS-1 protein having an amino acid sequence that is at least about 65%, preferably 75%, 85%, 95%, or 98% identical to the kinase 2 domain of SEQ ID NO:2 (e.g., about amino acids 249-264 of SEQ ID NO:2); an isolated NBS-1 protein having an amino acid sequence that is at least about 65%, preferably 75%, 85%, 95%, or 98% identical to the kinase 3a domain of SEQ ID NO:2 (e.g., about amino acids 302-313 of SEQ ID NO:2); an isolated NBS-1 protein having an amino acid sequence that is at least about 65%, preferably 75%, 85%, 95%, or 98% identical to the LRR domain of SEQ ID NO:2 (e.g., about amino acids 670-1008 of SEQ ID NO:2); and an isolated NBS-1 protein having an amino acid sequence that is at least about 65%, preferably 75%, 85%, 95%, or 98% identical to one or more of the leucine rich repeat of SEQ ID NO:2 (e.g., about amino acids residues 670-697, 698-725, 726-752, 754-781, 782-809, 811-838, 839-866, 868-895, 896-923, 925-952, 953-979, and 1981-1008 of SEQ ID NO:2).

In an embodiment, a PYRIN-1 nucleic acid molecule has the nucleotide sequence shown in SEQ ID NO:4 or SEQ ID NO:6.

Also within the invention is a nucleic acid molecule which encodes a fragment of a polypeptide having the amino acid sequence of SEQ ID NO:5.

The invention includes a nucleic acid molecule which encodes a naturally occurring allelic variant of a polypeptide comprising the amino acid sequence of SEQ ID NO:5, wherein the nucleic acid molecule hybridizes to a nucleic acid molecule consisting of SEQ ID NO:4 or SEQ ID NO:6 under stringent conditions.

In general, an allelic variant of a gene will be readily identifiable as mapping to the same chromosomal location as said gene.

The invention also includes a nucleic acid molecule encoding a naturally occurring polypeptide, wherein the nucleic acid hybridizes to a nucleic acid molecule consisting of SEQ ID NO:6 under stringent conditions (e.g., hybridization in 6× sodium chloride/sodium citrate (SSC) at about 60° C., followed by one or more washes in 0.2×SSC, 0.1% SDS at 65° C.), and wherein the nucleic acid encodes a polypeptide of 1031-1037 amino acids in length, preferably 1034 amino acids, having a molecular weight of 117.9 kD prior to post-translational modifications. Thus, the invention encompasses a nucleic acid molecule which includes the sequence of the protein coding region of a naturally occurring mRNA (or the corresponding cDNA sequence) that is expressed in a human cell.

Also within the invention are: an isolated PYRIN-1 protein having an amino acid sequence that is at least about 65%, preferably 75%, 85%, 95%, or 98% identical to the amino acid sequence of SEQ ID NO:5; an isolated PYRIN-1 protein having an amino acid sequence that is at least about 65%, preferably 75%, 85%, 95%, or 98% identical to the pyrin domain of SEQ ID NO:5 (e.g., about amino acid residues 1-87 of SEQ ID NO:5); an isolated PYRIN-1 protein having an amino acid sequence that is at least about 65%, preferably 75%, 85%, 95%, or 98% identical to the NBS domain of SEQ ID NO:5 (e.g., about amino acids 263-357 of SEQ ID NO:5); an isolated PYRIN-1 protein having an amino acid sequence that is at least about 65%, preferably 75%, 85%, 95%, or 98% identical to the kinase 1a domain of SEQ ID NO:5 (e.g., about amino acids 224-233 of SEQ ID NO:5); an isolated PYRIN-1 protein having an amino acid sequence that is at least about 65%, preferably 75%, 85%, 95%, or 98% identical to the kinase 2 domain of SEQ ID NO:5 (e.g., about amino acids 290-306 of SEQ ID NO:5); an isolated PYRIN-1 protein having an amino acid sequence that is at least about 65%, preferably 75%, 85%, 95%, or 98% identical to the kinase 3a domain of SEQ ID NO:5 (e.g., about amino acids 344-355 of SEQ ID NO:5); an isolated PYRIN-1 protein having an amino acid sequence that is at least about 65%, preferably 75%, 85%, 95%, or 98% identical to the LRR domain of SEQ ID NO:5 (e.g., about amino acids 740-991 of SEQ ID NO:5); and an isolated PYRIN-1 protein having an amino acid sequence that is at least about 65%, preferably 75%, 85%, 95%, or 98% identical to one or more of the leucine rich repeat of SEQ ID NO:5 (e.g., about amino acids residues 740-767, 769-796, 797-821, 826-849, 854-878, 883-906, 911-935, 940-967, and 968-991 of SEQ ID NO:5).

Also within the invention are: an isolated NBS-1 protein which is encoded by a nucleic acid molecule having a nucleotide sequence that is at least about 65%, preferably 75%, 85%, or 95% identical to SEQ ID NO:3; an isolated NIBS-1 protein which is encoded by a nucleic acid molecule having a nucleotide sequence at least about 65% preferably 75%, 85%, or 95% identical to the pyrin domain encoding portion of SEQ ID NO:3; an isolated NBS-1 protein which is encoded by a nucleic acid molecule having a nucleotide sequence at least about 65% preferably 75%, 85%, or 95% identical to the NIBS domain encoding portion of SEQ ID NO:3; an isolated NBS-1 protein which is encoded by a nucleic acid molecule having a nucleotide sequence at least about 65% preferably 75%, 85%, or 95% identical to the kinase 1a, kinase 2, or kinase 3a region encoding portion of SEQ ID NO:3; an isolated NBS-1 protein which is encoded by a nucleic acid molecule having a nucleotide sequence at least about 65% preferably 75%, 85%, or 95% identical to the LRR domain encoding portion of SEQ ID NO:3 or one or more leucine rich repeat encoding portions of SEQ ID NO:3; and an isolated NBS-1 protein which is encoded by a nucleic acid molecule having a nucleotide sequence which hybridizes under stringent hybridization conditions to a nucleic acid molecule having the nucleotide sequence of SEQ ID NO:3.

Also within the invention are: an isolated PYRIN-1 protein which is encoded by a nucleic acid molecule having a nucleotide sequence that is at least about 65%, preferably 75%, 85%, or 95% identical to SEQ ID NO:6; an isolated PYRIN-1 protein which is encoded by a nucleic acid molecule having a nucleotide sequence at least about 65% preferably 75%, 85%, or 95% identical to the pyrin domain encoding portion of SEQ ID NO:6; an isolated PYRIN-1 protein which is encoded by a nucleic acid molecule having a nucleotide sequence at least about 65% preferably 75%, 85%, or 95% identical to the NBS domain encoding portion of SEQ ID NO:6; an isolated PYRIN-1 protein which is encoded by a nucleic acid molecule having a nucleotide sequence at least about 65% preferably 75%, 85%, or 95% identical to the kinase 1a, kinase 2, or kinase 3a region encoding portion of SEQ ID NO:6; an isolated PYRIN-1 protein which is encoded by a nucleic acid molecule having a nucleotide sequence at least about 65% preferably 75%, 85%, or 95% identical to the LRR domain encoding portion of SEQ ID NO:6 or one or more leucine rich repeat encoding portions of SEQ ID NO:6; and an isolated PYRIN-1 protein which is encoded by a nucleic acid molecule having a nucleotide sequence which hybridizes under stringent hybridization conditions to a nucleic acid molecule having the nucleotide sequence of SEQ ID NO:6.

The NBS-1 or PYRIN-1 nucleic acids, polypeptides, and antibodies of the invention may be useful for mapping the location of either the NBS-1 or PYRIN-1 genes.

Another embodiment of the invention features NBS-1 or PYRIN-1 nucleic acid molecules which specifically detect NBS-1 or PYRIN-1 nucleic acid molecules, relative to nucleic acid molecules encoding other members of the NBS/LRR superfamily. For example, in one embodiment, a NBS-1 or PYRIN-1 nucleic acid molecule hybridizes under stringent conditions to a nucleic acid molecule comprising the nucleotide sequence of SEQ ID NO:1, SEQ ID NO:3, SEQ ID NO:4, SEQ ID NO:6, or a complement thereof. In another embodiment, the NBS-1 or PYRIN-1 nucleic acid molecule is at least 300 (350, 400, 450, 500, 550, 600, 650, 700, 800, 900, 1000, 1100, 1200, 1300, 1400, 1500, 1600, 1800, 2000, 2250, 2500, 2750, 3000, 3250, 3500, 3750, or 3850) nucleotides in length and hybridizes under stringent conditions to a nucleic acid molecule comprising the nucleotide sequence shown in SEQ ID NO:1, SEQ ID NO:3, SEQ ID NO:4, SEQ ID NO:6, or a complement thereof. In another embodiment, an isolated NBS-1 or PYRIN-1 nucleic acid molecule comprises the pyrin domain encoding portion of SEQ ID NO:3, SEQ ID NO:6 or a complement thereof. In yet another embodiment, the invention provides an isolated nucleic acid molecule which is antisense to the coding strand of a NBS-1 or PYRIN-1 nucleic acid.

Another aspect of the invention provides a vector, e.g., a recombinant expression vector, comprising a NBS-1 or PYRIN-1 nucleic acid molecule of the invention. In another embodiment the invention provides a host cell containing such a vector. The invention also provides a method for producing NBS-1 or PYRIN-1 protein by culturing, in a suitable medium, a host cell of the invention containing a recombinant expression vector such that a NBS-1 or PYRIN-1 protein is produced.

Another aspect of this invention features isolated or recombinant NBS-1 or PYRIN-1 proteins and polypeptides. Preferred NBS-1 or PYRIN-1 proteins and polypeptides possess at least one biological activity possessed by naturally occurring human NBS-1 or PYRIN-1, e.g., (1) the ability to form protein:protein interactions with proteins in an apoptotic or inflammatory signaling pathway; (2) the ability to form pyrin domain-apoptotic domain interactions with proteins in an apoptotic or inflammatory signaling pathway, e.g., pyrin domain-pyrin domain, pyrin domain-CARD domain, or pyrin domain-death effector domain; (3) the ability to bind a NBS-1 or PYRIN-1 ligand; and (4) the ability to bind to an intracellular target. Other activities include: (1) modulation of cellular proliferation; (2) modulation of cellular differentiation; (3) modulation of cellular death; (4) modulation of ER-specific apoptosis pathways; (5) modulation of amyloid-$\beta$-mediated neurotoxicity; (6) modulation of the NF-kB pathway; and (7) modulation of stress-responsive signaling pathways.

The NBS-1 or PYRIN-1 proteins of the present invention, or biologically active portions thereof, can be operatively linked to a non-NBS-1 or PYRIN-1 polypeptide (e.g., heterologous amino acid sequences) to form NBS-1 or PYRIN-1 fusion proteins, respectively. The invention further features antibodies that specifically bind NBS-1 or PYRIN-1-proteins, such as-monoclonal or polyclonal antibodies. In addition, the NBS-1 or PYRIN-1 proteins or biologically active portions thereof can be incorporated into pharmaceutical compositions, which optionally include pharmaceutically acceptable carriers.

In another aspect, the present invention provides a method for detecting the presence of NBS-1 or PYRIN-1 activity or expression in a biological sample by contacting the biological sample with an agent capable of detecting an indicator of NBS-1 or PYRIN-1 activity such that the presence of NBS-1 or PYRIN-1 activity is detected in the biological sample.

In another aspect, the invention provides a method for modulating NBS-1 or PYRIN-1 activity comprising contacting a cell with an agent that modulates (inhibits or stimulates) NBS-1 or PYRIN-1 activity or expression such that NBS-1 or PYRIN-1 activity or expression in the cell is modulated. In one embodiment, the agent is an antibody that specifically binds to NBS-1 or PYRIN-1 protein. In another embodiment, the agent modulates expression of NBS-1 or PYRIN-1 by modulating transcription of a NBS-1 or PYRIN-1 gene, splicing of a NBS-1 or PYRIN-1 mRNA, or translation of a NBS-1 or PYRIN-1 mRNA. In yet another embodiment, the agent is a nucleic acid molecule having a nucleotide sequence that is antisense to the coding strand of the NBS-1 or PYRIN-1 mRNA or the NBS-1 or PYRIN-1 gene.

In one embodiment, the methods of the present invention are used to treat a subject having a disorder characterized by aberrant NBS-1 or PYRIN-1 protein or nucleic acid expression or activity or related to NBS-1 or PYRIN-1 expression or activity by administering an agent which is a NBS-1 or PYRIN-1 modulator to the subject. In one embodiment, the NBS-1 or PYRIN-1 modulator is a NBS-1 or PYRIN-1 protein. In another embodiment the NBS-1 or PYRIN-1 modulator is a NBS-1 or PYRIN-1 nucleic acid molecule. In other embodiments, the NBS-1 or PYRIN-1 modulator is a peptide, peptidomimetic, or other small molecule.

The present invention also provides a diagnostic assay for identifying the presence or absence of a genetic lesion or mutation characterized by at least one of: (i) aberrant modification or mutation of a gene encoding a NBS-1 or PYRIN-1 protein; (ii) mis-regulation of a gene encoding a NBS-1 or PYRIN-1 protein; (iii) aberrant RNA splicing; and (iv) aberrant post-translational modification of a NBS-1 or PYRIN-1 protein, wherein a wild-type form of the gene encodes a protein with a NBS-1 or PYRIN-1 activity.

In another aspect, the invention provides a method for identifying a compound that binds to or modulates the activity of a NBS-1 or PYRIN-1 protein. In general, such methods entail measuring a biological activity of a NBS-1 or PYRIN-1 protein in the presence and absence of a test compound and identifying those compounds that alter the activity of the NBS-1 or PYRIN-1 protein.

The invention also features methods for identifying a compound that modulates the expression of NBS-1 or PYRIN-1 by measuring the expression of NBS-1 or PYRIN-1 in the presence and absence of a compound.

The invention also features methods for treating disorders associated with inappropriate apoptosis (e.g., Alzheimer's diseases or other neurological disorders associated with neuronal apoptosis) by modulating the expression or activity of NBS-1 or PYRIN-1.

Other features and advantages of the invention will be apparent from the following detailed description and claims.

BRIEF DESCRIPTION OF THE DRAWINGS

FIGS. 1A-1E depict the cDNA sequence (SEQ ID NO:1) and the predicted amino acid sequence (SEQ ID NO:2) of human NBS-1. The open reading frame of human NBS-1 (SEQ ID NO:1) extends from nucleotide 78 to nucleotide 3176 of SEQ ID NO:1 (SEQ ID NO:3).

FIGS. 4A-4E depict the cDNA sequence (SEQ ID NO:4) and the predicted amino acid sequence (SEQ ID NO:5) of human PYRIN-1. The open reading frame of human PYRIN-1 (SEQ ID NO:4) extends from nucleotide 141 to nucleotide 3240 of SEQ ID NO:4 (SEQ ID NO:6).

FIGS. 8A-8H each depict the alignment of several of the leucine rich repeats within the LRR domain of NBS-1 ((amino acids 726-752 of SEQ ID NO:2 (FIG. 8A), amino acids 782-809 of SEQ ID NO:2 (FIG. 8B), amino acids 811-838 of SEQ ID NO:2 (FIG. 8C), amino acids 839-866 of SEQ ID NO:2 (FIG. 8D), amino acids 868-895 of SEQ ID NO:2 (FIG. 8E), amino acids 896-923 of SEQ ID NO:2 (FIG. 8F), amino acids 925-952 of SEQ ID NO:2 (FIG. 8G), and amino acids 953-979 of SEQ ID NO:2 (FIG. 8H)) with a consensus leucine rich repeat (SEQ ID NO:12) derived from a hidden Markov model. The leucine rich repeats at amino acids 670-697, 698-725, 754-781 and 981-1008 of SEQ ID NO:2 are not depicted.

FIGS. 10A-10I each depict the alignment of several of the leucine rich repeats within the LRR domain of PYRIN-1 ((amino acids 740-767 of SEQ ID NO:5 (FIG. 10A), amino acids 769-796 of SEQ ID NO:5 (FIG. 10B), amino acids 797-821 of SEQ ID NO:5 (FIG. 10C), amino acids 826-849 of SEQ ID NO:5 (FIG. 10D), amino acids 854-878 of SEQ ID NO:5 (FIG. 10E), amino acids 883-906 of SEQ ID NO:5 (FIG. 10F), amino acids 911-935 of SEQ ID NO:5 (FIG. 10G), amino acids 940-967 of SEQ ID NO:5 (FIG. 10H), and amino acids 968-991 of SEQ ID NO-5 (FIG. 10I)) with a consensus leucine rich repeat (SEQ ID NO:13) derived from a hidden Markov model.

DETAILED DESCRIPTION OF THE INVENTION

The present invention is based, in part, on the identification of a predicted mRNA sequence encoding human NBS-1 protein. A nucleotide sequence encoding a human NBS-1 protein is shown in FIGS. 1A-1E (SEQ ID NO:1; SEQ ID NO:3 includes the open reading frame only). A predicted amino acid sequence of human NBS-1 protein is also shown in FIGS. 1A-1E (SEQ ID NO:2).

The present invention is also based, in part, on the identification of a predicted mRNA sequence encoding human PYRIN-1 protein. A nucleotide sequence encoding a human PYRIN-1 protein is shown in FIGS. 4A-4E (SEQ ID NO:4; SEQ ID NO:6 includes the open reading frame only). A predicted amino acid sequence of human PYRIN-1 protein is also shown in FIGS. 4A-4E (SEQ ID NO:5).

Identification of Human NBS-1

A cDNA encoding human NBS-1 was identified by searching a proprietary cDNA sequence database in an effort to identify sequences that might encode an NBS. This search led to the identification of a cDNA that was used in 5' RACE to identify a complete open reading frame encoding the protein later named NBS-1.

FIGS. 1A-1E depict the sequence of a 3431 nucleotide cDNA (SEQ ID NO:1) which includes a predicted open reading frame (SEQ ID NO:3; nucleotides 78-3176 of SEQ ID NO:1) encoding a 1033 amino acid human NBS-1 protein (SEQ ID NO:2). Human NBS-1 is predicted to be an intracellular protein having a molecular weight of 113.6 kD, prior to post-translational modification.

The predicted amino acid sequence of human NBS-1 was compared to amino acid sequences of known proteins and various motifs were identified. The 1033 amino acid human NBS-1 protein includes five N-glycosylation sites (e.g., about amino acid residues 637-640, 679-682, 782-785, 789-952, and 952-955 of SEQ ID NO:2); 11 protein kinase C phosphorylation sites (amino acids 79-81, 105-107, 218-220, 307-309, 379-381, 563-565, 669-671, 806-808, 983-985, 986-988, and 1016-1018 of SEQ ID NO:2); 16 casein kinase II phosphorylation sites (amino acids 13-16, 55-58, 105-108, 218-221, 229-232, 512-515, 570-573, 584-587, 639-642, 643-646, 650-653, 669-672, 711-714, 791-794, 942-945, and 1027-1030 of SEQ ID NO:2); two tyrosine kinase phosphorylation sites (amino acids 317-325 and 858-866 of SEQ ID NO:2); and 10 N-myristoylation sites (amino acids 188-193, 266-271, 291-296, 367-372, 417-422, 446-451, 566-571, 675-680, 761-766 and 982-987 of SEQ ID NO:2)

Figure 2:
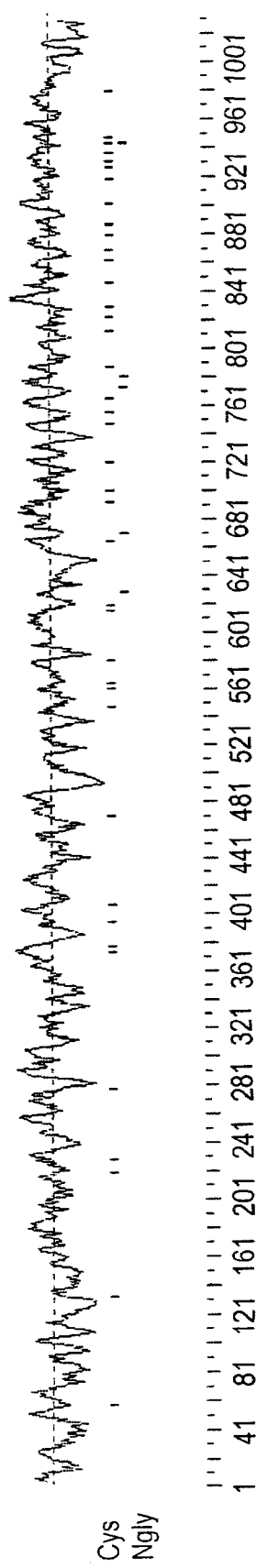
FIG. 2 depicts a hydropathy plot of human NBS-1. Relatively hydrophobic residues are above the dashed-horizontal line, and relatively hydrophilic residues are below the dashed horizontal line. The cysteine residues (cys) and potential N-glycosylation sites (Ngly) are indicated by short vertical lines just below the hydropathy trace.

FIG. 2 depicts a hydropathy plot of human NBS-1. Relatively hydrophobic residues are above the dashed horizontal line, and relatively hydrophilic residues are below the dashed horizontal line. Potential N-glycosylation sites (Ngly) and cysteine residues are indicated by short vertical lines just below the hydropathy trace.

Figure 3:
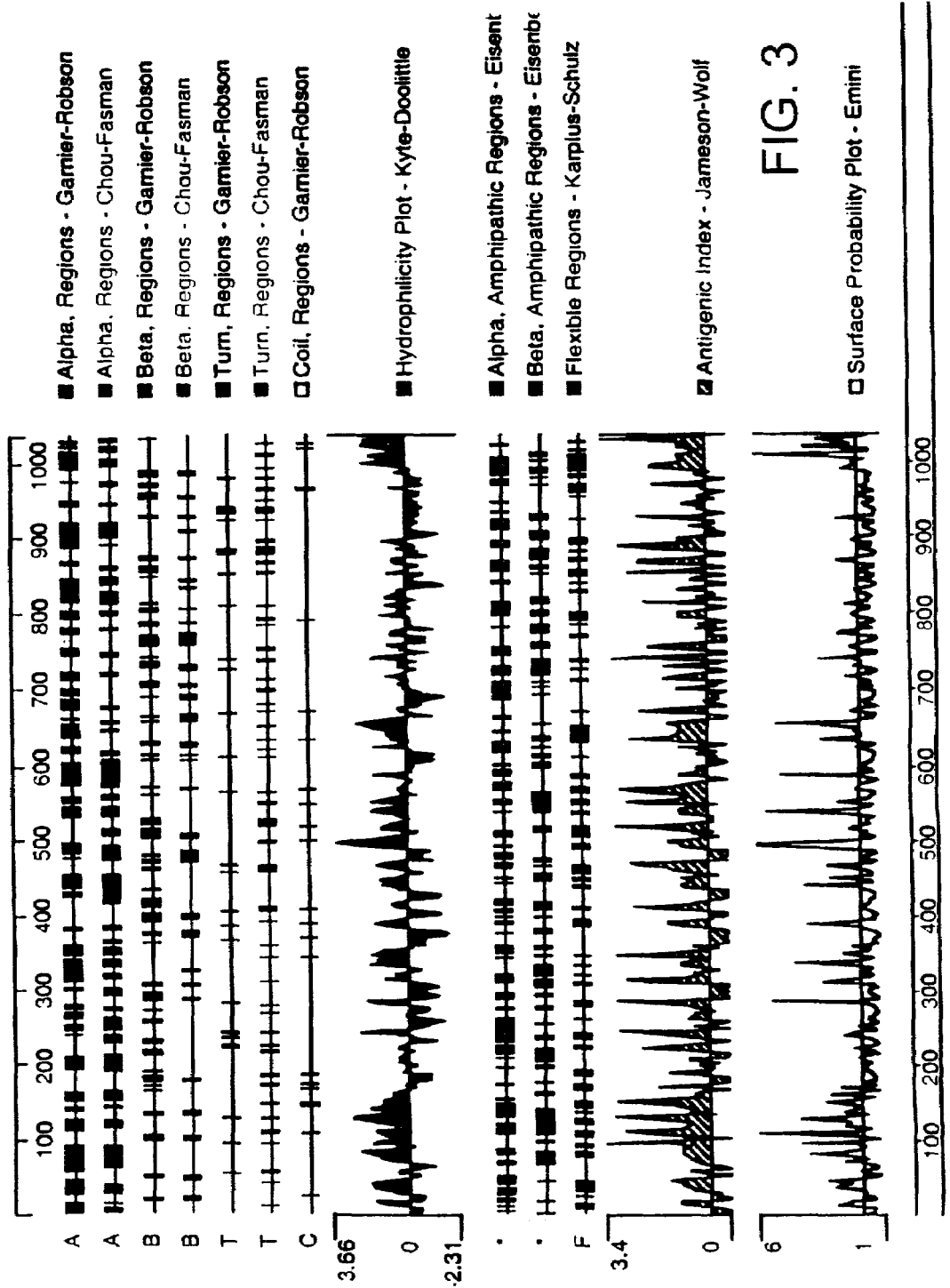
FIG. 3 depicts a plot showing the predicted structural features of a portion of human NBS-1. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

A plot showing the predicted structural features of a portion of human NBS-1 is presented in FIG. 3. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

Analysis of the predicted NBS-1 amino acid sequence showed it to contain a pyrin domain (about amino acids 3-79 of SEQ ID NO:2) a nucleotide binding site (NBS; about amino acid residues 174-605 of SEQ ID NO:2) and 12 leucine rich repeats (about amino acids residues 670-697, 698-725, 726-752, 754-781, 782-809, 811-838, 839-866, 868-895, 896-923, 925-952, 953-979, and 981-1008 of SEQ ID NO:2) which form a LRR domain (about amino acids 670-1008 of SEQ ID NO:2). Within the predicted NBS there is a kinase 1a domain (P-loop) (about amino acids 180-195 of SEQ ID NO:2), a kinase 2 domain (Walker B box) (about amino acids 249-264 of SEQ ID NO:2), and a kinase 3a domain (about amino acids 302-313 of SEQ ID NO:2).

Figure 7:
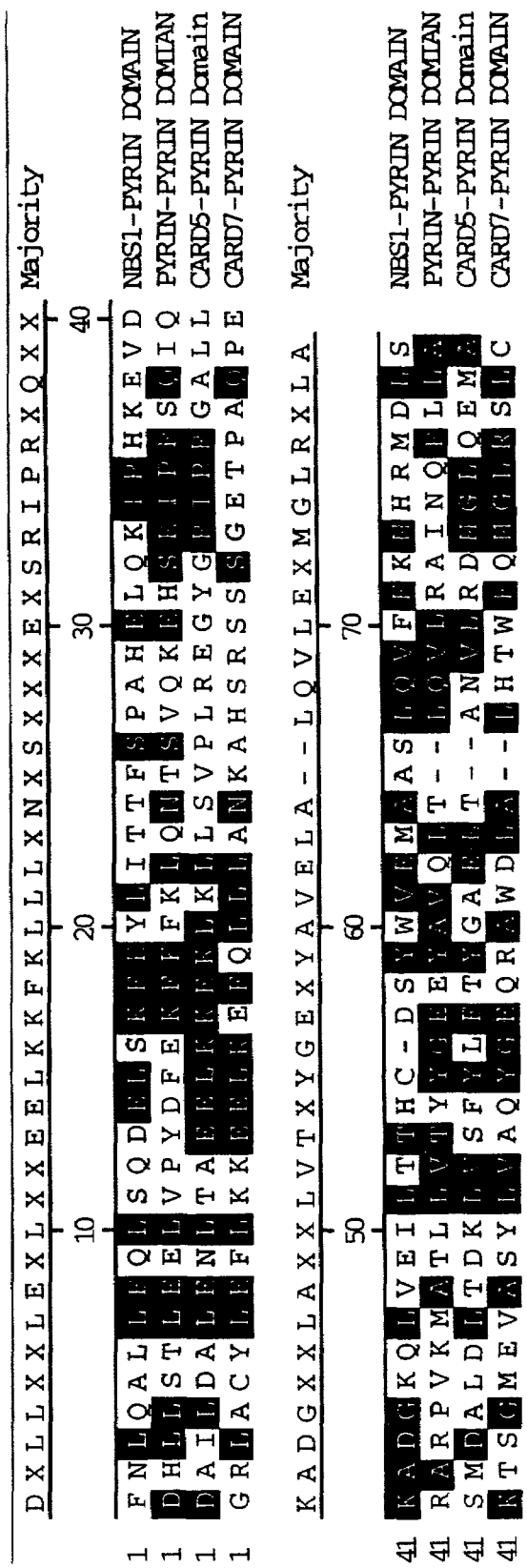
FIG. 7 depicts an alignment of amino acids 3-79 of human NBS-1 (amino acid residues 3-79 of SEQ ID NO:2) with the pyrin domains of pyrin (SEQ ID NO:7), CARD-5 (SEQ ID NO:8), and CARD-7 (SEQ ID NO:9). A consensus pyrin domain sequence (SEQ ID NO:10) is shown above the alignment.

FIG. 7 depicts an alignment of amino acids 3-79 of human NBS-1 (amino acid residues 3-79 of SEQ ID NO:2) with the pyrin domains of pyrin (SEQ ID NO:7), CARD-5 (SEQ ID NO:8), and CARD-7 (SEQ ID NO:9). A consensus pyrin domain sequence (SEQ ID NO:10) is shown above the alignment.

FIGS. 8A-8H each depict an alignment of individual leucine rich repeats within the LRR domain of NBS-1 ((amino acids 726-752 of SEQ ID NO:2 (FIG. 8A), amino acids 782-809 of SEQ ID NO:2 (FIG. 8B), amino acids 811-838 of SEQ ID NO:2 (FIG. 8C), amino acids 839-866 of SEQ ID NO:2 (FIG. 8D), amino acids 868-895 of SEQ ID NO:2 (FIG. 8E), amino acids 896-923 of SEQ ID NO:2 (FIG. 8F), amino acids 925-952 of SEQ ID NO:2 (FIG. 8G), and amino acids 953-979 of SEQ ID NO:2 (FIG. 8H)) with a consensus LRR (SEQ ID NO:12) derived from a hidden Markov model. The leucine rich repeats present at amino acids 670-697, 698-725, 754-78 1 and 981-1008 of SEQ ID NO:2 are not depicted in FIGS. 8A-8H. HMMs can be used to do multiple sequence alignment and very sensitive database searching, using statistical descriptions of a sequence family's consensus. For more information on HMM searches, see the HIMMer website at Washineton University St. Louis. In the alignments of FIGS. 8A-8H a single letter amino acid designation on the line between the NBS-1 sequence and the HMM-generated consensus sequence indicates an exact match between the two. A "+" on this middle Line indicates a conservative substitution at the particular residue of NBS-1.

Identification of Human PYRIN-1

A cDNA encoding human PYRIN-1 was identified by searching a proprietary cDNA sequence database with a sequence encoding the pyrin domain of NBS-1. This search led to the identification of a cDNA (clone jthPa091c07t1) from a human placenta library encoding a protein that was named PYRIN-1.

FIGS. 4A-4E depict the sequence of a 3857 nucleotide cDNA (SEQ ID NO:4) which includes a predicted open reading frame (SEQ ID NO:6; nucleotides 141-3240 of SEQ ID NO:4) encoding a 1034 amino acid human PYRIN-1 protein (SEQ ID NO:5). Human PYRIN-1 is predicted to be an intracellular protein.

The predicted amino acid sequence of human PYRIN-1 was compared to amino acid sequences of known proteins and various motifs were identified. The 1034 amino acid human PYRIN-1 protein includes three N-glycosylation sites (e.g., about amino acid residues 654-657, 911-914, and 950-953 of SEQ ID NO:5); four cAMP- and cGMP-dependent protein kinase phosphorylation sites (e.g., about amino acid residues 164-167, 290-29-3-, 592-595, and 970-973 of SEQ ID NO:5); nine protein kinase C phosphorylation sites (e.g., about amino acid residues 3-5, 44-46, 266-268, 347-349, 426-428, 433-435, 595-597, 656-658, and 968-970 of SEQ ID NO:5); 12 casein kinase II phosphorylation sites (e.g., about amino acid residues 110-113, 177-180, 269-272, 522-525, 588-591, 624-627, 657-660, 740-743, 750-753, 921-924, 1014-1017, and 1018-1021 of SEQ ID NO:5); six N-myristoylation sites (e.g., about amino acid residues 93-98, 227-232, 491-496, 717-722, 888-893, and 919-924 of SEQ ID NO:5); an RGD cell attachment sequence (e.g., about amino acid residues 325-327 of SEQ ID NO:5); an ATP/GTP-binding site motif A (P-loop) (e.g., about amino acid residues 224-231 of SEQ ID NO:5); a leucine zipper pattern (e.g., about amino acid residues 816-837 of SEQ ID NO:5); a peroxisomal targeting signal (e.g., about amino acid residues 618-626 of SEQ ID NO:5); and 10 dileucine motifs (e.g., about amino acid residues 448-449, 533-534, 559-560, 606-607, 815-816, 823-824, 929-930, 934-935, 962-963, and 997-998 of SEQ ID NO:5).

Figure 5:
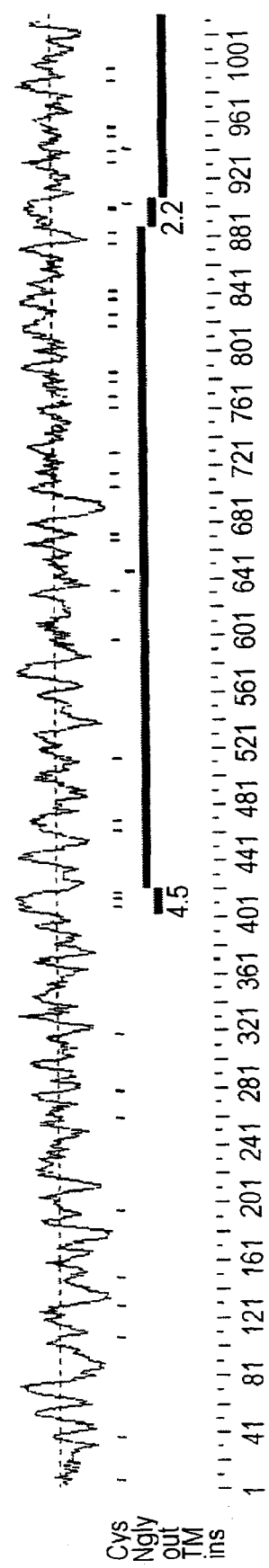
FIG. 5 depicts a hydropathy plot of a poxion of human PYRIN-1. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.

FIG. 5 depicts a hydropathy plot of human PYRIN-1. Relatively hydrophobic residues are above the dashed horizontal line, and relatively hydrophilic residues are below the dashed horizontal line. Potential N-glycosylation sites (Ngly) and cysteine residues are indicated by short vertical lines just below the hydropathy trace.

Figure 6:
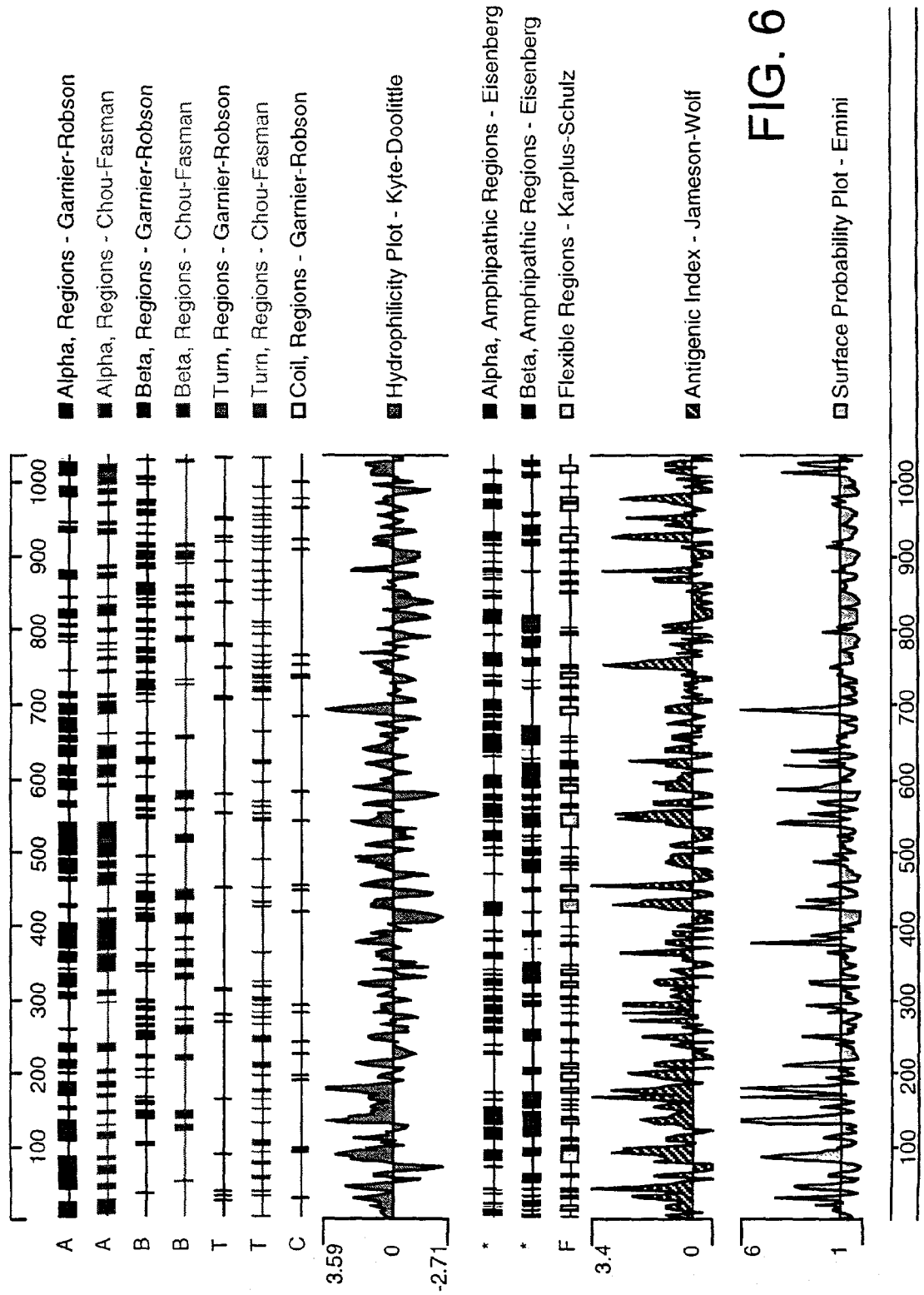
FIG. 6 depicts a plot showing the predicted structural features of a portion of human PYRIN-1. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

A plot showing the predicted structural features of human PYRIN-1 is presented in FIG. 6. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

Analysis of the predicted PYRIN-1 amino acid sequence showed it to contain a pyrin domain (about amino acids 1-87 of SEQ ID NO:5) a nucleotide binding site (NBS; about amino acid residues 263-357 of SEQ ID NO:5) and nine leucine rich repeats (LRRS; about amino acids residues 740-767, 769-796, 797-821, 826-849, 854-878, 883-906, 911-935, 940-967, and 968-991 of SEQ ID NO:5) which form a LRR domain (about amino acids 740-991 of SEQ ID NO:5). Within the predicted NBS there is a kinase 1a domain (P-loop) (about amino acids 224-233 of SEQ ID NO:5), a kinase 2 domain (Walker B box) (about amino acids 290-306 of SEQ ID NO:5), and a kinase 3a domain (about amino acids 344-355 of SEQ ID NO:5).

Figure 9:
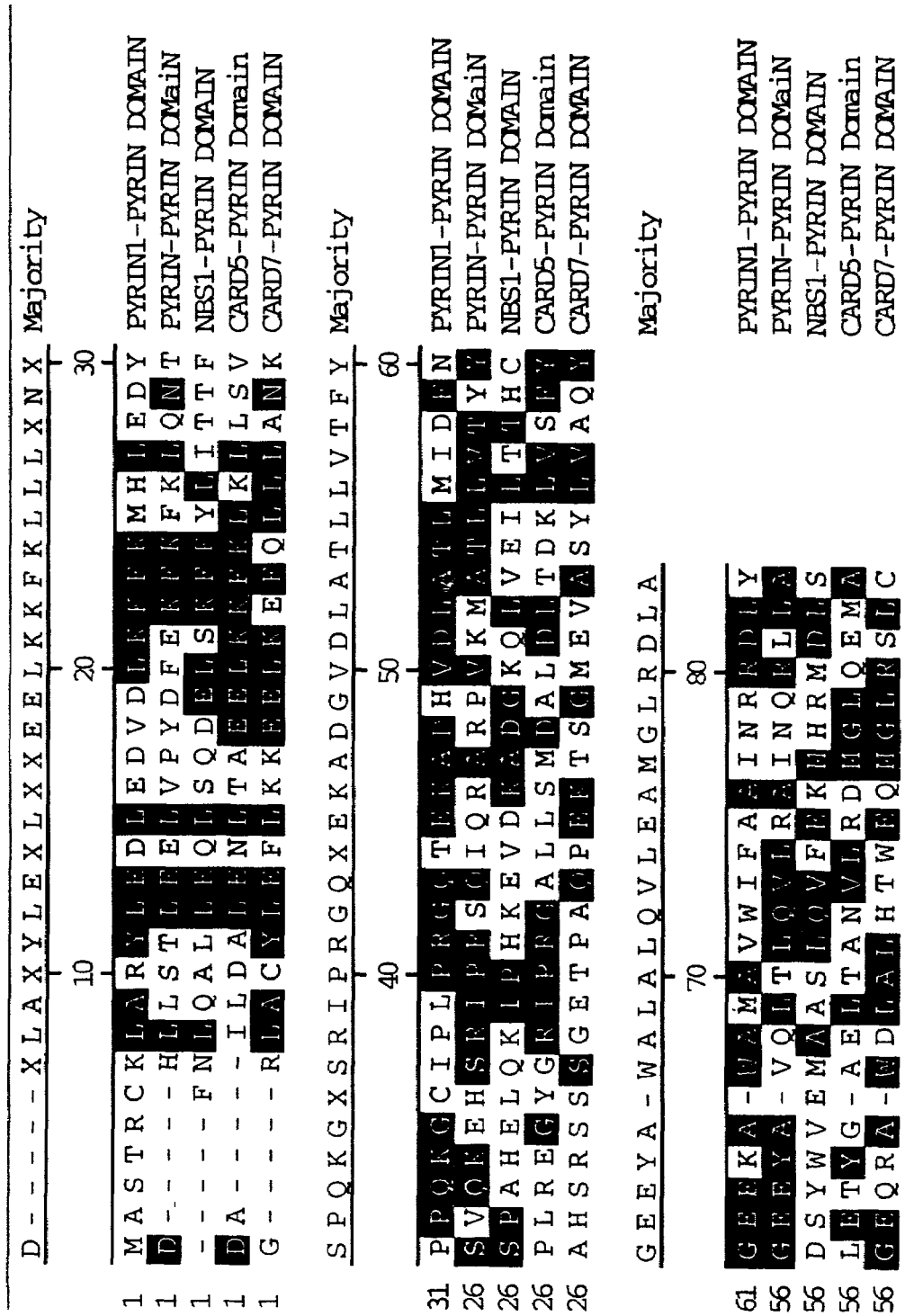
FIG. 9 depicts an alignment of amino acids 1-82 of human PYRIN-1 (amino acid residues 1-82 of SEQ ID NO:5) with the pyrin domains of pyrin (SEQ ID NO:7), CARD-5 (SEQ ID NO:8), and CARD-7 (SEQ ID NO:9). A consensus pyrin domain sequence (SEQ ID NO:11) is shown above the alignment.

FIG. 9 depicts an alignment of amino acids 1-82 of human PYRIN-1 (amino acid residues 1-82 of SEQ ID NO:5) with the pyrin domains of pyrin (SEQ ID NO:7), CARD-5 (SEQ ID NO:8), and CARD-7 (SEQ ID NO:9). A consensus pyrin domain sequence (SEQ ID NO:11) is shown above the alignment.

FIGS. 10A-10I each depict an alignment of individual leucine rich repeats within the LRR domain of PYRIN-1 ((about amino acids 740-767 of SEQ ID NO:5 (FIG. 10A), amino acids 769-796 of SEQ ID NO:5 (FIG. 10B), amino acids 797-821 of SEQ ID NO:5 (FIG. 10C), amino acids 826-849 of SEQ ID NO:5 (FIG. 10D), amino acids 854-878 of SEQ ID NO:5 (FIG. 10E), amino acids 883-906 of SEQ ID NO:5 (FIG. 10F), amino acids 911-935 of SEQ ID NO:5 (FIG. 10G), amino acids 940-967 of SEQ ID NO:5 (FIG. 10H), and amino acids 968-991 of SEQ ID NO:5 (FIG. 10I)) with a consensus LRR (SEQ ID NO:13) derived from a hidden Markov model.

TABLE 1

Summary of Human NBS-1 and Human PYRIN-1 Sequence Information

| Gene | cDNA | Protein | ORF | Figure |
| --- | --- | --- | --- | --- |
| Human NBS-1 | SEQ ID NO:1 | SEQ ID NO:2 | SEQ ID NO:3 | FIGS. 1A-E |
| Human PYRIN-1 | SEQ ID NO:4 | SEQ ID NO:5 | SEQ ID NO:6 | FIGS. 4A-4E | structural domain and having sufficient amino acid or nucleotide sequence identity as defined herein. Such family members can be naturally occurring and can be from either the same or different species. For example, a family can contain a first protein of human origin and a homologue of that protein of murine origin, as well as a second, distinct protein of human origin and a murine homologue of that protein. Members of a family may also have common functional characteristics.

Preferred NBS-1 or PYRIN-1 polypeptides of the present invention include an amino acid sequence sufficiently identical to one or more of the following domains: a pyrin domain, and NBS domain, and a LRR domain.

As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences have a common structural domain and/or common functional activity. For example, amino acid or nucleotide sequences which contain a common structural domain having about 65% identity, preferably 75% identity, more preferably 85%, 95%, or 98% identity are defined herein as sufficiently identical.

As used interchangeably herein a "NBS-1 or PYRIN-1 activity", "biological activity of NBS-1 or PYRIN-1" or "functional activity of NBS-1 or PYRIN-1", refers to an activity exerted by a NBS-1 or PYRIN-1 protein, polypeptide or nucleic acid molecule on a NBS-1 or PYRIN-1 responsive cell as determined in vivo, or in vitro, according to standard techniques. NBS-1 or PYRIN-1 may act as a pro-apoptotic protein or an anti-apoptotic protein (i.e., it might act to decrease or increase apoptosis). A NBS-1 or PYRIN-1 activity can be a direct activity, such as an association with or an enzymatic activity on a second protein

TABLE 2

Summary of Domains of NBS-1 and PYRIN-1

| Domain | Location in NBS-1 | Location in PYRIN-1 |
| --- | --- | --- |
| Pyrin domain | about amino acid residues 3-79 of SEQ ID NO:2 | about amino acid residues 1-87 of SEQ ID NO:5 |
| NBS domain | about amino acid residues 174-605 of SEQ ID NO:2 | about amino acid residues 263-357 of SEQ ID NO:5 |
| Kinase 1a domain (P-loop) | about amino acid residues 180-195 of SEQ ID NO:2 | about amino acid residues 224-233 of SEQ ID NO:5 |
| Kinase 2 domain (Walker B box) | about amino acid residues 249-264 of SEQ ID NO:2 | about amino acid residues 290-306 of SEQ ID NO:5 |
| Kinase 3a domain | about amino acid residues 302-313 of SEQ ID NO:2 | about amino acid residues 344-355 of SEQ ID NO:5 |
| Leucine rich repeats | about amino acids residues 670-697, 698-725, 726-752, 754-781, 782-809, 811-838, 839-866, 868-895, 896-923, 925-952, 953-979, and 981-1008 of SEQ ID NO:2 | about amino acids residues 740-767, 769-796, 797-821, 826-849, 854-878, 883-906, 911-935, 940-967, and 968-991 of SEQ ID NO:5 |
| LRR domain | about amino acid residues 670-1008 of SEQ ID NO:2 | about amino acid residues 740-991 of SEQ ID NO:5 |

Each of NBS-1 and PYRIN-1 are members of a family of molecules (NBS-1 and PYRIN-1 families, respectively) having certain conserved structural and functional features. The term "family" when referring to the protein and nucleic acid molecules of the invention is intended to mean two or more proteins or nucleic acid molecules having a common or an indirect activity, such as a cellular signaling activity mediated by interaction of the NBS-1 or PYRIN-1protein with a second protein.

In one embodiment, a NBS-1 or PYRIN-1 activity can include at least one or more of the following activities: (i) the ability to interact with proteins in an apoptotic or inflammatory signaling pathway (ii) the ability to interact with a NBS-1 or PYRIN-1; (iii) the ability to interact with an intracellular target protein; (iv) the ability to interact, directly or indirectly, with one or more with proteins having a pyrin domain, a CARD domain or other domain associated with apoptotic or inflammatory signaling; (v) the ability to modulate, directly or indirectly, the activity of a caspase, e.g., caspase-9; (vi) the ability to modulate of ER-specific apoptosis pathways; (vii) the ability to modulate, directly or indirectly, the activity of NF-kB; (viii) the ability to modulate, directly or indirectly, Apaf-1; (ix) the ability to interact, directly or indirectly, with a Bcl-2 family member; (x) the ability to modulate, directly or indirectly, the activity of a stress activated kinase (e.g., JNK/p38); and (xi) the ability to modulate, directly or indirectly, phosphorylation of CHOP (GADD 153). NBS-1 or PYRIN-1 nucleic acids and polypeptides as well as modulators of activity or expression of NBS-1 or PYRIN-1 might be used to modulate an Apaf-1 signaling pathway.

Accordingly, another embodiment of the invention features isolated NBS-1 or PYRIN-1 proteins and polypeptides having a NBS-1 or PYRIN-1 activity.

Various aspects of the invention are described in further detail in the following subsections.

I. Isolated Nucleic Acid Molecules

One aspect of the invention pertains to isolated nucleic acid molecules that encode NBS-1 or PYRIN-1 proteins or biologically active portions thereof, as well as nucleic acid molecules sufficient for use as hybridization probes to identify NBS-1 or PYRIN-1-encoding nucleic acids (e.g., NBS-1 or PYRIN-1 mRNA) and fragments for use as PCR primers for the amplification or mutation of NBS-1 or PYRIN-1 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences (preferably protein encoding sequences) that which naturally flank the nucleic acid (i.e., sequences located at the 5' and 3' ends of the nucleic acid) in the genomic DNA of the organism from which the nucleic acid is derived. For example, in various embodiments, the isolated NBS-1 or PYRIN-1 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, SEQ ID NO:4, SEQ ID NO:6, or a complement of any of these nucleotide sequences, can be isolated using standard molecular biology techniques and the sequence information provided herein. Using all or portion of the nucleic acid sequences of SEQ ID NO:1, SEQ ID NO:3, SEQ ID NO:4 or SEQ ID NO:6, as a hybridization probe, NBS-1 or PYRIN-1 nucleic acid molecules can be isolated using standard hybridization and cloning techniques (e.g., as described in Sambrook et al., eds., Molecular Cloning: A Laboratory Manual. 2nd, ed., Cold Spring Harbor Laboratory, Cold Spring Harbor Laboratory Press, Cold Spring Harbor, N.Y., 1989).

A nucleic acid of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to NBS-1 or PYRIN-1 nucleotide sequences can be prepared by standard synthetic techniques, e.g., using an automated DNA synthesizer.

In another embodiment, an isolated nucleic acid molecule of the invention comprises a nucleic acid molecule which is a complement of the nucleotide sequence shown in SEQ ID NO:1, SEQ ID NO:3, SEQ ID NO:4, SEQ ID NO:6, or a portion thereof. A nucleic acid molecule which is complementary to a given nucleotide sequence is one which is sufficiently complementary to the given nucleotide sequence that it can hybridize to the given nucleotide sequence thereby forming a stable duplex.

Moreover, the nucleic acid molecule of the invention can comprise only a portion of a nucleic acid sequence encoding NBS-1 or PYRIN-1, for example, a fragment which can be used as a probe or primer or a fragment encoding a biologically active portion of NBS-1 or PYRIN-1. The nucleotide sequence determined from the cloning of the NBS-1 or PYRIN-1 gene allows for the generation of probes and primers designed for use in identifying and/or cloning NBS-1 or PYRIN-1 homologues in other cell types, e.g., from other tissues, as well as NBS-1 or PYRIN-1 homologues and orthologs from other mammals. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense sequence of SEQ ID NO:1, SEQ ID NO:3, SEQ ID NO:4, SEQ ID NO:6, or of a naturally occurring mutant of one of SEQ ID NO:1, SEQ ID NO:3, SEQ ID NO:4 or SEQ ID NO:6.

Probes based on the NBS-1 or PYRIN-1 nucleotide sequence can be used to detect transcripts or genomic sequences encoding the same or similar proteins. The probe comprises a label group attached thereto, e.g., a radioisotope, a fluorescent compound, an enzyme, or an enzyme co-factor. Such probes can be used as a part of a diagnostic test kit for identifying allelic variants and orthologs of the NBS-1 or PYRIN-1 proteins of the present invention, identifying cells or tissue which mis-express a NBS-1 or PYRIN-1 protein, such as by measuring a level of a NBS-1 or PYRIN-1-encoding nucleic acid in a sample of cells from a subject, e.g., detecting NBS-1 or PYRIN-1 mRNA levels or determining whether a genomic NBS-1 or PYRIN-1 gene has been mutated or deleted.

A nucleic acid fragment encoding a "biologically active portion" of NBS-1 or PYRIN-1 can be prepared by isolating a portion of SEQ ID NO:1, SEQ ID NO:3, SEQ ID NO:4 or SEQ ID NO:6, which encodes a polypeptide having a NBS-1 or PYRIN-1 biological activity, expressing the encoded portion of NBS-1 or PYRIN-1 protein (e.g., by recombinant expression in vitro) and assessing the activity of the encoded portion of NBS-1 or PYRIN-1.

The invention further encompasses nucleic acid molecules that differ from the nucleotide sequence of SEQ ID NO:1, SEQ ID NO:3, SEQ ID NO:4 and SEQ ID NO:6, due to degeneracy of the genetic code and thus encode the same NBS-1 or PYRIN-1 protein as that encoded by the nucleotide sequence shown in SEQ ID NO:1, SEQ ID NO:3, SEQ ID NO:4 or SEQ ID NO:6.

In addition to the NBS-1 or PYRIN-1 nucleotide sequence shown in SEQ ID NO:1, SEQ ID NO:3, SEQ ID NO:4 and SEQ ID NO:6, it will be appreciated by those skilled in the art that DNA sequence polymorphisms that lead to changes in the amino acid sequences of NBS-1 or PYRIN-1 may exist within a population (e.g., the human population). Such genetic polymorphism in the NBS-1 or PYRIN-1 gene may exist among individuals within a population due to natural allelic variation. As used herein, the terms "gene" and "recombinant gene" refer to nucleic acid molecules comprising an open reading frame encoding a NBS-1 or PYRIN-1 protein, preferably a mammalian NBS-1 or PYRIN-1 protein. Such natural allelic variations can typically result in 1-5% variance in the nucleotide sequence of the NBS-1 or PYRIN-1 gene. Any and all such nucleotide variations and resulting amino acid polymorphisms in NBS-1 or PYRIN-1 that are the result of natural allelic variation and that do not alter the functional activity of NBS-1 or PYRIN-1 are intended to be within the scope of the invention. Thus, e.g., 1%, 2%, 3%, 4%, or 5% of the amino acids in NBS-1 or PYRIN-1 (e.g., 1, 2, 3, 4, 5, 6, 8, 10, 15, or 17 amino acids) are replaced by another amino acid, preferably by conservative substitution.

Moreover, nucleic acid molecules encoding NBS-1 or PYRIN-1 proteins from other species (NBS-1 or PYRIN-1 orthologslhomologues), which have a nucleotide sequence which differs from that of a NBS-1 or PYRIN-1 disclosed herein, are intended to be within the scope of the invention.

Accordingly, in another embodiment, an isolated nucleic acid molecule of the invention is at least 150 (300, 325, 350, 375, 400, 425, 450, 500, 550, 600, 650, 700, 800, 900, 1000, 1100, 1200, 1300, 1400, 1500, 1600, 1800, 2000, 2250, 2500, 2750, 3000, 3250, 3500, 3750, or 3850) nucleotides in length and hybridizes under stringent conditions to the nucleic acid molecule comprising the nucleotide sequence, preferably the coding sequence, of SEQ ID NO:1, SEQ ID NO:3, SEQ ID NO:4 or SEQ ID NO:6.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1-6.3.6. An, non-limiting example of stringent hybridization conditions are hybridization in 6× sodium chloride/sodium citrate (SSC) at about 45° C., followed by one or more washes in 0.2×SSC, 0.1% SDS at 50-65° C. (e.g., 50° C. or 60° C. or 65° C.). Preferably, the isolated nucleic acid molecule of the invention that hybridizes under stringent conditions corresponds to a naturally-occurring nucleic acid molecule. As used herein, a "naturally-occurring" nucleic acid molecule refers to an RNA or DNA molecule having a nucleotide sequence that occurs in a human cell in nature (e.g., encodes a natural protein).

In addition to naturally-occurring allelic variants of the NBS-1 or PYRIN-1 sequence that may exist in the population, the skilled artisan will further appreciate that changes can be introduced by mutation into the nucleotide sequence of SEQ ID NO:1, SEQ ID NO:3, SEQ ID NO:4 or SEQ ID NO:6, thereby leading to changes in the amino acid sequence of the encoded protein without altering the functional ability of the protein. For example, one can make nucleotide substitutions leading to amino acid substitutions at "non-essential" amino acid residues. A "non-essential" amino acid residue is a residue that can be altered from the wild-type sequence of NBS-1 or PYRIN-1 protein without altering the biological activity, whereas an "essential" amino acid residue is required for biological activity. For example, amino acid residues that are conserved among the NBS-1 or PYRIN-1, proteins of various species are predicted to be particularly unamenable to alteration.

For example, preferred NBS-1 or PYRIN-1 proteins of the present invention contain at least one domain identified herein. Such conserved domains are less likely to be amenable to mutation. Other amino acid residues, however, (e.g., those that are not conserved or only semi-conserved among NBS-1 or PYRIN-1 of various species) may not be essential for activity and thus are likely to be amenable to alteration.

Accordingly, another aspect of the invention pertains to nucleic acid molecules encoding NBS-1 or PYRIN-1 proteins that contain changes in amino acid residues that are not essential for activity. Such NBS-1 or PYRIN-1 proteins differ in amino acid sequence from SEQ ID NO:2 or SEQ ID NO:5 and yet retain biological activity. In one embodiment, the isolated nucleic acid molecule includes a nucleotide sequence encoding a protein that includes an amino acid sequence that is at least about 45% identical, 65%, 75%, 85%, 95%, or 98% identical to the amino acid sequence of SEQ ID NO:2 or SEQ ID NO:5. An isolated nucleic acid molecule encoding a NBS-1 or PYRIN-1 protein having a sequence which differs from that of SEQ ID NO:1, SEQ ID NO:3, SEQ ID NO:4 or SEQ ID NO:6, can be created by introducing one or more nucleotide substitutions, additions or deletions into the nucleotide sequence of NBS-1 or PYRIN-1 (SEQ ID NO:1, SEQ ID NO:3, SEQ ID NO:4 or SEQ ID NO:6) such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. Thus, for example, 1%, 2%, 3%, 5%, or 10% of the amino acids can be replaced by conservative substitution. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, seine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in NBS-1 or PYRIN-1 is preferably replaced with another amino acid residue from the same side chain family. Alternatively, mutations can be introduced randomly along all or part of a NBS-1 or PYRIN-1 coding sequence, such as by saturation mutagenesis, and the resultant mutants can be screened for NBS-1 or PYRIN-1 biological activity to identify mutants that retain activity. Following mutagenesis, the encoded protein can be expressed recombinantly and the activity of the protein can be determined.

In an embodiment, a mutant NBS-1 or PYRIN-1 protein can be assayed for: (1) the ability to form protein:protein interactions with proteins in the apoptotic signaling pathway; (2) the ability to bind a NBS-1 or PYRIN-1 ligand; or (3) the ability to bind to an intracellular target protein.

The present invention encompasses antisense nucleic acid molecules, i.e., molecules which are complementary to a sense nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire NBS-1 or PYRIN-1 coding strand, or to only a portion thereof, e.g., all or part of the protein coding region (or open reading frame). An antisense nucleic acid molecule can be antisense to a noncoding region of the coding strand of a nucleotide sequence encoding NBS-1 or PYRIN-1. The noncoding regions ("5' and 3' untranslated regions") are the 5' and 3' sequences that flank the coding region and are not translated into amino acids. Given the coding strand sequences encoding NBS-1 or PYRIN-1 disclosed herein, antisense nucleic acids of the invention can be designed according to the rules of Watson and Crick base pairing. The antisense nucleic acid molecule can be complementary to the entire coding region of NBS-1 or PYRIN-1 mRNA, but more preferably is an oligonucleotide which is antisense to only a portion of the coding or noncoding region of NBS-1 or PYRIN-1 mRNA. For example, the antisense oligonucleotide can be complementary to the region surrounding the translation start site of NBS-1 or PYRIN-1 mRNA. An antisense oligonucleotide can be, for example, about 5, 10, 15, 20, 25, 30, 35, 40, 45 or 50 nucleotides-in-length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a NBS-1 or PYRIN-1 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An antisense nucleic acid molecule of the invention can be administered by direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625-6641). The antisense nucleic acid molecule can also comprise a 2'-o-methylribonucleotide (Inoue et al. (1987) Nucleic Acids Res. 15:6131-6148) or a chimeric RNA-DNA analogue (Inoue et al. (1987) FEBS Lett. 215:327-330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585-591)) can be used to catalytically cleave NBS-1 or PYRIN-1 mRNA transcripts to thereby inhibit translation of NBS-1 or PYRIN-1 mRNA. A ribozyme having specificity for a NBS-1 or PYRIN-1-encoding nucleic acid can be designed based upon the nucleotide sequence of a NBS-1 or PYRIN-1 cDNA disclosed herein. For example, a derivative of a Tetrahymena L-19 IVS RNA can be constructed in which the nucleotide sequence of the active site is complementary to the nucleotide sequence to be cleaved in a NBS-1 or PYRIN-1-encoding mRNA. See, e.g., Cech et al. U.S. Pat. No. 4,987,071; and Cech et al. U.S. Pat. No. 5,116,742. Alternatively, NBS-1 or PYRIN-1 mRNA can be used to select a catalytic RNA having a specific ribonuclease activity from a pool of RNA molecules. See, e.g., Bartel and Szostak (1993) Science 261:1411-1418.

The invention also encompasses nucleic acid molecules which form triple helical structures. For example, NBS-1 or PYRIN-1 gene expression can be inhibited by targeting nucleotide sequences complementary to the regulatory region of the NBS-1 or PYRIN-1 (e.g., the NBS-1 or PYRIN-1 promoter and/or enhancers) to form triple helical structures that prevent transcription of the NBS-1 or PYRIN-1 gene in target cells. See generally, Helene (1991) Anticancer Drug Des. 6(6):569-84; Helene (1992) Ann. N.Y. Acad. Sci. 660:27-36; and Maher (1992) Bioassays 14(12): 807-15.

In embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorganic Medicinal Chemistry 4(1):5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. (1996) Proc. Natl. Acad. Sci. USA 93:14670-675.

PNAs of NBS-1 or PYRIN-1 can be used for therapeutic and diagnostic applications. For example, PNAs can be used as antisense or antigene agents for sequence-specific modulation of gene expression by, e.g., inducing transcription or translation arrest or inhibiting replication. PNAs of NBS-1 or PYRIN-1 can also be used, e.g., in the analysis of single base pair mutations in a gene by, e.g., PNA directed PCR clamping; as artificial restriction enzymes when used in combination with other enzymes, e.g., S1 nucleases (Hyrup (1996) supra; or as probes or primers for DNA sequence and hybridization (Hyrup (1996) supra; Perry-O'Keefe et al. (1996) Proc. Natl. Acad. Sci. USA 93: 14670-675).

In another embodiment, PNAs of NBS-1 or PYRIN-1 can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of NBS-1 or PYRIN-1 can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) supra). The synthesis of PNA-DNA chimeras can be performed as described in Hyrup (1996) supra and Finn et al. (1996) Nucleic Acids Research 24(17):3357-63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag et al. (1989) Nucleic Acid Res. 17:5973-88). PNA monomers are then coupled in a stepwise manner to produce a chimeric molecule with a 5' PNA segment and a 3' DNA segment (Finn et al. (1996) Nucleic Acids Research 24(17):3357-63). Alternatively, chimericmolecules can be synthesized with a 5' DNA segment and a 3' PNA segment (Peterser et al. (1975) Bioorganic Med. Chem. Lett. 5:1119-11124).

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553-6556; Lemaitre et al. (1987) Proc. Natl. Acad. Sci. USA 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) Bio/Techniques 6:958-976) or intercalating agents (see, e.g., Zon (1988) Pharm. Res. 5:539-549). To this end, the oligonucleotide may be conjugated to another molecule, e.g., a peptide, hybridization triggered cross-linking agent, transport agent, hybridization-triggered cleavage agent, etc.

II. Isolated NBS-1 or PYRIN-1 Proteins and Anti-NBS-1 or PYRIN-1 Antibodies.

One aspect of the invention pertains to isolated NBS-1 or PYRIN-1 proteins, and biologically active portions thereof, as well as polypeptide fragments suitable for use as immunogens to raise anti-NBS-1 or PYRIN-1 antibodies. In one embodiment, native NBS-1 or PYRIN-1 proteins can be isolated from cells or tissue sources by an appropriate purification scheme using standard protein purification techniques. In another embodiment, NBS-1 or PYRIN-1 proteins are produced by recombinant DNA techniques. Alternative to recombinant expression, a NBS-1 or PYRIN-1 protein or polypeptide can be synthesized chemically using standard peptide synthesis techniques.

An "isolated" or "purified" protein or biologically active portion thereof is substantially free of cellular material or other contaminating proteins from the cell or tissue source from which the NBS-1 or PYRIN-1 protein is derived, or substantially free from chemical precursors or other chemicals when chemically synthesized. The language "substantially free of cellular material" includes preparations of NBS-1 or PYRIN-1 protein in which the protein is separated from cellular components of the cells from which it is isolated or recombinantly produced. Thus, NBS-1 or PYRIN-1 protein that is substantially free of cellular material includes preparations of NBS-1 or PYRIN-1 protein having less than about 30%, 20%, 10%, or 5% (by dry weight) of non- NBS-1 or PYRIN-1 protein (also referred to herein as a "contaminating protein"). When the NBS-1 or PYRIN-1 protein or biologically active portion thereof is recombinantly produced, it is also preferably substantially free of culture medium, i.e., culture medium represents less than about 20%, 10%, or 5% of the-volume of the protein preparation. When NBS-1 or PYRIN-1 protein is produced by chemical synthesis, it is preferably substantially free of chemical precursors or other chemicals, i.e., it is separated from chemical precursors or other chemicals which are involved in the synthesis of the protein. Accordingly such preparations of NBS-1 or PYRIN-1 protein have less than about 30%, 20%, 10%, 5% (by dry weight) of chemical precursors or non- NBS-1 or PYRIN-1 chemicals.

Biologically active portions of a NBS-1 or PYRIN-1 protein include peptides comprising amino acid sequences sufficiently identical to or derived from the amino acid sequence of the NBS-1 or PYRIN-1 protein (e.g., the amino acid sequence shown in SEQ ID NO:2 or SEQ ID NO:5), which include less amino acids than the full length NBS-1 or PYRIN-1 protein, and exhibit at least one activity of a NBS-1 or PYRIN-1 protein. Typically, biologically active portions comprise a domain or motif with at least one activity of the NBS-1 or PYRIN-1 protein. A biologically active portion of a NBS-1 or PYRIN-1 protein can be a polypeptide which is, for example, 10, 25, 50, 72, 100, 125, 150, 175, 200, 225, 250, 272, 300, 325, 350, 375, 400, 425, 450 or more amino acids in length. Preferred biologically active polypeptides include one or more identified NBS-1 or PYRIN-1 structural domains, e.g., the pyrin domain.

Moreover, other biologically active portions, in which other regions of the protein are deleted, can be prepared by recombinant techniques and evaluated for one or more of the functional activities of a native NBS-1 or PYRIN-1 protein.

Human NBS-1 and human PYRIN-1 proteins have the amino acid sequences of SEQ ID NO:2 or SEQ ID NO:5. Other useful NBS-1 or PYRIN-1 proteins are substantially identical to SEQ ID NO:2 or SEQ ID NO:5 and retain the functional activity of the protein of SEQ ID NO:2 or SEQ ID NO:5, yet differ in amino acid sequence due to natural allelic variation or mutagenesis.

A useful NBS-1 or PYRIN-1 protein is a protein which includes an amino acid sequence at least about 45%, preferably 55%, 65%, 75%, 85%, 95%, or 99% identical to the amino acid sequence of SEQ ID NO:2 or SEQ ID NO:5, and retains the functional activity of the NBS-1 or PYRIN-1 protein of SEQ ID NO:2 or SEQ ID NO:5.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions× 100).

The determination of percent homology between two sequences can be accomplished using a mathematical algorithm. A preferred, non-limiting example of a mathematical algorithm utilized for the comparison of two sequences is the algorithm of Karlin and Altschul (1990) Proc. Nat'l Acad. Sci. USA 87:2264-2268, modified as in Karlin and Altschul (1993) Proc. Nat'l Acad. Sci. USA 90:5873-5877. Such an algorithm is incorporated into the NBLAST and XBLAST programs of Altschul, et al. (1990) J. Mol. Biol. 215:403-410. BLAST nucleotide searches can be performed with the NBLAST program, score=100, wordlength=12 to obtain nucleotide sequences similar or homologous to NBS-1 or PYRIN-1 nucleic acid molecules of the invention. To obtain gapped alignments for comparison purposes, Gapped BLAST can be utilized as described in Altschul et al. (1997) Nucleic Acids Res. 25:3389-3402. When utilizing BLAST and Gapped BLAST programs, the default parameters of the respective programs (e.g., XBLAST and NBLAST) can be used (accessible at the website maintained by National Center for Biotechnology Information, Bethesda, Md., USA). Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. When utilizing the ALIGN program for comparing nucleic acid sequences, a gap length penalty of 12, and a gap penalty of 4 can be used. Another preferred example of a mathematical algorithm utilized for the comparison of sequences is the Needleman and Wunsch (J. Mol. Biol. (48):444-453 (1970)) algorithm which has been incorporated into the GAP program in the GCG software package (available at the bioinformatics page of the website maintained by Accelrys, Inc., San Diego, Calif., USA), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6.

The percent identity between two sequences can be determined using techniques similar to those described above, with or without allowing gaps. In calculating percent identity, typically exact matches are counted.

The invention also provides NBS-1 or PYRIN-1 chimeric or fusion proteins. As used herein, a NBS-1 or PYRIN-1 "chimeric protein" or "fusion protein" comprises a NBS-1 or PYRIN-1 polypeptide operatively linked to a non- NBS-1 or PYRIN-1 polypeptide. A "NBS-1 or-PYRIN-1 polypeptide" refers to a polypeptide having an amino acid sequence corresponding to all or a portion (preferably a biologically active portion) of a NBS-1 or PYRIN-1, whereas a "non-NBS-1 or PYRIN-1 polypeptide" refers to a polypeptide having an amino acid sequence corresponding to a protein which is not substantially identical to the NBS-1 or PYRIN-1 protein, e.g., a protein which is different from the NBS-1 or PYRIN-1 proteins and which is derived from the same or a different organism. Within the fusion protein, the term "operatively linked" is intended to indicate that the NBS-1 or PYRIN-1 polypeptide and the non-NBS-1 or PYRIN-1 polypeptide are fused in-frame to each other. The heterologous polypeptide can be fused to the N-terminus or C-terminus of the NBS-1 or PYRIN-1 polypeptide.

One useful fusion protein is a GST fusion protein in which the NBS-1 or PYRIN-1 sequences are fused to the C-terminus of the GST sequences. Such fusion proteins can facilitate the purification of recombinant NBS-1 or PYRIN-1. In another embodiment, the fusion protein contains a signal sequence from another protein. In certain host cells (e.g., mammalian host cells), expression and/or secretion of NBS-1 or PYRIN-1 can be increased through use of a heterologous signal sequence. For example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Molecular cloning, Sambrook et al, second edition, Cold spring harbor laboratory press, 1989) and the protein A secretory signal (Pharmacia Biotech; Piscataway, N.J.).

In yet another embodiment, the fusion protein is a NBS-1 or PYRIN-1-immunoglobulin fusion protein in which all or part of NBS-1 or PYRIN-1 is fused to sequences derived from a member of the immunoglobulin protein family. The NBS-1 or PYRIN-1-immunoglobulin fusion proteins of the invention can be incorporated into pharmaceutical compositions and administered to a subject to inhibit an interaction between a NBS-1 or PYRIN-1 ligand and a NBS-1 or PYRIN-1 protein on the surface of a cell, to thereby suppress NBS-1 or PYRIN-1-mediated signal transduction in vivo. The NBS-1 or PYRIN-1-immunoglobulin fusion proteins can be used to affect the bioavailability of a NBS-1 or PYRIN-1 cognate ligand. Inhibition of the NBS-1 or PYRIN-1 ligand/NBS-1 or PYRIN-1 interaction may be useful therapeutically for both the treatment of proliferative and differentiative disorders, as well as modulating (e.g., promoting or inhibiting) cell survival. Moreover, the NBS-1 or PYRIN-1-immunoglobulin fusion protein of the invention can be used as immunogens to produce anti-NBS-1 or PYRIN-1 antibodies in a subject, to purify NBS-1 or PYRIN-1 ligands and in screening assays to identify molecules which inhibit the interaction of NBS-1 or PYRIN-1 with a NBS-1 or PYRIN-1 ligand.

Preferably, a NBS-1 or PYRIN-1 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger ended termini for ligation, restriction enzyme digestion to provide for appropriate termini, filling in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Current Protocols in Molecular Biology, Ausubel et al. eds., John Wiley & Sons: 1992). Moreover, many expression vectors are commercially available that already encode a fusion moiety (e.g., a GST polypeptide). A NBS-1 or PYRIN-1-encoding nucleic acid can be cloned into such an expression vector such that the fusion moiety is linked in-frame to the NBS-1 or PYRIN-1 protein.

The present invention also pertains to variants of the NBS-1 or PYRIN-1 proteins which function as either NBS-1 or PYRIN-1 agonists (mimetics) or as NBS-1 or PYRIN-1 antagonists. Variants of the NBS-1 or PYRIN-1 proteins can be generated by mutagenesis, e.g., discrete point mutation or truncation of the NBS-1 or PYRIN-1 proteins. An agonist of the NBS-1 or PYRIN-1 protein can retain substantially the same, or a subset, of the biological activities of the naturally occurring form of the NBS-1 or PYRIN-1 protein. An antagonist of the NBS-1 or PYRIN-1 protein can inhibit one or more of the activities of the naturally occurring form of the NBS-1 or PYRIN-1 protein by, for example, competitively binding to a downstream or upstream member of a cellular signaling cascade which includes the NBS-1 or PYRIN-1 protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the NBS-1 or PYRIN-1 proteins.

Variants of the NBS-1 or PYRIN-1 protein which function as either NBS-1 or PYRIN-1 agonists (mimetics) or as NBS-1 or PYRIN-1 antagonists can be identified by screening combinatorial libraries of mutants, e.g., truncation mutants of the NBS-1 or PYRIN-1 protein for NBS-1 or PYRIN-1 protein agonist or antagonist activity. In one embodiment, a variegated library of NBS-1 or PYRIN-1 variants is generated by combinatorial mutagenesis at the nucleic acid level and is encoded by a variegated gene library. A variegated library of NBS-1 or PYRIN-1 variants can be produced by, for example, enzymatically ligating a mixture of synthetic oligonucleotides into gene sequences such that a degenerate set of potential NBS-1 or PYRIN-1 sequences is expressible as individual polypeptides, or alternatively, as a set of larger fusion proteins (e.g., for phage display) containing the set of NBS-1 or PYRIN-1 sequences therein. There are a variety of methods which can be used to produce libraries of potential NBS-1 or PYRIN-1 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential NBS-1 or PYRIN-1 sequences. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

Useful fragments of NBS-1 or PYRIN-1, include fragments comprising or consisting of a domain or subdomain described herein, e.g., LRR or NBS or pyrin domain.

In addition, libraries of fragments of the NBS-1 or PYRIN-1 protein coding sequence can be used to generate a variegated population of NBS-1 or PYRIN-1 fragments for screening and subsequent selection of variants of a NBS-1 or PYRIN-1 protein. In one embodiment, a library of coding sequence fragments can be generated by treating a double stranded PCR fragment of a NBS-1 or PYRIN-1 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the NBS-1 or PYRIN-1 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatrial mutagenesis of NBS-1 or PYRIN-1 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify NBS-1 or PYRIN-1 variants (Arkin and Yourvan (1992) Proc. Natl. Acad. Sci. USA 89:7811-7815; Delgrave et al. (1993) Protein Engineering 6(3):327-331).

An isolated NBS-1 or PYRIN-1 protein, or a portion or fragment thereof, can be used as an immunogen to generate antibodies that bind NBS-1 or PYRIN-1 using standard techniques for polyclonal and monoclonal antibody preparation. The full-length NBS-1 or PYRIN-1 protein can be used or, alternatively, the invention provides antigenic peptide fragments of NBS-1 or PYRIN-1 for use as immunogens. The antigenic peptide of NBS-1 or PYRIN-1 comprises at least 8 (preferably 10, 15, 20, or 30) amino acid residues of the amino acid sequence shown in SEQ ID NO:2 or SEQ ID NO:5 and encompasses an epitope of NBS-1 or PYRIN-1 such that an antibody raised against the peptide forms a specific immune complex with NBS-1 or PYRIN-1.

Useful antibodies include antibodies which bind to a domain or subdomain of NBS-1 or PYRIN-1 described herein (e.g., a LRR or NBS or pyrin domain).

Preferred epitopes encompassed by the antigenic peptide are regions of NBS-1 or PYRIN-1 that are located on the surface of the protein, e.g., hydrophilic regions. Other important criteria include a preference for a terminal sequence, high antigenic index (e.g., as predicted by Jameson-Wolf algorithm), ease of peptide synthesis (e.g., avoidance of prolines); and high surface probability (e.g., as predicted by the Emini algorithm; FIGS. 3 and 6).

A NBS-1 or PYRIN-1 immunogen typically is used to prepare antibodies by immunizing a suitable subject, (e.g., rabbit, goat, mouse or other mammal) with the immunogen. An appropriate immunogenic preparation can contain, for example, recombinantly expressed NBS-1 or PYRIN-1 protein or a chemically synthesized NBS-1 or PYRIN-1 polypeptide. The preparation can further include an adjuvant, such as Freund's complete or incomplete adjuvant, or similar immunostimulatory agent. Immunization of a suitable subject with an immunogenic NBS-1 or PYRIN-1 preparation induces a polyclonal anti-NBS-1 or PYRIN-1 antibody response.

Accordingly, another aspect of the invention pertains to anti-NBS-1 or PYRIN-1 antibodies. The term "antibody" as used herein refers to immunoglobulin molecules and immunologically active portions of immunoglobulin molecules, i.e., molecules that contain an antigen binding site which specifically binds an antigen, such as NBS-1 or PYRIN-1. A molecule which specifically binds to NBS-1 or PYRIN-1 is a molecule which binds NBS-1 or PYRIN-1, but does not substantially bind other molecules in a sample, e.g., a biological sample, which naturally contains NBS-1 or PYRIN-1. Examples of immunologically active portions of immunoglobulin molecules include F(ab) and F(ab')2 fragments which can be generated by treating the antibody with an enzyme such as pepsin. The invention provides polyclonal and monoclonal antibodies that bind NBS-1 or PYRIN-1. The term "monoclonal antibody" or "monoclonal antibody composition", as used herein, refers to a population of antibody molecules that contain only one species of an antigen binding site capable of immunoreacting with a particular epitope of NBS-1 or PYRIN-1. A monoclonal antibody composition thus typically displays a single binding affinity for a particular NBS-1 or PYRIN-1 protein with which it immunoreacts.

Polyclonal anti-NBS-1 or PYRIN-1 antibodies can be prepared as described above by immunizing a suitable subject with a NBS-1 or PYRIN-1 immunogen. The anti-NBS-1 or PYRIN-1 antibody titer in the immunized subject can be monitored over time by standard techniques, such as with an enzyme linked immunosorbent assay (ELISA) using immobilized NBS-1 or PYRIN-1. If desired, the antibody molecules directed against NBS-1 or PYRIN-1 can be isolated from the mammal (e.g., from the blood) and further purified by well-known techniques, such as protein A chromatography to obtain the IgG fraction. At an appropriate time after immunization, e.g., when the anti-NBS-1 or PYRIN-1 antibody titers are highest, antibody-producing cells can be obtained from the subject and used to prepare monoclonal antibodies by standard techniques, such as the hybridoma technique originally described by Kohler and Milstein (1975) Nature 256:495-497, the human B cell hybridoma technique (Kozbor et al. (1983) Immunol Today 4:72), the EBV-hybridoma technique (Cole et al. (1985), Monoclonal Antibodies and Cancer Therapy, Alan R. Liss, Inc., pp. 77-96) or trioma techniques. The technology for producing various antibodies monoclonal antibody hybridomas is well known (see generally Current Protocols in Immunology (1994) Coligan et al. (eds.) John Wiley & Sons, Inc., New York, N.Y.). Briefly, an immortal cell line (typically a myelorma) is fused to lymphocytes (typically splenocytes) from a mammal immunized with a NBS-1 or PYRIN-1 immunogen as described above, and the culture supernatants of the resulting hybridoma cells are screened to identify a hybridoma producing a monoclonal antibody that binds NBS-1or PYRIN-1.

Any of the many well known protocols used for fusing lymphocytes and immortalized cell lines can be applied for the purpose of generating an anti-NBS-1 or PYRIN-1 monoclonal antibody (see, e.g., Current Protocols in Immunology, supra; Galfre et al. (1977) Nature 266:55052; R. H. Kenneth, in Monoclonal Antibodies: A New Dimension In Biological Analyses, Plenum Publishing Corp., New York, N.Y. (1980); and Lemer (1981) Yale J. Biol. Med., 54:387-402). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC (Manassas, Va.). Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supematants for antibodies that bind NBS-1 or PYRIN-1, e.g., using a standard ELISA assay.

Alternative to preparing monoclonal antibody-secreting hybridomas, a monoclonal anti-NBS-1 or PYRIN-1 antibody can be identified and isolated by screening a recombinant combinatorial immunoglobulin library (e.g., an antibody phage display library) with NBS-1 or PYRIN-1 to thereby isolate immunoglobulin library members that bind NBS-1 or PYRIN-1. Kits for generating and screening phage display libraries are commercially available (e.g., the Pharmacia Recombinant Phage Antibody System, Catalog No. 27-9400-01; and the Stratagene SurfZAP Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology 9:1370-1372; Hay et al., (1992) Hum. Antibod. Hybridomas 3:81-85; Huse et al. (1989) Science 246:1275-1281; Griffiths et al. (1993) EMBO J. 12:725-734.

Additionally, recombinant anti-NBS-1 or PYRIN-1 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Canc. Res. 47:999-1005; Wood et al. (1985) Nature 314:446-449; and Shaw et al. (1988) J. Natl. Cancer Inst. 80:1553-1559); Morrison, (1985) Science 229:1202-1207; Oi et al. (1986) Bio/Techniques 4:214; U.S. Pat. No. 5,225,539; Jones et al. (1986) Nature 321:552-525; Verhoeyan et al. (1988) Science 239:1534; and Beidler et al. (1988) J. Immunol. 141:4053-4060.

An anti-NBS-1 or PYRIN-1 antibody (e.g., monoclonal antibody) can be used to isolate NBS-1 or PYRIN-1 by standard techniques, such as affinity chromatography or immunoprecipitation. An anti-NBS-1 or PYRIN-1 antibody can facilitate the purification of natural NBS-1 or PYRIN-1 from cells and of recombinantly produced NBS-1 or PYRIN-1 expressed in host cells. Moreover, an anti-NBS-1 or PYRIN-1 antibody can be used to detect NBS-1 or PYRIN-1 protein (e.g., in a cellular lysate or cell supernatant) in order to evaluate the abundance and pattern of expression of the NBS-1 or PYRIN-1 protein. Anti-NBS-1 or PYRIN-1 antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator; or, biological response modifiers such as, for example, lymphokines, interleukin-1 (IL-1), interleukin-2 (IL-2), interleukin-6 (IL-6), granulocyte macrophase colony stimulating factor (GM-CSF), granulocyte colony stimulating factor (G-CSF), or other growth factors.

Techniques for conjugating such therapeutic moiety to antibodies are well known, see, e.g., Arnon et al., "Monoclonal Antibodies for Immunotargeting of Drugs in Cancer Therapy", in Monoclonal Antibodies and Cancer Therapy, Reisfeld et al. (eds.), pp. 243-56 (Alan R. Liss, Inc. 1985); Hellstrom et al., "Antibodies for Drug Delivery", in Controlled Drug Delivery (2nd Ed.), Robinson et al. (eds.), pp. 623-53 (Marcel Dekker, Inc. 1987); Thorpe, "Antibody Carriers of Cytotoxic Agents in Cancer Therapy: A Review", in Monoclonal Antibodies '84: Biological and Clinical Applications, Pinchera et al. (eds.), pp. 475-506 (1985); "Analysis, Results, and Future Prospective of The Therapeutic Use of Radiolabeled Antibody In Cancer Therapy", in Monoclonal Antibodies for Cancer Detection and Therapy, Baldwin et al. (eds.), pp. 303-16 (Academic Press 1985), and Thorpe et al., "The Preparation and Cytotoxic Properties of Antibody-Toxin Conjugates", Immunol. Rev., 62:119-58 (1982). Alternatively, an antibody can be conjugated to a second antibody to form an antibody heteroconjugate as described by Segal in U.S. Pat. No. 4,676,980.

In addition, antibodies of the invention, either conjugated or not conjugated to a therapeutic moiety, can be administered together or in combination with a therapeutic moiety such as a cytotoxin, a therapeutic agent or a radioactive metal ion. The order of administration of the antibody and therapeutic moiety can vary. For example, in some embodiments, the antibody is administered concurrently (through the same or different delivery devices, e.g., syringes) with the therapeutic moiety. Alternatively, the antibody can be administered separately and prior to the therapeutic moiety. Still alternatively, the therapeutic moiety is administered separately and prior to the antibody. In many embodiments, these administration regimens will be continued for days, months or years.

Another aspect of the invention relates to a method for inducing an immunological response in a mammal which comprises inoculating the mammal with a NBS-1 or PYRIN-1 polypeptide, adequate to produce antibody and/or T cell immune response to protect the animal from the diseases hereinbefore mentioned, amongst others. Yet another aspect of the invention relates to a method of inducing immunological response in a mammal which comprises, delivering a NBS-1 or PYRIN-1 polypeptide via a vector directing expression of the polynucleotide and coding for the polypeptide in vivo in order to induce such an immunological response to produce antibody to protect the animal from diseases.

A further aspect of the invention relates to an immunological/vaccine formulation (composition) which, when introduced into a mammalian host, induces an immunological response in that mammal to a NBS-1 or PYRIN-1 polypeptide of the present invention wherein the composition comprises a polypeptide or polynucleotide of NBS-1 or PYRIN-1. The vaccine formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

III. Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exist in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. This skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a work processing test file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or a target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration formed upon the folding of the target motif. There are a variety of target motifs know in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of know algorithms are disclosed publicly and a variety of commercially-available software for conducting search means are and can be used in the computer-based systems of the present invention. Examples of such software include, but is not limited to, MacPattern (EMBL), BLASTIN and BLASTX (NCBIA).

For example, software that implements the BLAST (Altschul et al. (1990) J. of Mol. Biol. 215:403-410) and BLAZE (Brutlag et al. (1993) Comp. Chem. 17:203-207) search algorithms on a Sybase system can be used to identify open reading frames (ORFs) of the sequences of the invention which contain homology to ORFs or proteins from other libraries. Such ORFs are protein-encoding fragments and are useful in producing commercially important proteins such as enzymes used in various reactions and in the production of commercially useful metabolites.

IV. Recombinant Expression Vectors and Host Cells

Another aspect of the invention pertains to vectors, preferably expression vectors, containing a nucleic acid encoding NBS-1 or PYRIN-1 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operatively linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals); Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., NBS-1 or PYRIN-1 proteins, mutant forms of NBS-1 or PYRIN-1, fusion proteins, etc.).

The recombinant expression vectors of the invention can be designed for expression of NBS-1 or PYRIN-1 in prokaryotic or eukaryotic cells, e.g., bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion E. coli expression vectors include pTrc (Amann et al., (1988) Gene 69:301-315) and pET 11d (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident ë prophage harboring a T7 gn1 gene under the transcriptional control of the lacUV5 promoter.

One strategy to maximize recombinant protein expression in E. coli is to express the protein in a bacterial having an impaired capacity to proteolytically cleave the recombinant protein (Gottesman, Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those preferentially utilized in E. coli (Wada et al. (1992) Nucleic Acids Res. 20:2111-2118). Such alteration of nucleic acid sequences of the invention can be carried out by standard DNA synthesis techniques.

In another embodiment, the NBS-1 or PYRIN-1 expression vector is a yeast expression vector. Examples of vectors for expression in yeast S. cerivisae include pYepSec1 (Baldari et al. (1987) EMBO J. 6:229-234), pMFa (Kurjan and Herskowitz, (1982) Cell 30:933-943), pJRY88 (Schultz et al. (1987) Gene 54:113-123), pYES2 (Invitrogen Corporation, San Diego, Calif.), pGBT9 (Clontech, Palo Alto, Calif.), pGAD10 (Clontech, Palo Alto, Calif.), pYADE4 and pYGAE2 and pYPGE2 (Brunelli and Pall, (1993) Yeast 9:1299-1308), pYPGE15 (Brunelli and Pall, (1993) Yeast 9:1309-1318), pACTII (Dr. S. E. Elledge, Baylor College of Medicine), and picZ (InVitrogen Corp, San Diego, Calif.). Alternatively, NBS-1 or PYRIN-1 can be expressed in insect cells using baculovirus expression vectors. Baculovirus vectors available for expression of proteins in cultured insect cells (e.g., Sf9 cells) include the pAc series (Smith et al.

(1983) Mol. Cell Biol. 3:2156-2165) and the pVL series (Lucklow and Summers (1989) Virology 170:31-39).

In yet another embodiment, a nucleic acid of the invention is expressed in mammalian cells using a mammalian expression vector. Examples of mammalian expression vectors include pCDM8 (Seed (1987) Nature 329:840), pCI (Promega), and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al. (supra).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166).

Developmentally-regulated promoters are also encompassed, for example the murine hox promoters (Kessel and Gruss (1990) Science 249:374-379) and the α-fetoprotein promoter (Campes and TilghInan (1989) Genes Dev. 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule-which is antisense to NBS-1 or PYRIN-1 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews-Trends in Genetics, Vol. 1(1) 1986).

Another aspect of the invention pertains to host cells into which a recombinant expression vector of the invention or isolated nucleic acid molecule of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, NBS-1 or PYRIN-1 protein can be expressed in bacterial cells such as E. coli, insect cells, yeast or mammalian cells (such as Chinese hamster ovary cells (CHO) or COS cells). Other suitable host cells are known to those skilled in the art.

Vector DNA or an isolated nucleic acid molecule of the invention can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In some cases vector DNA is retained by the host cell. In other cases the host cell does not retain vector DNA and retains only an isolated nucleic acid molecule of the invention carried by the vector. In some cases, and isolated nucleic acid molecule of the invention is used to transform a cell without the use of a vector.

In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding NBS-1 or PYRIN-1 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a NBS-1 or PYRIN-1 protein. Accordingly, the invention further provides methods for producing NBS-1 or PYRIN-1 protein using the host cells of the invention. In one embodiment, the method comprises culturing the host cell of the invention (into which a recombinant expression vector or isolated nucleic acid molecule encoding NBS-1 or PYRIN-1 has been introduced) in a suitable medium such that NBS-1 or-PYRIN-1 protein is produced. In another embodiment, the method further comprises isolating NBS-1 or PYRIN-1 from the medium or the host cell.

NBS-1 and PYRIN-1 nucleic acid molecules can be used in viral gene delivery systems for gene therapy, e.g., adenoviral or retroviral gene delivery systems.

NBS-1 and PYRIN-1 nucleic acid molecules can also be used in non-viral gene delivery systems for gene therapy. Thus, another aspect of the invention pertains to non-viral gene delivery systems, such as plasmid-based gene delivery systems. Non-viral gene delivery systems are described in detail by Huang et al. ((1999) Nonviral Vectors for Gene Therapy, Academic Press, San Diego, Calif.). Nonviral vectors have several potential advantages over their viral counterparts, including: reduced immunogenicity; low acute toxicity; simplicity; and ease of large scale production. Nonviral vectors can be delivered as naked DNA, by bioballistic bombardment, and in various complexes, including liposome/DNA complexes (lipoplexes), polymer/DNA complexes (polyplexes), and liposome/polymer/DNA complexes (lipopolyplexes). Nonviral vectors may be administered by various routes, e.g., intravenous injection, peritoneal injection, intramuscular injection, subcutaneous injection, intratracheal injection, and aerosolization.

Naked DNA (i.e. free from association with, e.g., transfection-facilitating proteins, viral particles, liposomal formulations, charged lipids and calcium phosphate precipitating), can be expressed at its injection site or at a remote site. For example, naked DNA can be injected directly into skeletal muscle, liver, heart muscle, and tumor tissue. For systemic administration, plasmid DNA may need to be protected from degradation by endonucleases during delivery from the site of administration to the site of gene expression.

Bioballistic bombardment, also known as gene gun, allows for the penetration of target cells in vitro, ex vivo, or in vivo. In this technique, DNA-coated gold particles are accelerated to a high velocity by an electric arc generated by a high voltage discharge. The method is effective for a variety of organ types, including skin, liver, muscle, spleen, and pancreas. The gene gun transfer method is not dependent upon specific cell surface receptors, cell cycle status, or the size of the DNA vector. Useful gene gun devices include the Accell® (PowderJect Vaccines, Inc.) and the Helios™ (Bio-Rad). These devices create a compressed shock wave of helium gas, accelerating DNA-coated gold (or tungsten) particles to high speed, whereby the particles have sufficient momentum to penetrate a target tissue.

Lipoplexes are typically made up of three components: a cationic lipid, a neutral colipid, and plasmid DNA that encodes one or more genes of interest. Commonly used cationic lipids include DOTMA, DMRIE, DC-chol, DOTAP, DMRIE, DDAB, DODAB/C, DOGS, DOSPA, SAINT-n, DOSPER, DPPES, DORIE, GAP-DLRIE, and DOTIM. Dioleoyl (DO) and dimyristoyl (DM) chains are thought to be especially effective for gene delivery. Cationic lipids are typically composed of a positively charged headgroup, a hydrophobic lipid anchor, and a linker that connects the headgroup and anchor. Catioinc lipids used in lipoplexes can be divided into two broad classes: those that use cholesterol as the lipid anchor and those that use diacyl chains of varying lengths and extent of saturation. The number of protonatable amines on the headgroup may affect transfection activity, with multivalent headgroups being generally more active than monovalent headgroups. The linker can be made of a variety of chemical structures, e.g., ether, amide, carbamate, amine, urea, ester, and peptide bonds. Neutral colipids of lipoplexes commonly include DOPE, DOPC, and cholesterol. Generally, DOPE is used as the neutral colipid with catioinc lipids that are based on cholesterol (e.g., DC-chol, GL-67) and cholesterol is used as the neutral colipid with cationic lipids that harbor diacyl chains as the hydrophobic anchor (e.g., DOTAP, DOTIM).

Polyplexes are formed when cationic polymers are mixed with DNA. Cationic polymers used to from polyplexes are of two general types: linear polymers such as polylysine and spermine; and the branched chain, spherical, or globular polycations such as polyetheleneimine and dendrimers. Lipopolyplexes are formed by the incorporation of polylysine into a lipoplex to form ternary complexes. DNA can be complexed with a natural biopolymer, e.g., gelatin or chitosan, functioning as a gene carrier to form nanospheres. Such biodegradable nanospheres have several advantages, including the coencapsulation of bioactive agents, e.g. nucleic acids and drugs, and the sustained release of the DNA. Gelatin-DNA or chitosan-DNA nanospheres are synthesized by mixing the DNA solution with an aqueous solution of gelatin or chitosan.

The effectiveness nonviral vectors may be enhanced by conjugation to ligands that direct the vector either to a particular cell type or to a particular location within a cell. Antibodies and other site-specific proteins can be attached to a vector, e.g., on the surface of the vector or incorporated in the membrane. Following injection, these vectors bind efficiently and specifically to a target site. With respect to liposomes, ligands to a cell surface receptor can be incorporated into the surface of a liposome by covalently modifying the ligand with a lipid group and adding it during the formation of liposomes. The following classes of ligands can be incorporated into the nonviral DNA delivery complexes of the invention in order to make them more effective for gene delivery: (1) peptides, e.g., peptides having a specific cell surface receptor so that complexes will be targeted to specific cells bearing the receptor; (2) nuclear localization signals, e.g., to promote efficient entry of DNA into the nucleus; (3) pH-sensitive ligands, to encourage endosomal escape; (4) steric stabilizing agents, to prevent destabilization of the complexes after introduction into the biological milieu. Gene chemistry approaches, e.g. peptide nucleic acids, can be used to couple ligands to DNA to improve the in vivo bioavailability and expression of the DNA.

In plasmid-based, non-viral gene delivery systems it is often useful to link a polypeptide (e.g., an antibody), nucleic acid molecule, or other compound to the gene delivery plasmid such that the polypeptide, nucleic acid molecule or other compound remains associated with the plasmid following intracellular delivery in a manner that does not interfere with the transcriptional activity of the plasmid. This can be accomplished using an appropriate biotin-conjugated peptide nucleic acid (PNA) clamp. A sequence complementary to the biotin-conjugated PNA clamp is inserted into the gene delivery plasmid. The biotin-conjugated PNA will bind essentially irreversibly to the complementary sequence inserted into the plasmid. A polypeptide, nucleic acid molecule or other compound of interest can be conjugated to streptavidin. The streptavidin conjugate can bind to the biotin-PNA clamp bound to the plasmid. In this manner, a polypeptide, nucleic acid molecule or other compound can be bound to a gene delivery plasmid such that the polypeptide, nucleic acid molecule or other compound remains bound to the plasmid even within a cell. Importantly, the PNA clamp-binding site in the plasmid must be chosen so as not to interfere with a needed promoter/enhancer or coding region or otherwise disrupt the expression of the gene in the plasmid. An alternative approach employs a maleimide-conjugated PNA clamp. Polypeptides, nucleic acid molecules and other compounds containing a free thiol residue may be conjugated directly to the maleimide-PNA-DNA hybrid. As with the biotin-conjugated method, this conjugation does not disturb the transcriptional activity of the plasmid if the PNA-binding site is chosen to be in a region of the plasmid not essential for gene activity. Both of these approaches are described in detail by Zelphati et al. ((2000) BioTechniques 28:304-315).

The host cells of the invention can also be used to produce nonhuman transgenic animals. For example, in one embodiment, a host cell of the invention is a fertilized oocyte or an embryonic stem cell into which NBS-1 or PYRIN-1-coding sequences have been introduced. Such host cells can then be used to create non-human transgenic animals in which exogenous NBS-1 or PYRIN-1 sequences have been introduced into their genome or homologous recombinant animals in which endogenous NBS-1 or PYRIN-1 sequences have been altered. Such animals are useful for studying the function and/or activity of NBS-1 or PYRIN-1 and for identifying and/or evaluating modulators of NBS-1 or PYRIN-1 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous NBS-1 or PYRIN-1 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing NBS-1 or PYRIN-1-encoding nucleic acid into the male pronuclei of a fertilized oocyte, e.g., by microinjection, retroviral infection, and allowing the oocyte to develop in a pseudopregnant female foster animal. The NBS-1 or PYRIN-1 cDNA sequence, e.g., that of SEQ ID NO:1, SEQ ID NO:3, SEQ ID NO:4, SEQ ID NO:6 can be introduced as a transgene into the genome of a non-human animal. Alternatively, a nonhuman homolog or ortholog of the human NBS-1 or PYRIN-1 gene, such as a mouse NBS-1 or PYRIN-1 gene, can be isolated based on hybridization to the human NBS-1 or PYRIN-1 cDNA and used as a transgene. Intronic sequences and polyadenylation signals can also be included in the transgene to increase the efficiency of expression of the transgene. A tissue-specific regulatory sequence(s) can be operably linked to the NBS-1 or PYRIN-1 transgene to direct expression of NBS-1 or PYRIN-1 protein to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the NBS-1 or PYRIN-1 transgene in its genome and/or expression of NBS-1 or PYRIN-1 mRNA in tissues or cells of the animals. A transgenic founder animal can then be used to breed additional animals carrying the transgene. Moreover, transgenic animals carrying a transgene encoding NBS-1 or PYRIN-1 can further be bred to other transgenic animals carrying other transgenes.

To create an homologous recombinant animal, a vector is prepared which contains at least a portion of a NBS-1 or PYRIN-1 gene (e.g., a human or a non-human homolog of the NBS-1 or PYRIN-1 gene, e.g., a murine NBS-1 or PYRIN-1 gene) into which a deletion, addition or substitution has been introduced to thereby alter, e.g., functionally disrupt, the NBS-1 or PYRIN-1 gene. In an embodiment, the vector is designed such that, upon homologous recombination, the endogenous NBS-1 or PYRIN-1 gene is functionally disrupted (i.e., no longer encodes a functional protein; also referred to as a "knock out" vector). Alternatively, the vector can be designed such that, upon homologous recombination, the endogenous NBS-1 or PYRIN-1 gene is mutated or otherwise altered but still encodes functional protein (e.g., the upstream regulatory region can be altered to thereby alter the expression of the endogenous NBS-1 or PYRIN-1 protein). In the homologous recombination vector, the altered portion of the NBS-1 or PYRIN-1 gene is flanked at its 5' and 3' ends by additional nucleic acid of the NBS-1 or PYRIN-1 gene to allow for homologous recombination to occur between the exogenous NBS-1 or PYRIN-1 gene carried by the vector and an endogenous NBS-1 or PYRIN-1 gene in an embryonic stem cell. The additional flanking NBS-1 or PYRIN-1 nucleic acid is of sufficient length for successful homologous recombination with the endogenous gene. Typically, several kilobases of flanking DNA (both at the 5' and 3' ends) are included in the vector (see, e.g., Thomas and Capecchi (1987) Cell 51:503 for a description of homologous recombination vectors). The vector is introduced into an embryonic stem cell line (e.g., by electroporation) and cells in which the introduced NBS-1 or PYRIN-1 gene has homologously recombined with the endogenous NBS-1 or PYRIN-1 gene are selected (see, e.g., Li et al. (1992) Cell 69:915). The selected cells are then injected into a blastocyst of an animal (e.g., a mouse) to form aggregation chimeras (see, e.g., Bradley in Teratocarcinomas and Embryonic Stem Cells: A Practical Approach, Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Current Opinion in Bio/Technology 2:823-829 and in PCT Publication Nos. WO 90/11354, WO 91/01140, WO 92/0968, and WO 93/04169.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232-6236. Another example of a recombinase system is the FLP recombinase system of *Saccharomyces cerevisiae* (O'Gorman et al. (1991) Science 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) Nature 385:810-813 and PCT Publication Nos. WO 97/07668 and WO 97/07669. In brief, a cell, e.g., a somatic cell, from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

In another embodiment, the expression characteristics of an endogenous NBS-1 or PYRIN-1 gene within a cell line or microorganism may be modified by inserting a heterologous DNA regulatory element into the genome of a stable cell line or cloned microorganism such that the inserted regulatory element is operatively linked with the endogenous NBS-1 or PYRIN-1 gene. For example, an endogenous NBS-1 or PYRIN-1 which is normally "transcriptionally silent," i.e. a NBS-1 or PYRIN-1 gene which is normally not expressed, or is-expressed only at very low levels in a cell line or microorganism, may be activated by inserting a regulatory element which is capable of promoting the expression of a normally expressed gene product in that cell line or microorganism. Alternatively, a transcriptionally silent, endogenous NBS-1 or PYRIN-1 gene may be activated by insertion of a promiscuous regulatory element that works across cell types.

A heterologous regulatory element may be inserted into a stable cell line or cloned microorganism, such that it is operatively linked with an endogenous NBS-1 or PYRIN-1 gene, using techniques, such as targeted homologous recombination, which are well known to those of skill in the art, and described e.g., in Chappel, U.S. Pat. No. 5,272,071; PCT publication No. WO 91/06667, published May 16, 1991.

V. Pharmaceutical Compositions

The NBS-1 or PYRIN-1 nucleic acid molecules, NBS-1 or PYRIN-1 proteins, and anti-NBS-1 or PYRIN-1 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of the invention. Such methods comprise formulating a pharmaceutically acceptable carrier with an agent which modulates expression or activity of a polypeptide or nucleic acid of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid of the invention and one or more additional active compounds.

The agent which modulates expression or activity may, for example, be a small molecule. For example, such small molecules include peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight les than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a NBS-1 or PYRIN-1 protein or anti-NBS-1 or PYRIN-1 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of protein, polypeptide, or antibody can include a single treatment or, preferably, can include a series of treatments.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and filly human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) J. Acquired Immune Deficiency Syndromes and Human Retrovirology 14:193).

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The gene therapy vectors of the invention can be either viral or non-viral. Examples of plasmid-based, non-viral vectors are discussed in Huang et al. (1999) Nonviral Vectors for Gene Therapy (supra). A modified plasmid is one example of a non-viral gene delivery system. Peptides, proteins (including antibodies), and oligonucleotides may be stably conjugated to plasmid DNA by methods that do not interfere with the transcriptional activity of the plasmid (Zelphati et al. (2000) BioTechniques 28:304-315). The attachment of proteins and/or oligonucleotides may influence the delivery and trafficking of the plasmid and thus render it a more effective pharmaceutical composition.

The pharmaceutical compositions can be included in a container, pack, or dispenser together with instructions for administration.

VI. Uses and Methods of the Invention

The nucleic acid molecules, proteins, protein homologues, and antibodies described herein can be used in one or more of the following methods: a) screening assays; b) detection assays (e.g., chromosomal mapping, tissue typing, forensic biology), c) predictive medicine (e.g., diagnostic assays, prognostic assays, monitoring clinical trials, and pharmacogenomics); and d) methods of treatment (e.g., therapeutic and prophylactic). A NBS-1 or PYRIN-1 protein interacts with other cellular proteins and can thus be used for (i) regulation of cellular proliferation; (ii) regulation of cellular differentiation; and (iii) regulation of cell survival. The isolated nucleic acid molecules of the invention can be used to express NBS-1 or PYRIN-1 protein (e.g., via a recombinant expression vector in a host cell in gene therapy applications), to detect NBS-1 or PYRIN-1 mRNA (e.g., in a biological sample) or a genetic lesion in a NBS-1 or PYRIN-1 gene, and to modulate NBS-1 or PYRIN-1 activity. In addition, the NBS-1 or PYRIN-1 proteins can be used to screen drugs or compounds which modulate the NBS-1 or PYRIN-1 activity or expression as well as to treat disorders characterized by insufficient or excessive production of NBS-1 or PYRIN-1 protein or production of NBS-1 or PYRIN-1 protein forms which have decreased or aberrant activity compared to NBS-1 or PYRIN-1 wild type protein. In addition, the anti-NBS-1 or PYRIN-1 antibodies of the invention can be used to detect-and-isolate NBS-1 or PYRIN-1 proteins and modulate NBS-1 or PYRIN-1 activity.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to NBS-1 or PYRIN-1 proteins or biologically active portions thereof or have a stimulatory or inhibitory effect on, for example, NBS-1 or PYRIN-1 expression or NBS-1 or PYRIN-1 activity. An example of a biologically active portion of human NBS-1 is a domain described herein. An example of a biologically active portion of human PYRIN-1 is a domain described herein.

Among the screening assays provided by the invention are screening to identify molecules that prevent the interaction of NBS-1 or PYRIN-1 with another protein and screening to identify a competitive inhibitor of the binding of a nucleotide to the nucleotide binding site of NBS-1 or PYRIN-1. Such assays can employ full-length NBS-1 or PYRIN-1 or a portion of NBS-1 or PYRIN-1, e.g., a domain define herein.

Screening assays can be used to identify molecules which modulate a NBS-1 or PYRIN-1 mediated increase in transcription of genes having an AP-1 or NF-κB binding site. For example, expression of a reporter gene under the control of NF-κB (or AP-1) is measured in the presence and absence of a candidate molecule and in the presence and absence of NBS-1 or PYRIN-1 to identify those molecules which alter expression of the reporter in a NBS-1 or PYRIN-1 dependent manner. In addition, screening assays can be used to identify molecules that modulate a NBS-1 or PYRIN-1 mediated increase in CHOP phosphorylation. For example, the expression of a reporter gene under the control of CHOP is measured in the presence and absence of a candidate small molecule and in the presence and absence of NBS-1 or PYRIN-1 to identify those molecules that alter expression of the reporter in a NBS-1 or PYRIN-1 dependent manner. A screening assay can be carried out to identify molecules which modulate the NBS-1 or PYRIN-1 mediated increase in CHOP phosphorylation. For example, CHOP phosphorylation is measured in the presence and absence of a candidate molecule and in the presence and absence of NBS-1 or PYRIN-1. Phosphorylation of CHOP can be measured using an antibody which binds to phosphorylated CHOP, but not to non-phosphorylated CHOP.

In one embodiment, the invention provides assays for screening candidate or test compounds which bind to or-modulate the activity of a NBS-1 or PYRIN-1 proteins or polypeptides or biologically active portions thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145). Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds may be presented in solution (e.g., Houghten (1992) Bio/Techniques 13:412-421), or on beads (Lam (1991) Nature 354:82-84), chips (Fodor (1993) Nature 364:555-556), bacteria (U.S. Pat. No. 5,223,409), spores (U.S. Pat. Nos. 5,571,698; 5,403,484; and 5,223, 409), plasmids (Cull et al. (1992) Proc. Natl. Acad. Sci. USA 89:1865-1869) or on phage (Scott and Smith (1990) Science 249:386-390; Devlin (1990) Science 249:404-406; Cwirla et al. (1990) Proc. Natl. Acad. Sci. 87:6378-6382; and Felici (1991) J. Mol. Biol. 222:301-310).

In one embodiment, an assay is one in which a polypeptide of the invention, or a biologically active portion thereof, is contacted with a test compound and the ability of the test compound to bind to the polypeptide determined. Determining the ability of the test compound to bind to the polypeptide can be accomplished, for example, by coupling the test compound with a radioisotope or enzymatic label such that binding of the test compound to the polypeptide or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

Determining the ability of the test compound to modulate the activity of NBS-1 or PYRIN-1 or a biologically active portion thereof can be accomplished, for example, by determining the ability of the NBS-1 or PYRIN-1 protein to bind to or interact with a NBS-1 or PYRIN-1 target molecule. As used herein, a "target molecule" is a molecule with which a NBS-1 or PYRIN-1 protein binds or interacts in nature, for example, a molecule associated with the internal surface of a cell membrane or a cytoplasmic molecule. A NBS-1 or PYRIN-1 target molecule can be a non-NBS-1 or PYRIN-1 molecule or a NBS-1 or PYRIN-1 protein or polypeptide of the present invention. In one embodiment, a NBS-1 or PYRIN-1 target molecule is a component of an apoptotic signal transduction pathway. The target, for example, can be a second intracellular protein which has catalytic activity or a protein which facilitates the association of downstream signaling molecules with NBS-1 or PYRIN-1. In particular the target can be another protein having a pyrin domain (or a pyrin domain containing fragment thereof).

Determining the ability of the test compound to modulate the activity of NBS-1 or PYRIN-1 or a biologically active portion thereof can be accomplished, for example, by determining the ability of the NBS-1 or PYRIN-1 protein to bind to or interact with any of the specific proteins listed in the previous paragraph as NBS-1 or PYRIN-1 target molecules. In another embodiment, NBS-1 or PYRIN-1 target molecules include all proteins that bind to a NBS-1 or PYRIN-1 protein or a fragment thereof in a two-hybrid system binding assay which can be used without undue experimentation to isolate such proteins from CDNA or genomic two-hybrid system libraries. The binding assays described in this section can be cell-based or cell free (described subsequently).

Determining the ability of the NBS-1 or PYRIN-1 protein to bind to or interact with a NBS-1 or PYRIN-1 target molecule can be accomplished by one of the methods described above for determining direct binding. In an embodiment, determining the ability of the NBS-1 or PYRIN-1 protein to bind to or interact with a NBS-1 or PYRIN-1 target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a NBS-1 or PYRIN-1-responsive regulatory element operatively linked to a nucleic acid encoding a detectable marker, e.g. luciferase), or detecting a cellular response, for example, cell survival, cellular differentiation, or cell proliferation. The activity of a target molecule can be monitored by assaying the caspase 9-mediated apoptosis cellular response or caspase 9 enzymatic activity. In addition, and in another embodiment, genes induced by NBS-1 or PYRIN-1 expression can be identified by expressing NBS-1 or PYRIN-1 in a cell line and conducting a transcriptional profiling experiment wherein the mRNA expression patterns of the cell line transformed with an empty expression vector and the cell line transformed with a NBS-1 or PYRIN-1 expression vector are compared. The promoters of genes induced by NBS-1 or PYRIN-1 expression can be operatively linked to reporter genes suitable for screening such as luciferase, secreted alkaline phosphatase, or beta-galactosidase and the resulting constructs could be introduced into appropriate expression vectors. A recombinant cell line containing NBS-1 or PYRIN-1 and transfected with an expression vector containing a NBS-1 or PYRIN-1 responsive promoter operatively linked to a reporter gene can be used to identify test compounds that modulate NBS-1 or PYRIN-1 activity by assaying the expression of the reporter gene in response to contacting the recombinant cell line with test compounds. NBS-1 or PYRIN-1 agonists can be identified as increasing the expression of the reporter gene and NBS-1 or PYRIN-1 antagonists can be identified as decreasing the expression of the reporter gene.

In another embodiment of the invention, the ability of a test compound to modulate the activity of NBS-1 or PYRIN-1, or biologically active portions thereof can be determined by assaying the ability of the test compound to modulate NBS-1 or PYRIN-1-dependent pathways or processes where the NBS-1 or PYRIN-1 target proteins that mediate the NBS-1 or PYRIN-1 effect are known or unknown. Potential NBS-1 or PYRIN-1-dependent pathways or processes include, but are not limited to, the modulation of cellular signal transduction pathways and their related second messenger molecules (e.g., intracellular Ca2+, diacylglycerol, IP3, cAMP etc.), cellular enzymatic activities, cellular responses (e.g., cell survival, cellular differentiation, or cell proliferation), or the induction or repression of cellular or heterologous mRNAs or proteins. NBS-1 or PYRIN-1 -dependent pathways or processes could be assayed by standard cell-based or cell free assays appropriate for the specific pathway or process under study. In another embodiment, cells cotransfected with NBS-1 or PYRIN-1 and a NF-κB luciferase reporter gene could be contacted with a test compound and test compounds that block NBS-1 or PYRIN-1 activity could be identified by their reduction of NBS-1 or PYRIN-1 -dependent NF-κB pathway luciferase reporter gene expression. Test compounds that agonize NBS-1 or PYRIN-1 would be expected to increase reporter gene expression. In another embodiment, NBS-1 or PYRIN-1 could be expressed in a cell line and the recombinant NBS-1 or PYRIN-1-expressing cell line could be contacted with a test compound. Test compounds that inhibit NBS-1 or PYRIN-1 activity could be identified by their reduction of NBS-1 or PYRIN-1 -depended NF-κB pathway stimulation as measured by the assay of a NF-κB pathway reporter gene, NF-κB nuclear localization, IκB phosphorylation or proteolysis, or other standard assays for NF-κB pathway activation known to those skilled in the art.

In yet another embodiment, an assay of the present invention is a cell-free assay comprising contacting a NBS-1 or PYRIN-1 protein or biologically active portion thereof with a test compound and determining the ability of the test compound to bind to the NBS-1 or PYRIN-1 protein or biologically active portion thereof. Binding of the test compound to the NBS-1 or PYRIN-1 protein can be determined either directly or indirectly as described above. In one embodiment, a competitive binding assay includes contacting the NBS-1 or PYRIN-1 protein or biologically active portion thereof with a compound known to bind NBS-1 or PYRIN-1 to form an assay mixture, contacting the assay mixture with a test compound, and determining the ability of the test compound to interact with a NBS-1 or PYRIN-1 protein, wherein determining the ability of the test compound to interact with a NBS-1 or PYRIN-1 protein comprises determining the ability of the test compound to preferentially bind to NBS-1 or PYRIN-1 or biologically active portion thereof as compared to the known binding compound.

In another embodiment, an assay is a cell-free assay comprising contacting NBS-1 or PYRIN-1 protein or biologically active portion thereof with a test compound and determining the ability of the test compound to modulate (e.g., stimulate or inhibit) the activity of the NBS-1 or PYRIN-1 protein or biologically active portion thereof. Determining the ability of the test compound to modulate the activity of NBS-1 or PYRIN-1 can be accomplished, for example, by determining the ability of the NBS-1 or PYRIN-1 protein to bind to or interact with a NBS-1 or PYRIN-1 target molecule by one of the methods described above for determining direct binding. In an alternative embodiment, determining the ability of the test compound to modulate the activity of NBS-1 or PYRIN-1 can be accomplished by determining the ability of the NBS-1 or PYRIN-1 protein to further modulate a NBS-1 or PYRIN-1 target molecule. For example, the catalytic/enzymatic activity of the target molecule on an appropriate substrate can be determined as previously described.

In yet another embodiment, the cell-free assay comprises contacting the NBS-1 or PYRIN-1 protein or biologically active portion thereof with a known compound which binds NBS-1 or PYRIN-1 to form an assay mixture, contacting the assay mixture with a test compound, and determining the ability of the test compound to interact with a NBS-1 or PYRIN-1 protein, wherein determining the ability of the test compound to interact with a NBS-1 or PYRIN-1 protein comprises determining the ability of the NBS-1 or PYRIN-1 protein to preferentially bind to or modulate the activity of a NBS-1 or PYRIN-1 target molecule. The cell-free assays of the present invention are amenable to use of either the soluble form or a membrane-associated form of NBS-1 or PYRIN-1. A membrane-associated form of NBS-1 or PYRIN-1 refers to NBS-1 or PYRIN-1 that interacts with a membrane-bound target molecule. In the case of cell-free assays comprising the membrane-associated form of NBS-1 or PYRIN-1, it may be desirable to utilize a solubilizing agent such that the membrane-associated form of NBS-1 or PYRIN-1 is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly (ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl═N,N-dimethyl-3-ammonio-1-propane sulfonate.

In more than one embodiment of the above assay methods of the present invention, it may be desirable to immobilize either NBS-1 or PYRIN-1 or its target molecule to facilitate separation of complexed from uncomplexed forms of one or both of the proteins, as well as to accommodate automation of the assay. Binding of a test compound to NBS-1 or PYRIN-1, or interaction of NBS-1 or PYRIN-1 with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/NBS-1 or PYRIN-1 fusion proteins or glutathione-S-transferase/target fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or NBS-1 or PYRIN-1 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of NBS-1 or PYRIN-1 binding or activity determined using standard techniques. In an alternative embodiment, MYC or HA epitope tag NBS-1 or PYRIN-1 fusion proteins or MYC or HA epitope tag target fusion proteins can be adsorbed onto anti-MYC or anti-HA antibody coated microbeads or onto anti-MYC or anti-HA antibody coated microtitre plates, which are then combined with the test compound or the test compound and either the non-adsorbed target protein or NBS-1 or PYRIN-1 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of NBS-1 or PYRIN-1 binding or activity determined using standard techniques.

Other techniques for immobilizing proteins on matrices can also be used in the screening assays of the invention. For example, NBS-1 or PYRIN-1 or its target molecule can be immobilized utilizing conjugation of biotin and streptavidin. Biotinylated NBS-1 or PYRIN-1 target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with NBS-1 or PYRIN-1 or target molecules but which do not interfere with binding of the protein to its target molecule can be derivatized to the wells of the plate, and unbound target or protein trapped in the wells by antibody conjugation. Methods for detecting such complexes, in addition to those described above for the GST-immobilized complexes and epitope tag immobilized complexes, include immunodetection of complexes using antibodies reactive with the NBS-1 or PYRIN-1 or target molecule, as well as enzyme-linked assays which rely on detecting an enzymatic activity associated with the NBS-1 or PYRIN-1 or a target molecule.

In another embodiment, modulators of NBS-1 or PYRIN-1 expression are identified in a method in which a cell is contacted with a candidate compound and the expression of the NBS-1 or PYRIN-1 promoter, mRNA or protein in the cell is determined. The level of expression of NBS-1 or PYRIN-1 mRNA or protein in the presence of the candidate compound is compared to the level of expression of NBS-1 or PYRIN-1 mRNA or protein in the absence of the candidate compound. The candidate compound can then be identified as a modulator of NBS-1 or PYRIN-1 expression based on this comparison. For example, when expression of NBS-1 or PYRIN-1 mRNA or protein is greater (statistically significantly greater) in the presence of the candidate compound than in its absence, the candidate compound is identified as a stimulator of NBS-1 or PYRIN-1 mRNA or protein expression. Alternatively, when expression of NBS-1 or PYRIN-1 mRNA or protein is less (statistically significantly less) in the presence of the candidate compound than in its absence, the candidate compound is identified as an inhibitor of NBS-1 or PYRIN-1 mRNA or protein expression. The level of NBS-1 or PYRIN-1 mRNA or protein expression in the cells can be determined by methods described herein for detecting NBS-1 or PYRIN-1 mRNA or protein. The activity of the NBS-1 or PYRIN-1 promoter can be assayed by linking the NBS-1 or PYRIN-1 promoter to a reporter gene such as luciferase, secreted alkaline phosphatase, or beta-galactosidase and introducing the resulting construct into an appropriate vector, transfecting a host cell line, and measuring the activity of the reporter gene in response to test compounds.

In yet another aspect of the invention, the NBS-1 or PYRIN-1 proteins can be used as "bait proteins" in a two-hybrid assay (for a discussion of a mammalian two-hybrid assay, see e.g., Hosfield and Chang (1999) *Strategies Newsletter* 2(2):62-65) or three hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Bio/Techniques 14:920-924; Iwabuchi et al. (1993) Oncogene 8:1693-1696; and PCT Publication No. WO 94/10300), to identify other proteins, which bind to or interact with NBS-1 or PYRIN-1 ("NBS-1 or PYRIN-1-binding proteins" or "NBS-1 or PYRIN-1-bp") and modulate NBS-1 or PYRIN-1 activity. Such NBS-1 or PYRIN-1-binding proteins are also likely to be involved in the propagation of signals by the NBS-1 or PYRIN-1 proteins as, for example, upstream or downstream elements of the NBS-1 or PYRIN-1 pathway.

The two-hybrid system is based on the modular nature of most transcription factors, which consist of separable DNA-binding and activation domains. Briefly, the assay utilizes two different DNA constructs. In one construct, the gene that codes for NBS-1 or PYRIN-1 is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a NBS-1 or PYRIN-1-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with NBS-1 or PYRIN-1.

In an embodiment of the invention, the ability of a test compound to modulate the activity of NBS-1 or PYRIN-1, or a biologically active portion thereof can be determined by assaying the ability of the test compound to block the binding of NBS-1 or PYRIN-1 to its target proteins in a yeast or mammalian two-hybrid system assay. This assay could be automated for high throughput drug screening purposes. In another embodiment of the invention, NBS-1 or PYRIN-1 and a target protein could be configured in the reverse two-hybrid system (Vidal et al. (1996) Proc. Natl. Acad. Sci. USA 93:10321-6 and Vidal et al. (1996) Proc. Natl. Acad Sci. USA 93:10315-20) designed specifically for efficient drug screening. In the reverse two-hybrid system, inhibition of a NBS-1 or PYRIN-1 physical interaction with a target protein would result in induction of a reporter gene in contrast to the normal two-hybrid system where inhibition of NBS-1 or PYRIN-1 physical interaction with a target protein would lead to reporter gene repression. The reverse two-hybrid system is preferred for drug screening because reporter gene induction is more easily assayed than report gene repression.

Alternative embodiments of the invention are proteins found to physically interact with proteins that bind to NBS-1 or PYRIN-1. NBS-1 or PYRIN-1 interactors could be configured into two-hybrid system baits and used in two-hybrid screens to identify additional members of the NBS-1 or PYRIN-1 pathway. The interactors of NBS-1 or PYRIN-1 interactors identified in this way could be useful targets for therapeutic intervention in NBS-1 or PYRIN-1 related diseases and pathologies and an assay of their enzymatic or binding activity could be useful for the identification of test compounds that modulate NBS-1 or PYRIN-1 activity.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. Accordingly, NBS-1 or PYRIN-1 nucleic acid molecules described herein or fragments thereof, can be used to map the location of NBS-1 or PYRIN-1 genes on a chromosome. The mapping of the NBS-1 or PYRIN-1 sequences to chromosomes is an important first step in correlating these sequences with genes associated with disease.

Briefly, NBS-1 or PYRIN-1 genes can be mapped to chromosomes by preparing PCR primers (preferably 15-25 bp in length) from the NBS-1 or PYRIN-1 sequences. Computer analysis of NBS-1 or PYRIN-1 sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the NBS-1 or PYRIN-1 sequences will yield an amplified fragment. Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio et al. (1983) Science 220:919-924). Somatic cell-hybrids containing only fragments of human chromosomes can also be produced using human chromosomes with translocations and deletions.

PCR mapping of somatic cell hybrids is a rapid procedure for assigning a particular sequence to a particular chromosome. Three or more sequences can be assigned per day using a single thermal cycler. Using the NBS-1 or PYRIN-1 sequences to design oligonucleotide primers, sublocalization can be achieved with panels of fragments from specific chromosomes. Other mapping strategies which can similarly be used to map a NBS-1 or PYRIN-1 sequence to its chromosome include in situ hybridization (described in Fan et al. (1990) Proc. Natl. Acad. Sci. USA 87:6223-27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., (Human Chromosomes: A Manual of Basic Techniques (Pergamon Press, New York, 1988)).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) Nature, 325:783-787.

Moreover, differences in the DNA sequences between individuals affected and unaffected with a disease associated with the NBS-1 or PYRIN-1 gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

A NBS-1 or PYRIN-1 polypeptide and fragments and sequences thereof and antibodies specific thereto can be used to map the location of the gene encoding the polypeptide on a chromosome. This mapping can be carried out by specifically detecting the presence of the polypeptide in members of a panel of somatic cell hybrids between cells of a first species of animal from which the protein originates and cells from a second species of animal and then determining which somatic cell hybrid(s) expresses the polypeptide and noting the chromosome(s) from the first species of animal that it contains. For examples of this technique, see Pajunen et al. (1988) *Cytogenet. Cell Genet.* 47:37-41 and Van Keuren et al. (1986) *Hum. Genet.* 74:34-40. Alternatively, the presence of the NBS-1 or PYRIN-1 polypeptide in the somatic cell hybrids can be determined by assaying an activity or property of the polypeptide, for example, enzymatic activity, as described in Bordelon-Riser et al. (1979) *Somatic Cell Genetics* 5:597-613 and Owerbach et al. (1978) *Proc. Natl. Acad. Sci. USA* 75:5640-5644.

2. Tissue Typing

The NBS-1 or PYRIN-1 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the NBS-1 or PYRIN-1 sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The NBS-1 or PYRIN-1 sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 or SEQ ID NO:4 can comfortably provide positive individual identification with a panel of perhaps 10 to 1,000 primers which each yield a noncoding amplified sequence of 100 bases. If predicted coding sequences, such as those in SEQ ID NO:3 or SEQ ID NO:6 are used, a more appropriate number of primers for positive individual identification would be 500-2,000.

If a panel of reagents from NBS-1 or PYRIN-1 sequences described herein is used to generate a unique identification database for an individual, those same reagents can later be used to identify tissue from that individual. Using the unique identification database, positive identification of the individual, living or dead, can be made from extremely-small tissue samples.

3. Use of Partial Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 or SEQ ID NO:4 are particularly appropriate for this use as greater numbers of polymorphisms occur in the noncoding regions, making it easier to differentiate individuals using this technique. Examples of polynucleotide reagents include the NBS-1 or PYRIN-1 sequences or portions thereof, e.g., fragments derived from the noncoding regions of SEQ ID NO:1 or SEQ ID NO:4 which have a length of at least 20 or 30 bases.

The sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such NBS-1 or PYRIN-1 probes can be used to identify tissue by species and/or by organ type.

In a similar fashion, these reagents, e.g., NBS-1 or PYRIN-1 primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining NBS-1 or PYRIN-1 protein and/or nucleic acid expression as well as NBS-1 or PYRIN-1 activity, in the context of a biological sample (e.g., blood, serum, cells, tissue) to thereby determine whether an individual is afflicted with a disease or disorder, or is at risk of developing a disorder, associated with aberrant NBS-1 or PYRIN-1 expression or activity. The invention also provides for prognostic (or predictive) assays for determining whether an individual is at risk of developing a disorder associated with NBS-1 or PYRIN-1 protein, nucleic acid expression or activity. For example, mutations in a NBS-1 or PYRIN-1 gene can be assayed in a biological sample. Such assays can be used for prognostic or predictive purpose to thereby prophylactically treat an individual prior to the onset of a disorder characterized by or associated with NBS-1 or PYRIN-1 protein, nucleic acid expression or activity.

Another aspect of the invention provides methods for determining NBS-1 or PYRIN-1 protein, nucleic acid expression or NBS-1 or PYRIN-1 activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs or other compounds) on the expression or activity of NBS-1 or PYRIN-1 in clinical trials.

These and other agents are described in further detail in the following sections.

1. Diagnostic Assays

An exemplary method for detecting the presence or absence of NBS-1 or PYRIN-1 in a biological sample involves obtaining a biological sample from a test subject and contacting the biological sample with a compound or an agent capable of detecting NBS-1 or PYRIN-1 protein or nucleic acid (e.g., mRNA, genomic DNA) that encodes NBS-1 or PYRIN-1 protein such that the presence of NBS-1 or PYRIN-1 is detected in the biological sample. An agent for detecting NBS-1 or PYRIN-1 mRNA or genomic DNA is a labeled nucleic acid probe capable of hybridizing to NBS-1 or PYRIN-1 mRNA or genomic DNA. The nucleic acid probe can be, for example, a full-length NBS-1 or PYRIN-1 nucleic acid, such as the nucleic acid of SEQ ID NO:1, SEQ ID NO:3, SEQ ID NO:4, SEQ ID NO:6, or a portion thereof, such as an oligonucleotide of at least 15, 30, 50, 100, 250, 500, 750, 1000, 1250, or 1500 nucleotides in length and sufficient to specifically hybridize under stringent conditions to mRNA or genomic DNA. Other suitable probes for use in the diagnostic assays of the invention are described herein.

An agent for detecting NBS-1 or PYRIN-1 protein can be an antibody capable of binding to NBS-1 or PYRIN-1 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, biological fluids, and stool samples isolated from a subject, as well as tissues, cells and fluids present within a subject. That is, the detection method of the invention can be used to detect NBS-1 or PYRIN-1 mRNA, protein, or genomic DNA in a biological sample in vitro as well as in vivo. For example, in vitro techniques for detection of NBS-1 or PYRIN-1 mRNA include Northern hybridizations and in situ hybridizations. In vitro techniques for detection of NBS-1 or PYRIN-1 protein include enzyme linked immunosorbent assays (ELISAs), Western blots, immunoprecipitations and immunofluorescence. In vitro techniques for detection of NBS-1 or PYRIN-1 genomic DNA include Southern hybridizations. Furthermore, in vivo techniques for detection of NBS-1 or PYRIN-1 protein include introducing into a subject a labeled anti-NBS-1 or PYRIN-1 antibody. For example, the antibody can be labeled with a radioactive marker whose presence and location in a subject can be detected by standard imaging techniques.

Stool samples may be analyzed using various in vitro techniques, including techniques directed to analysis of DNA, RNA, or protein in the sample (Machiels et al. (2000) BioTechniques 28:286-290).

In one embodiment, the biological sample contains protein molecules from the test subject. Alternatively, the biological sample can contain mRNA molecules from the test subject or genomic DNA molecules from the test subject. A biological sample is a peripheral blood leukocyte sample isolated by conventional means from a subject.

In another embodiment, the methods further involve obtaining a control biological sample from a control subject, contacting the control sample with a compound or agent capable of detecting NBS-1 or PYRIN-1 protein, mRNA, or genomic DNA, such that the presence of NBS-1 or PYRIN-1 protein, mRNA or genomic DNA is detected in the biological sample, and comparing the presence of NBS-1 or PYRIN-1 protein, mRNA or genomic DNA in the control sample with the presence of NBS-1 or PYRIN-1 protein, mRNA or genomic DNA in the test sample.

The invention also encompasses kits for detecting the presence of NBS-1 or PYRIN-1 in a biological sample (a test sample). Such kits can be used to determine if a subject is suffering from or is at increased risk of developing a disorder associated with aberrant expression of NBS-1 or PYRIN-1 (e.g., an immunological disorder). For example, the kit can comprise a labeled compound or agent capable of detecting NBS-1 or PYRIN-1 protein or mRNA in a biological sample and means for determining the amount of NBS-1 or PYRIN-1 in the sample (e.g., an anti-NBS-1 or PYRIN-1 antibody or an oligonucleotide probe which binds to DNA encoding NBS-1 or PYRIN-1, e.g., SEQ ID NO:1, SEQ ID NO:3, SEQ ID NO:4, SEQ ID NO:6). Kits may also include instruction for observing that the tested subject is suffering from or is at risk of developing a disorder associated with aberrant expression of NBS-1 or PYRIN-1 if the amount of NBS-1 or PYRIN-1 protein or mRNA is above or below a normal level.

For antibody-based kits, the kit may comprise, for example: (1) a first antibody (e.g., attached to a solid support) which binds to NBS-1 or PYRIN-1 protein; and, optionally, (2) a second, different antibody which binds to NBS-1 or PYRIN-1 protein or the first antibody and is conjugated to a detectable agent. For oligonucleotide-based kits, the kit may comprise, for example: (1) a oligonucleotide, e.g., a detectably labeled oligonucleotide, which hybridizes to a NBS-1 or PYRIN-1 nucleic acid sequence or (2) a pair of primers useful for amplifying a NBS-1 or PYRIN-1 nucleic acid molecule.

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of NBS-1 or PYRIN-1.

2. Prognostic Assays

The methods described herein can furthermore be utilized as diagnostic or prognostic assays to identify subjects having or at risk of developing a disease or disorder associated with aberrant NBS-1 or PYRIN-1 expression or activity. For example, the assays described herein, such as the preceding diagnostic assays or the following assays, can be utilized to identify a subject having or at risk of developing a disorder associated with NBS-1 or PYRIN-1 protein, nucleic acid expression or activity. Alternatively, the prognostic assays can be utilized to identify a subject having or at risk for developing such a disease or disorder. Thus, the present invention provides a method in which a test sample is obtained from a subject and NBS-1 or PYRIN-1 protein or nucleic acid (e.g., mRNA, genomic DNA) is detected, wherein the presence of NBS-1 or PYRIN-1 protein or nucleic acid is diagnostic for a subject having or at risk of developing a disease or disorder associated with aberrant NBS-1 or PYRIN-1 expression or activity. As used herein, a "test sample" refers to a biological sample obtained from a subject of interest. For example, a test sample can be a biological fluid (e.g., serum), cell sample, tissue, or stool sample. Stool samples may be analyzed using various in vitro techniques, including techniques directed to analysis of DNA, RNA, or protein in the sample (Machiels et al. (2000) BioTechniques 28:286-290). Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant NBS-1 or PYRIN-1 expression or activity. For example, such methods can be used to determine whether a subject can be effectively treated with a specific agent or class of agents (e.g., agents of a type which decrease NBS-1 or PYRIN-1 activity). Thus, the present invention provides methods for determining whether a subject can be effectively treated with an agent for a disorder associated with aberrant NBS-1 or PYRIN-1 expression or activity in which a test sample is obtained and NBS-1 or PYRIN-1 protein or nucleic acid is detected (e.g., wherein the presence of NBS-1 or PYRIN-1 protein or nucleic acid is diagnostic for a subject that can be administered the agent to treat a disorder associated with aberrant NBS-1 or PYRIN-1 expression or activity).

The methods of the invention can also be used to detect genetic lesions or mutations in a NBS-1 or PYRIN-1 gene, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion characterized by at least one of an alteration affecting the integrity of a gene encoding a NBS-1 or PYRIN-1-protein, or the mis-expression of the NBS-1 or PYRIN-1 gene. For example, such genetic lesions can be detected by ascertaining the existence of at least one of 1) a deletion of one or more nucleotides from a NBS-1 or PYRIN-1 gene; 2) an addition of one or more nucleotides to a NBS-1 or PYRIN-1 gene; 3) a substitution of one or more nucleotides of a NBS-1 or PYRIN-1 gene; 4) a chromosomal rearrangement of a NBS-1 or PYRIN-1 gene; 5) an alteration in the level of a messenger RNA transcript of a NBS-1 or PYRIN-1 gene; 6) aberrant modification of a NBS-1 or PYRIN-1 gene, such as of the methylation pattern of the genomic DNA; 7) the presence of a non-wild type splicing pattern of a messenger RNA transcript of a NBS-1 or PYRIN-1 gene (e.g., caused by a mutation in a splice donor or splice acceptor site); 8) a non-wild type level of a NBS-1 or PYRIN-1-protein; 9) allelic loss of a NBS-1 or PYRIN-1 gene; and 10) inappropriate post-translational modification of a NBS-1 or PYRIN-1-protein. As described herein, there are a large number of assay techniques known in the art which can be used for detecting lesions in a NBS-1 or PYRIN-1 gene. A biological sample is a peripheral blood leukocyte sample isolated by conventional means from a subject.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in the NBS-1 or PYRIN-1 gene (see, e.g., Abravaya et al. (1995) Nucleic Acids Res. 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to a NBS-1 or PYRIN-1 gene under conditions such that hybridization and amplification of the NBS-1 or PYRIN-1-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) Proc. Natl. Acad. Sci. USA 87:1874-1878), transcriptional amplification system (Kwoh, et al. (1989) Proc. Natl. Acad. Sci. USA 86:1173-1177), Q-Beta Replicase (Lizardi et al. (1988) Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a NBS-1 or PYRIN-1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in NBS-1 or PYRIN-1 can be identified by hybridizing a sample and control nucleic acids, e.g., DNA or RNA, to high density arrays containing hundreds or thousands of oligonucleotides probes (Cronin et al. (1996) Human Mutation 7:244-255; Kozal et al. (1996) Nature Medicine 2:753-759). For example, genetic mutations in NBS-1 or PYRIN-1 can be identified in two-dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the NBS-1 or PYRIN-1 gene and detect mutations by comparing the sequence of the sample NBS-1 or PYRIN-1 with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Bio/Techniques 19:448), including sequencing by mass spectrometry (see, e.g., PCT Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in the NBS-1 or PYRIN-1 gene include methods in which protection from cleavage agents is, used to detect mismatched bases in RNA/RNA or RNA/DNA heteroduplexes (Myers et al. (1985) Science 230:1242). In general, the art technique of "mismatch cleavage" starts by providing heteroduplexes of formed by hybridizing (labeled) RNA or DNA containing the wild-type NBS-1 or PYRIN-1 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al (1988) Proc. Natl Acad Sci USA 85:4397; Saleeba et al (1992) Methods Enzymol. 217:286-295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in NBS-1 or PYRIN-1 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on a NBS-1 or PYRIN-1 sequence, e.g., a wild-type NBS-1 or PYRIN-1 sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in NBS-1 or PYRIN-1 genes. For example, single strand conformation polymorphism (SSCP) may be used to detect differences in electrophoretic mobility between mutant and wild type nucleic acids (Orita et al. (1989) Proc Natl. Acad. Sci USA: 86:2766, see also Cotton (1993) Mutat. Res. 285:125-144; and Hayashi (1992) Genet Anal Tech Appl 9:73-79). Single-stranded DNA fragments of sample and control NBS-1 or PYRIN-1 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In an embodiment, the subject method utilizes heteroduplex analysis to separate double stranded heteroduplex molecules on the basis of changes in electrophoretic mobility (Keen et al. (1991) Trends Genet 7:5).

In yet another embodiment, the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl Acad. Sci USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition, it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a NBS-1 or PYRIN-1 gene.

Furthermore, any cell type or tissue, preferably peripheral blood leukocytes, in which NBS-1 or PYRIN-1 is expressed may be utilized in the prognostic assays described herein.

3. Pharmacogenomics

Agents, or modulators which have a stimulatory or inhibitory effect on NBS-1 or PYRIN-1 activity (e.g., NBS-1 or PYRIN-1 gene expression) as identified by a screening assay described herein can be administered to individuals to treat (prophylactically or therapeutically) disorders (e.g., a neurodegenerative disease such as Alzheimer's disease) associated with aberrant NBS-1 or PYRIN-1 activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of NBS-1 or PYRIN-1 protein, expression of NBS-1 or PYRIN-1 nucleic acid, or mutation content of NBS-1 or PYRIN-1 genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) Clin. Chem. 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM exhibit no therapeutic response, as demonstrated for the analgesic effect of codeine mediated by its CYP2D6-formed metabolite morphine. The other extreme are the so-called ultra-rapid metabolizers who do not respond to standard doses. Recently, the molecular basis of ultra-rapid metabolism has been identified to be due to CYP2D6 gene amplification.

Thus, the activity of NBS-1 or PYRIN-1 protein, expression of NBS-1 or PYRIN-1 nucleic acid, or mutation content of NBS-1 or PYRIN-1 genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a NBS-1 or PYRIN-1 modulator, such as a modulator identified by one of the exemplary screening assays described herein.

4. Monitoring of Effects During Clinical Trials

Monitoring the influence of agents (e.g., drugs, compounds) on the expression or activity of NBS-1 or PYRIN-1 (e.g., the ability to modulate aberrant cell proliferation and/or differentiation) can be applied not only in basic drug screening, but also in clinical trials. For example, the effectiveness of an agent determined by a screening assay as described herein to increase NBS-1 or PYRIN-1 gene expression, protein levels, or upregulate NBS-1 or PYRIN-1 activity, can be monitored in clinical trails of subjects exhibiting decreased NBS-1 or PYRIN-1 gene expression, protein levels, or downregulated NBS-1 or PYRIN-1 activity. Alternatively, the effectiveness of an agent determined by a screening assay to decrease NBS-1 or PYRIN-1 gene expression, protein levels, or downregulated NBS-1 or PYRIN-1 activity, can be monitored in clinical trials of subjects exhibiting increased NBS-1 or PYRIN-1 gene expression, protein levels, or upregulated NBS-1 or PYRIN-1 activity. In such clinical trials, the expression or activity of NBS-1 or PYRIN-1 and, preferably, other genes that have been implicated in, for example, a cellular proliferation disorder can be used as a "read out" or markers of the immune responsiveness of a particular cell.

For example, and not by way of limitation, genes, including NBS-1 or PYRIN-1, that are modulated in cells by treatment with an agent (e.g., compound, drug or small molecule) which modulates NBS-1 or PYRIN-1 activity (e.g., identified in a screening assay as described herein) can be identified. Thus, to study the effect of agents on cellular proliferation disorders, for example, in a clinical trial, cells can be isolated and RNA prepared and analyzed for the levels of expression of NBS-1 or PYRIN-1 and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of NBS-1 or PYRIN-1 or other genes. In this way, the gene expression pattern can serve as a marker, indicative of the physiological response of the cells to the agent. Accordingly, this response state may be determined before, and at various points during, treatment of the individual with the agent.

In an embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a NBS-1 or PYRIN-1 protein, mRNA, or genomic DNA in the preadministration sample; (iii) obtaining one or more post-administration samples from the subject; (iv) detecting the level of expression or activity of the NBS-1 or PYRIN-1 protein, mRNA, or genomic DNA in the post-administration samples; (v) comparing the level of expression or activity of the NBS-1 or PYRIN-1 protein, mRNA, or genomic DNA in the pre-administration sample with the NBS-1 or PYRIN-1 protein, mRNA, or genomic DNA in the post administration sample or samples; and (vi) altering the administration of the agent to the subject accordingly. For example, increased administration of the agent may be desirable to increase the expression or activity of NBS-1 or PYRIN-1 to higher levels than detected, i.e., to increase the effectiveness of the agent. Alternatively, decreased administration of the agent may be desirable to decrease expression or activity of NBS-1 or PYRIN-1 to lower levels than detected, i.e., to decrease the effectiveness of the agent.

5. Transcriptional Profiling

The NBS-1 or PYRIN-1 nucleic acid molecules described herein, including small oligonucleotides, can be used in transcriptionally profiling. For example, these nucleic acids can be used to examine the expression of NBS-1 or PYRIN-1 in normal tissue or cells and in tissue or cells subject to a disease state, e.g., tissue or cells derived from a patient having a disease of interest or cultured cells which model or reflect a disease state of interest, e.g., cells of a cultured tumor cell line. By measuring expression of NBS-1 or PYRIN-1, together or individually, a profile of expression in normal and disease states can be developed. This profile can be used diagnostically and to examine the effectiveness of a therapeutic regime.

C. Methods of Treatment

The present invention provides for both prophylactic and therapeutic methods of treating a subject at risk of (or susceptible to) a disorder or having a disorder associated with aberrant NBS-1 or PYRIN-1 expression or activity, examples of which are provided herein.

1. Prophylactic Methods

In one aspect, the invention provides a method for preventing in a subject, a disease or condition associated with an aberrant NBS-1 or PYRIN-1 expression or activity, by administering to the subject an agent which modulates NBS-1 or PYRIN-1 expression or at least one NBS-1 or PYRIN-1 activity. Subjects at risk for a disease which is caused or contributed to by aberrant NBS-1 or PYRIN-1 expression or activity can be identified by, for example, any or a combination of diagnostic or prognostic assays as described herein. Administration of a prophylactic agent can occur prior to the manifestation of symptoms characteristic of the NBS-1 or PYRIN-1 aberrancy, such that a disease or disorder is prevented or, alternatively, delayed in its progression. Depending on the type of NBS-1 or PYRIN-1 aberrancy, for example, a NBS-1 or PYRIN-1 agonist or NBS-1 or PYRIN-1 antagonist agent can be used for treating the subject. The appropriate agent can be determined based on screening assays described herein.

2. Therapeutic Methods

Another aspect of the invention pertains to methods of modulating NBS-1 or PYRIN-1 expression or activity for therapeutic purposes. The modulatory method of the invention involves contacting a cell with an agent that modulates one or more of the activities of NBS-1 or PYRIN-1 protein activity associated with the cell. An agent that modulates NBS-1 or PYRIN-1 protein activity can be an agent as described herein, such as a nucleic acid or a protein, a naturally-occurring cognate ligand of a NBS-1 or PYRIN-1 protein, a peptide, a NBS-1 or PYRIN-1 peptidomimetic, or other small molecule. In one embodiment, the agent stimulates one or more of the biological activities of NBS-1 or PYRIN-1 protein. Examples of such stimulatory agents include active NBS-1 or PYRIN-1 protein and a nucleic acid molecule encoding NBS-1 or PYRIN-1 that has been introduced into the cell. In another embodiment, the agent inhibits one or more of the biological activities of NBS-1 or PYRIN-1 protein. Examples of such inhibitory agents include antisense NBS-1 or PYRIN-1 nucleic acid molecules and anti-NBS-1 or PYRIN-1 antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a NBS-1 or PYRIN-1 protein or nucleic acid molecule or a disorder related to NBS-1 or PYRIN-1 expression or activity. In one embodiment, the method involves administering an agent (e.g., an agent identified by a screening assay described herein), or combination of agents that modulates (e.g., upregulates or downregulates) NBS-1 or PYRIN-1 expression or activity. In another embodiment, the method involves administering a NBS-1 or PYRIN-1 protein or nucleic acid molecule as therapy to compensate for reduced or aberrant NBS-1 or PYRIN-1 expression or activity. Stimulation of NBS-1 or PYRIN-1 activity is desirable in situations in which NBS-1 or PYRIN-1 is abnormally downregulated and/or in which increased NBS-1 or PYRIN-1 activity is likely to have a beneficial effect. Conversely, inhibition of NBS-1 or PYRIN- activity is desirable in situations in which NBS-1 or PYRIN-1 is abnormally upregulated, e.g., in myocardial infarction, and/or in which decreased NBS-1 or PYRIN-1 activity is likely to have a beneficial effect.

This invention is further illustrated by the following examples which should not be construed as limiting. The contents of all references, patents and published patent applications cited throughout this application are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid comprising a nucleotide sequence that encodes a polypeptide comprising an amino acid sequence that is at least 95% identical to the sequence of SEQ ID NO:5, wherein the polypeptide comprises contiguous amino acid residues 263-357 of SEQ ID NO: 5, and wherein the polypeptide binds a nucleotide.

2. The nucleic acid of claim 1, wherein the amino acid sequence is at least 98% identical to the sequence of SEQ ID NO:5.

3. The nucleic acid of claim 1, wherein the nucleotide sequence encodes a polypeptide that further comprises contiguous amino acid residues 1-87 of SEQ ID NO:5.

4. The nucleic acid of claim 1, wherein the nucleotide sequence encodes a polypeptide that further comprises contiguous amino acid residues 740-991 of SEQ ID NO:5.

5. A vector comprising the nucleic acid of claim 1.

6. A host cell in culture comprising the nucleic acid of claim 1.

7. A method for producing a polypeptide, the method comprising culturing the host cell of claim 6 under conditions in which the nucleic acid is expressed.

8. The nucleic acid of claim 1, further comprising a sequence encoding a heterologous polypeptide.

9. An isolated nucleic acid comprising a nucleotide sequence that encodes a polypeptide comprising an amino acid sequence that is at least 95% identical to the sequence of SEQ ID NO:5, wherein the polypeptide comprises contiguous amino acid residues 1-87 of SEQ ID NO: 5, and wherein the polypeptide binds a pyrin domain-containing polypeptide.

10. The nucleic acid of claim 9, wherein the amino acid sequence is at least 98% identical to the sequence of SEQ ID NQ:5.

11. The nucleic acid of claim 9, wherein the polypeptide further comprises amino acid residues 740-991 of SEQ ID NO:5.

12. The nucleic acid of claim 9, wherein the amino acid sequence is at least 98% identical to the sequence of SEQ ID NO:5.

13. An isolated nucleic acid comprising a nucleotide sequence that encodes amino acid residues 1-87 of SEQ ID NO:5 and binds a pyrin domain-containing polypeptide.

14. An isolated nucleic acid comprising a nucleotide sequence that encodes amino acid residues 263-357 of SEQ ID NO:5 and binds a nucleotide.

15. An isolated nucleic acid comprising a nucleotide sequence that encodes a polypeptide comprising the amino acid sequence of SEQ ID NO:5.

16. The nucleic acid of claim 15, wherein the polypeptide consists of the amino acid sequence of SEQ ID NO:5.

17. An isolated nucleic acid comprising the nucleotide sequence of SEQ ID NO:6.

18. The nucleic acid of claim 17, wherein the nucleic acid consists of the nucleotide sequence of SEQ ID NO:6.

19. The nucleic acid of claim 17, wherein the nucleic acid comprises the nucleotide sequence of SEQ ID NO:4.

20. The nucleic acid of claim 19, wherein the nucleic acid consists of the nucleotide sequence of SEQ ID NO:4.

21. A host cell in culture comprising the nucleic acid of claim 17.

22. A method for producing a polypeptide, the method comprising culturing the host cell of claim 21 under conditions in which the nucleic acid is expressed.

23. An isolated nucleic acid consisting of a fragment of SEQ ID NO:6, wherein the fragment comprises at least 400 contiguous nucleotides of the nucleotide sequence of SEQ ID NO:6 and encodes a polypeptide which comprises amino acids 263-357 of SEQ ID NO:5 and binds a nucleotide.

24. The nucleic acid of claim 23, wherein the fragment comprises at least 500 contiguous nucleotides of the nucleotide sequence of SEQ ID NO:6.

25. The nucleic acid of claim 24, wherein the fragment comprises at least 1000 contiguous nucleotides of the nucleotide sequence of SEQ ID NO:6.

26. The nucleic acid of claim 25, wherein the fragment comprises at least 1600 contiguous nucleotides of the nucleotide sequence of SEQ ID NO:6.

27. An isolated nucleic acid that encodes a fusion protein consisting of amino acids 1-87 of SEQ ID NO:5 and a non-PYRIN-1 nolynentide, wherein the amino acids 1-87 of SEQ ID NO:5 bind a pyrin domain-containina polypeptide.

28. A vector comprising the nucleic acid of claim 27.

29. The vector of claim 28, wherein the vector comprises nucleic acid sequences which regulate expression of a polypeptide encoded by the nucleic acid.

30. A host cell in culture comprising the vector of claim 29.

31. The host cell of claim 30, which is a mammalian host cell.

32. A method for producing a polypeptide, the method comprising culturing the host cell of claim 31 under conditions in which the nucleic acid is expressed.

* * * * *

UNITED STATES PATENT AND TRADEMARK OFFICE
CERTIFICATE OF CORRECTION

| | | |
|---|---|---|
| PATENT NO. | : 7,321,028 B2 | Page 1 of 1 |
| APPLICATION NO. | : 10/132967 | |
| DATED | : January 22, 2008 | |
| INVENTOR(S) | : John Bertin | |

It is certified that error appears in the above-identified patent and that said Letters Patent is hereby corrected as shown below:

In Column 100, Claim 27, Line 34, please change "nolynentide" to "polypeptide".

In Column 100, Claim 27, Line 35, please change "domain-containina" to "domain-containing".

Signed and Sealed this

Nineteenth Day of May, 2009

JOHN DOLL
*Acting Director of the United States Patent and Trademark Office*